(12) United States Patent (10) Patent No.: US 8,148,342 B2
Feinstein et al. (45) Date of Patent: *Apr. 3, 2012

(54) OLIGORIBONUCLEOTIDES AND METHODS OF USE THEREOF FOR TREATMENT OF ALOPECIA, ACUTE RENAL FAILURE AND OTHER DISEASES

(75) Inventors: Elena Feinstein, Rehovot (IL); Shai Ehrlich, Walnut Creek, CA (US)

(73) Assignee: Quark Pharmaceuticals Inc., Fremont, CA (US)

( * ) Notice: Subject to any disclaimer, the term of this patent is extended or adjusted under 35 U.S.C. 154(b) by 849 days.

This patent is subject to a terminal disclaimer.

(21) Appl. No.: 12/008,578

(22) Filed: Jan. 11, 2008

(65) Prior Publication Data

US 2008/0287382 A1 Nov. 20, 2008

Related U.S. Application Data

(62) Division of application No. 11/237,598, filed on Sep. 27, 2005.

(60) Provisional application No. 60/613,991, filed on Sep. 28, 2004, provisional application No. 60/658,196, filed on Mar. 2, 2005, provisional application No. 60/703,020, filed on Jul. 26, 2005.

(51) Int. Cl.
*A61K 31/70* (2006.01)
(52) U.S. Cl. .......................................... 514/44
(58) Field of Classification Search .................. None
See application file for complete search history.

(56) References Cited

U.S. PATENT DOCUMENTS

| | | | |
|---|---|---|---|
| 4,497,817 A | 2/1985 | Murase et al. | |
| 5,849,774 A * | 12/1998 | Jackson et al. | 514/392 |
| 5,898,031 A | 4/1999 | Crooke | |
| 6,107,094 A | 8/2000 | Crooke | |
| 6,372,249 B1 | 4/2002 | Smith et al. | |
| 6,506,559 B1 | 1/2003 | Fire et al. | |
| 6,593,353 B1 | 7/2003 | Gudkov et al. | |
| 6,982,277 B2 | 1/2006 | Gudkov et al. | |
| 7,008,956 B2 | 3/2006 | Gudkov et al. | |
| 7,012,087 B2 | 3/2006 | Gudkov et al. | |
| 7,056,704 B2 | 6/2006 | Tuschl | |
| 7,078,196 B2 | 7/2006 | Tuschl | |
| 7,432,249 B2 | 10/2008 | Crooke | |
| 7,432,250 B2 | 10/2008 | Crooke | |
| 7,452,987 B2 | 11/2008 | Giese | |
| 7,459,547 B2 | 12/2008 | Zamore | |
| 7,629,321 B2 | 12/2009 | Crooke | |
| 7,741,299 B2 | 6/2010 | Feinstein et al. | |
| 7,781,575 B2 | 8/2010 | Khvorova et al. | |
| 7,825,099 B2 | 11/2010 | Feinstein et al. | |
| 7,842,674 B2 | 11/2010 | Feinstein | |
| 7,893,245 B2 | 2/2011 | Giese | |
| 7,910,566 B2 | 3/2011 | Feinstein | |
| 2002/0019425 A1 | 2/2002 | Gudkov et al. | |
| 2004/0014956 A1 | 1/2004 | Woolf et al. | |
| 2004/0180351 A1 | 9/2004 | Giese et al. | |
| 2004/0209832 A1 | 10/2004 | McSwiggen | |
| 2005/0080246 A1 | 4/2005 | Allerson et al. | |
| 2005/0255487 A1 | 11/2005 | Khvorova et al. | |
| 2005/0261191 A1 * | 11/2005 | Barasch et al. | 514/12 |
| 2006/0069056 A1 | 3/2006 | Feinstein et al. | |
| 2006/0217329 A1 | 9/2006 | Feinstein | |
| 2007/0031844 A1 | 2/2007 | Khvorova et al. | |
| 2007/0185047 A1 | 8/2007 | Bhat et al. | |
| 2008/0108583 A1 | 5/2008 | Feinstein | |
| 2008/0161426 A1 | 7/2008 | Gudkov | |
| 2008/0287382 A1 | 11/2008 | Feinstein et al. | |
| 2009/0082291 A1 | 3/2009 | Feinstein et al. | |
| 2009/0105173 A1 | 4/2009 | Feinstein | |
| 2010/0029746 A1 | 2/2010 | Feinstein | |
| 2010/0048425 A1 | 2/2010 | Khvorova | |

FOREIGN PATENT DOCUMENTS

| | | |
|---|---|---|
| EP | 0430334 A1 | 6/2002 |
| EP | 2284266 | 2/2011 |
| WO | WO 99/55910 | 11/1999 |
| WO | WO 00/44895 | 8/2000 |
| WO | WO 00/44914 | 8/2000 |
| WO | WO 01/36646 A1 | 5/2001 |
| WO | WO 01/68836 | 9/2001 |
| WO | WO 01/75164 A2 | 10/2001 |
| WO | WO 02/44321 A2 | 6/2002 |
| WO | WO 2004/015107 A2 | 6/2002 |
| WO | WO 02/055693 | 7/2002 |
| WO | WO 02/059300 | 8/2002 |
| WO | WO 03/062394 | 7/2003 |
| WO | WO 03/064626 | 8/2003 |

(Continued)

OTHER PUBLICATIONS

Kelly et al. Journal of the American Society of Nephrology 2003 vol. 14, pp. 128-138.*
Matta et al. Cancer Biology & Therapy 2003, vol. 2, pp. 206-210.*
Amarzguioui M et al. (2003) Tolerance for mutations and chemical modifications in a siRNA. Nucleic Acids Res. 31(2):589-95.
Czauderna F, et al. (2003) Structural variations and stabilising modifications of synthetic siRNAs in mammalian cells. Nucleic Acids Res. 31(11):2705-16.
Elbashir SM et al. (2001) Functional anatomy of siRNAs for mediating efficient RNAi in Drosophila melanogaster embryo lysate. EMBO J. 20(23):6877-88.
Prakash TP et al. (2005) Positional effect of chemical modifications on short interference RNA activity in mammalian cells. J. Med. Chem. 48(13):4247-53.

(Continued)

*Primary Examiner* — Tracy Vivlemore
(74) *Attorney, Agent, or Firm* — John P. White; Cooper & Dunham LLP

(57) ABSTRACT

The invention relates to a double-stranded compound, preferably an oligoribonucleotide, which down-regulates the expression of a human p53 gene. The invention also relates to a pharmaceutical composition comprising the compound, or a vector capable of expressing the oligoribonucleotide compound, and a pharmaceutically acceptable carrier. The present invention also contemplates a method of treating a patient suffering from alopecia or acute renal failure or other diseases comprising administering to the patient the pharmaceutical composition in a therapeutically effective dose so as to thereby treat the patient. The alopecia may be induced by chemotherapy or radiotherapy, and the patient may be suffering from cancer, in particular breast cancer.

26 Claims, 8 Drawing Sheets

FOREIGN PATENT DOCUMENTS

| WO | WO 03/070918 A2 | 8/2003 |
|---|---|---|
| WO | WO 2003/064625 | 8/2003 |
| WO | WO 03/074654 A2 | 9/2003 |
| WO | WO 2004/041889 | 5/2004 |
| WO | WO 2004/044136 | 5/2004 |
| WO | WO 2004/111191 | 12/2004 |
| WO | WO 2005/062937 | 7/2005 |
| WO | WO 2006/006948 | 1/2006 |
| WO | WO 2006/035434 A2 | 4/2006 |
| WO | WO 2007/087451 | 8/2007 |
| WO | WO 2009/001359 | 12/2008 |

OTHER PUBLICATIONS

Office Action issued on May 1, 2008 in connection with U.S. Appl. No. 11/655,610, filed Jan. 18, 2007.

Office Action issued on Oct. 2, 2008 in connection with U.S. Appl. No. 11/655,610, filed Jan. 18, 2007.

Office Action issued on Oct. 28, 2008 in connection with U.S. Appl. No. 11/237,598, filed Sep. 27, 2005.

International Preliminary Report on Patentability issued by WIPO on Apr. 2, 2009 in connection with International Application No. PCT/IL2005/001035.

Barik, Sailen (2005.). "Silence of the Transcripts; RNA Interference in Medicine," J. Mol. Med. 83:764-773.

Bartel, D.P., (2004) MicroRNAs: Genomics, Biogenesis, Mechanism, and Function. Cell 116:281-297.

Bernstein, E., et al., (2001) Role for a bidentate ribonuclease in the initiation step of RNA interference. Nature 409:363-366.

Bitko, Vira et al. (2004). "Inhibition of Respiratory Viruses by Nasally Administered siRNA," Nature Medicine, 11(1):50-55.

Botchkarev, V.A., et al., (2000) p53 Is Essential for Chemotherapy-induced Hair Loss. Cancer Res. 60:5002-5006.

Brummelkamp, T.R., et al., (2002) A System for Stable Expression of Short Interfering RNAs in Mammalian Cells. Science 296:550-553.

Caplen, N.J., et al., (2001) Specific inhibition of gene expression by small-stranded RNAs in invertebrate and vertebrate systems. Proc. Natl. Acad. Sci. USA 98(17):9742-9747.

Chakraborty, Chiranjib (2007) "Potentially of Small Interfering RNAs (siRNA) as Recent Therapeutic Targets for Gene-Silencing," Current Drug Targets, 8:469-482.

Chalk, A.M., et al., (2004) Improved and automated prediction of effective siRNA. Biochem. Biophys. Res. Commun. 319:264-274.

Chernov, M.V. and Stark, G.R., (1997) The p53 activation and apoptosis induced by DNA damage are reversibly inhibited by salicylate. Oncogene 14:2503-2510.

Cotsarelis, G. and Millar, S.E., (2001) Towards a molecular understanding of hair loss and its treatment. Trends Mol. Med. 7(7):293-301.

Elbashir, S.M., et al., (2001) RNA interference is mediated by 21- and 22-nucleotide RNAs. Genes Dev. 15:188-200.

Elbashir, S.M., et al., (2001) Duplexes of 21-nucleotide RNAs mediate RNA interference in cultured mammalian cells. Nature 411:494-498.

Fire, A., et al., (1998) Potent and specific genetic interference by double-stranded RNA in Caenorhabditis elegans. Nature 391:806-811.

Gottlieb, T.M., et al., (1996) p53 in growth control and neoplasia. Biochim Biophys Acta 1287:77-102.

Komarov, P.G., et al., (1999) A Chemical Inhibitor of p53 That Protects Mice from the Side Effects of Cancer Therapy. Science 285:1733-1737.

Komarova, E.A., et al., (1997) Transgenic mice with p53-responsive lacZ: p53 activity varies dramatically during normal . . . EMBO J. 16(6):1391-1400.

Lee, Youngtae et al., (2003). "The nuclear RNase III Drosha initiates mircoRNA processing," Nature, 425:415-419.

Levenkova, N., et al., (2004) Gene specific siRNA selector. Bioinformatics 20(3):430-432.

McManus, M.T. and Sharp, P.A., (2002) Gene Silencing in Mammals by Small Interfering RNAs. Nature Rev. Genet. 3:737-747.

Sioud, M. and Leirdal, M., (2004) Potential design rules and enzymatic synthesis of siRNAs. Methods Mol. Biol. 252:457-469.

Steele, R.J.C., et al., (1998) The p53 tumour suppressor gene. Br. J. Surg. 85:1460-1467.

Supavekin, S., et al., (2003) Differential gene expression following early renal ischemia/reperfusion. Kidney Int. 63:1714-1724.

TeKippe, M., et al., (2003) Expansion of hematopoietic stem cell phenotype and activity in Trp53-null mice. Exp. Hematol. 31:521-527.

Tolentino, M.J., et al., (2004) Intravitreal Injection of Vascular Endothelial Growth Factor Small Interfering . . . , Retina 24:132-138.

Ui-Tei, K., et al., (2004) Guidelines for the selection of highly effective siRNA sequences for mammalian and chick RNA interference. Nucleic Acids Res. 32(3):936-948.

Wang, J. et al., (2003). "A Peptide Inhibitor of c-Jun N-Terminal Kinase Protects against Both Aminoglycoside . . . ," The J. of Neuroscience, 23(24):8596-8607.

Wlodarski, P., et al., (1998) Role of p53 in Hematopoietic Recovery After Cytotoxic Treatment. Blood 91(8):2998-3006.

Zhang, M. et al., (2003). "Pifithrin-α Supresses p53 and Protects Cochlear and Vestibular Hair Cells From Cisplatin-Induced Apoptosis," Neuroscience, 120:191-205.

Elena Feinstein, et al., U.S. Appl. No. 11/827,199, filed Jul. 10, 2007.

Pending claims in Elena Feinstein, et al., U.S. Appl. No. 11/827,199, filed Jul. 10, 2007.

Andrei Gudkov et al., U.S. Appl. No. 11/136,231, filed May 24, 2005.

International Search Report issued by the International Searching Authority (ISA/US) on Dec. 3, 2007 in connection with International Application No. PCT/IL05/01035.

Written Opinion of the International Searching Authority (ISA/US) issued on Dec. 3, 2007 in connection with International Application No. PCT/IL05/01035.

Office Action issued on Mar. 23, 2001 in connection with U.S. Appl. No. 09/493,527, filed Jan. 28, 2000.

Office Action issued on Jul. 2, 2001 in connection with U.S. Appl. No. 09/493,527, filed Jan. 28, 2000.

Office Action issued on Dec. 28, 2001 in connection with U.S. Appl. No. 09/947,757, filed Sep. 6, 2001.

Office Action issued on Jun. 6, 2002 in connection with U.S. Appl. No. 09/493,527, filed Jan. 28, 2000.

Office Action issued on Feb. 12, 2003 in connection with U.S. Appl. No. 09/880,417, filed Jun. 13, 2001.

Office Action issued on Mar. 26, 2003 in connection with U.S. Appl. No. 09/947,757, filed Sep. 6, 2001.

Office Action issued on Jul. 15, 2001 in connection with U.S. Appl. No. 09/947,757, filed Sep. 6, 2001.

Office Action issued on Oct. 9, 2003 in connection with U.S. Appl. No. 09/880,417, filed Jun. 13, 2001.

Office Action issued on Nov. 19, 2003 in connection with U.S. Appl. No. 09/947,757, filed Sep. 6, 2001.

Office Action issued on Apr. 6, 2004 in connection with U.S. Appl. No. 10/350,560, filed Jan. 24, 2003.

Office Action issued on Jul. 9, 2004 in connection with U.S. Appl. No. 09/880,417, filed Jun. 13, 2001.

Office Action issued on Jul. 13, 2004 in connection with U.S. Appl. No. 09/947,757, filed Sep. 6, 2001.

Office Action issued on Nov. 26, 2004 in connection with U.S. Appl. No. 09/947,757, filed Sep. 6, 2001.

Office Action issued on Sep. 9, 2004 in connection with U.S. Appl. No. 10/352,597, filed Jan. 28, 2003.

Office Action issued on Jan. 3, 2005 in connection with U.S. Appl. No. 10/350,560, filed Jan. 24, 2003.

Office Action issued on Apr. 21, 2005 in connection with U.S. Appl. No. 10/352,597, filed Jan. 28, 2003.

Office Action issued on Oct. 30, 2007 in connection with U.S. Appl. No. 11/136,231, filed May 24, 2005.

Office Action issued Nov. 9, 2006 in connection with U.S. Appl. No. 11/237,598, filed Sep. 27, 2005.

Office Action issued Mar. 14, 2007 in connection with U.S. Appl. No. 11/237,598, filed Sep. 27, 2005.

Final Office Action issued Dec. 3, 2007 in connection with U.S. Appl. No. 11/237,598, filed Sep. 27, 2005.

Communication under Rule 112 EPC issued by the European Patent Office on Dec. 16, 2003 in connection with European Patent Application No. 00914455.1.

Communication pursuant to Article 96(2)EPC issued by the European Patent Office on Feb. 12, 2004 in connection with European Patent Application No. 00914455.1.
Communication pursuant to Article 96(2)EPC issued by the European Patent Office on Aug. 19, 2004 in connection with European Patent Application No. 00914455.1.
Communication pursuant to Article 96(2)EPC issued by the European Patent Office on May 13, 2005 in connection with European Patent Application No. 00914455.1.
Result of consultation issued by the European Patent Office on Oct. 25, 2005 in connection with European Patent Application No. 00914455.1.
Communication pursuant to Article 96(2)EPC issued by the European Patent Office on March 10, 2006 in connection with European Patent Application No. 00914455.1.
Communication pursuant to Article 96(2)EPC issued by the European Patent Office on Oct. 24, 2006 in connection with European Patent Application No. 00914455.1.
89. Pending claims in U.S. Appl. No. 11/136,231, filed May 24, 2005.
Non-Final Office Action Summary for U.S. Appl. No. 11/655,610 (Responsive to communication filed on Jan. 18, 2007).
Non-Final Office Action Summary for U.S. Appl. No. 11/655,610 (Responsive to communication filed on Jul. 3, 2008).
Notice of Allowance mailed on Apr. 7, 2009 in connection with Elena Feinstein et al., U.S. Appl. No. 11/655,610, filed Jan. 18, 2007.
Pending claims in U.S. Appl. No. 11/827,199 as of Jan. 25, 2010 (US 2009/0082291).
Pending claims in U.S. Appl. No. 12/006,722 (US 2009/0105173), 2009.
Notice of Allowance mailed on Nov. 5, 2010 in connection with Elena Feinstein et al., U.S. Appl. No. 12/006,722, filed Jan. 4, 2008.
Pending claims in Elena Feinstein, et al., U.S. Appl. No. 12/008,578, filed Jan. 11, 2008.
Pending claims filed June 20, 2008 in Elena Feinstein, et al., U.S. Appl. No. 12/008,578, filed Jan. 11, 2008.
Notice of Allowance and Allowed Claims in U.S. Appl. No. 12/586,271 (US 2010/0048425), 2010.
Search Report issued by the Australian Patent Office on May 14, 2008 in connection with Singaporean Application/Patent No. 0702035-7.
Written Opinion issued by the Australian Patent Office on May 14, 2008 in connection with Singaporean Application/Patent No. 0702035-7.
Second Written Opinion issued by the Australian Patent Office on May 26, 2009 in connection with Singapore Application No. 200702035-7.
Oct. 26, 2009 Response to Second Written Opinion issued by the Australian Patent Office on May 26, 2009 in connection with Singapore Application No. 200702035-7.
Jan. 27, 2010 Exam Report and decision of grant in connection with Singapore Application No. 200702035-7.

Office Action issued by the Russian Patent Office on Jul. 20, 2009 in connection with Russian Patent Application No. 2007/116168.
Office Action issued by the Russian Patent Office on Jun. 2, 2010 in connection with Russian Patent Application No. 2007/116168.
Decision of Grant issued by the Russian Patent Office on Apr. 4, 2011 in connection with Russian Patent Application No. 2007/116168.
PCT Written Opinion for International Application No. PCT/IL2005/01035 with a mailing date of Dec. 3, 2007.
Examination Report issued by the Australian Patent Office on Dec. 22, 2008 in connection with New Zealand Patent Application No. 553987.
Notice of Allowance mailed on Jul. 22, 2010 in connection with Elena Feinstein et al., U.S. Appl. No. 11/827,199, filed Jul. 10, 2007.
Final Office Action issued on Aug. 19, 2009 in connection with U.S. Appl. No. 11/237,598, filed Sep. 27, 2005.
Notice of Allowance mailed on Nov. 18, 2009 in connection with U.S. Appl. No. 11/237,598, filed Sep. 27, 2005, and allowed claims.
Office Action issued May 10, 2010 in connection with U.S. Appl. No. 11/237,598, filed Sep. 27, 2005.
Nov. 10, 2010 Amendment and Response to Office Action issued May 10, 2010 in connection with U.S. Appl. No. 11/237,598, filed Sep. 27, 2005.
Office Action issued Feb. 15, 2011 in connection with U.S. Appl. No. 11/237,598, filed Sep. 27, 2005.
First Office Action issued Mar. 29, 2010 in connection with Chinese Patent Application No. 200580032715.4 filed Sep. 27, 2005.
Aug. 12, 2010 Response and Amendment to First Office Action issued Mar. 29, 2010 in connection with Chinese Patent Application No. 200580032715.4 filed Sep. 27, 2005.
Office Action issued by the Japanese Patent Office on Feb. 8, 2011 in connection with Japanese Patent Application No. 2007-534174.
Chiu et al., siRNA Function in RNAi: A Chemical modification analysis, RNA, (2003), 9:1034-1048.
Hall et al., RNA interference using boranophosphate siRNAs: structure-activity relationships, nucleic acids research, (2004), vol. 32(20): 5991-6000.
Layzer et al., In vivo activity if nuclease-resistant siRNAs, RNA, (2004), 10: 766-771.
Molitoris, BA et al. (2009) "siRNA Targeted to p53 *Attenuates Ischemic and Cisplatin-Induced Acute Kidney Injury*", JASN Express, 20: 1754-1764.
Scherer and Rossi. (2003) "Approaches for the sequence—specific knockdown of mRNA". Nat. Biotechnol., 21(12): 1457-1465.
Scherer and Rossi (2004) Therapeutic Applications of RNA Interferences: Recent Advances in siRNA Design. Advances in Genetics 22:1-21.
Molitoris, BA (2003) "Transitioning to Therapy in Ischemic Acute Renal Failure." J. Am. Soc. Nephrol. 14: 265-267.

* cited by examiner

Figure 1

Homo sapiens tumor protein p53 (Li-Fraumeni syndrome) (TP53), mRNA gi|8400737|ref|NM_000546.2

```
Hum-TP53     1  ACTTGTCATG GCGACTGTCC AGCTTTGTGC CAGGAGCCTC GCAGGGGTTG ATGGGATTGG GGTTTTCCCC    70
Hum-TP53    71  TCCCATGTGC TCAAGACTGG CGCTAAAAGT TTTGAGCTTC TCAAAAGTCT AGAGCCACCG TCCAGGGAGC   140
Hum-TP53   141  AGGTAGCTGC TGGGCTCCGG GGACACTTTG CGTTCGGGCT GGGAGCGTGC TTTCCACGAC GGTGACACGC   210
Hum-TP53   211  TTCCCTGGAT TGGCAGCCAG ACTGCCTTCC GGGTCACTGC CATGGAGGAG CCGCAGTCAG ATCCTAGCGT   280
Hum-TP53   281  CGAGCCCCCT CTGAGTCAGG AAACATTTTC AGACCTATGG AAACTACTTC CTGAAAACAA CGTTCTGTCC   350
Hum-TP53   351  CCCTTGCCGT CCCAAGCAAT GGATGATTTG ATGCTGTCCC CGGACGATAT TGAACAATGG TTCACTGAAG   420
Hum-TP53   421  ACCCAGGTCC AGATGAAGCT CCCAGAATGC CAGAGGCTGC TCCCCCCGTG GCCCCTGCAC CAGCAGCTCC   490
Hum-TP53   491  TACACCGGCG GCCCCTGCAC CAGCCCCCTC CTGGCCCCTG TCATCTTCTG TCCCTTCCCA GAAAACCTAC   560
Hum-TP53   561  CAGGGCAGCT ACGGTTTCCG TCTGGGCTTC TTGCATTCTG GGACAGCCAA GTCTGTGACT TGCACGTACT   630
Hum-TP53   631  CCCCTGCCCT CAACAAGATG TTTTGCCAAC TGGCCAAGAC CTGCCCTGTG CAGCTGTGGG TTGATTCCAC   700
Hum-TP53   701  ACCCCCGCCC GGCACCCGCG TCCGCGCCAT GGCCATCTAC AAGCAGTCAC AGCACATGAC GGAGGTTGTG   770
Hum-TP53   771  AGGCGCTGCC CCCACCATGA GCGCTGCTCA GATAGCGATG GTCTGGCCCC TCCTCAGCAT CTTATCCGAG   840
Hum-TP53   841  TGGAAGGAAA TTTGCGTGTG GAGTATTTGG ATGACAGAAA CACTTTTCGA CATAGTGTGG TGGTGCCCTA   910
Hum-TP53   911  TGAGCCGCCT GAGGTTGGCT CTGACTGTAC CACCATCCAC TACAACTACA TGTGTAACAG TTCCTGCATG   980
Hum-TP53   981  GGCGGCATGA ACCGGAGGCC CATCCTCACC ATCATCACAC TGGAAGACTC CAGTGGTAAT CTACTGGGAC  1050
Hum-TP53  1051  GGAACAGCTT TGAGGTGCGT GTTTGTGCCT GTCCTGGGAG AGACCGGCGC ACAGAGGAAG AGAATCTCCG  1120
Hum-TP53  1121  CAAGAAAGGG GAGCCTCACC ACGAGCTGCC CCCAGGGAGC ACTAAGCGAG CACTGCCCAA CAACACCAGC  1190
Hum-TP53  1191  TCCTCTCCCC AGCCAAAGAA GAAACCACTG GATGGAGAAT ATTTCACCCT TCAGATCCGT GGGCGTGAGC  1260
```

Figure 1 (Continued)

```
Hum-TP53  1261  GCTTCGAGAT GTTCCGAGAG CTGAATGAGG CCTTGGAACT CAAGGATGCC CAGGCTGGGA AGGAGCCAGG  1330
Hum-TP53  1331  GGGGAGCAGG GCTCACTCCA GCCACCTGAA GTCCAAAAAG GGTCAGTCTA CCTCCCGCCA TAAAAAACTC  1400
Hum-TP53  1401  ATGTTCAAGA CAGAAGGGCC TGACTCAGAC TGACATTCTC CACTTCTTGT TCCCCACTGA CAGCCTCCCA  1470
Hum-TP53  1471  CCCCCATCTC TCCCTCCCCT GCCATTTTGG GTTTTGGGTC TTTGAACCCT TGCTTGCAAT AGGTGTGCGT  1540
Hum-TP53  1541  CAGAAGCACC CAGGACTTCC ACTTGCTTTG TCCCGGGGCT CCACTGAACA AGTTGGCCTG CACTGGTGTT  1610
Hum-TP53  1611  TTGTTGTGGG GAGGAGGATG GGGAGTAGGA CATAACCACCT TAGATTTTAA GGTTTTTACT GTGAGGGATG  1680
Hum-TP53  1681  TTTGGGAGAT GTAAGAAATG TTCTTGCAGT TAAGGGTTAG TTTACAATCA GCCACATTCT AGGTAGGTAG  1750
Hum-TP53  1751  GGGCCCACTT CACCGTACTA ACCAGGGAAG CTGTCCCTCA TGTTGAATTT TCTCTAACTT CAAGGCCCAT  1820
Hum-TP53  1821  ATCTGTGAAA TGCTTGGCATT TCCACCTACC TATTACATGG GTTAATGAGG CATTGTGAGG TAATCTACAT  1890
Hum-TP53  1891  CTGGCCTTGA AACCACTTT TATTACATGG TTGACCCCCT TGAGGGTGCC TGTTCCCTCT  1960
Hum-TP53  1961  CCCTCTCCCT GTTGGCTGGT GGGTTGGTAG TTTCTACAGT TGGGCAGCTG GTTAGGTAGA GGGAGTTGTC  2030
Hum-TP53  2031  AAGTCTTGCT GGGCCAGCCA AACCCTGTCT GACAACCTCT TGGTCGACCT TAGTACCCAA AAGGAAATCT  2100
Hum-TP53  2101  CACCCCATCC AGGATTTCAT CTCTTGTATA TGATGATCTG GATCCACCAA GACTTGTTTT  2170
Hum-TP53  2171  ATGCTCAGGG TCAATTTCTT TTTTCTTTTT TTTCTTTTTC CTGCAGCCTT TTTGAGACTG GGTCTCGCTT  2240
Hum-TP53  2241  TGTTGCCCAG GCTGGAGTGG AGTGCGGTGA TCTTGGCTTA CTGCAGCCTT TGCCTCCCCG GCTCGAGCAG  2310
Hum-TP53  2311  TCCTGCCTCA GCCTCCCGAG TAGCTGGGAC TAGCGTTGCC CACAGGTTCA TGCCACCATG GCCAGCCAAC TTTTGCATGT  2380
Hum-TP53  2381  TTTGTAGAGA TGGGGTCTCA CAGTGTTGCC CAGGCTGGTC TCAAACTCCT GGGCTCAGGC GATCCACCTG  2450
Hum-TP53  2451  TCTCAGCCTC CCAGAGTGCT GGGATTACAA GCATTTCAC CCCACCCTTC CCCTCCTTCT CTGGAAGGGT CTGGAAGGGT CAACATCTTT  2520
Hum-TP53  2521  TACATTCTGC AAGCACATCT GCATTTTCAC CCCACCCTTC CCCTCCTTCT CCCTTTTTAT ATCCCATTTT  2590
Hum-TP53  2591  TATATCGATC TCTTATTTTA CAATAAAACT TTCCTGCCA 2629
```

Note that the start (ATG) and stop (TGA) codons are underlined

Figure 2

Protein - Homo sapiens tumor protein p53 (Li-Fraumeni syndrome) (TP53)

```
Hum_TP53_prot    1  MEEPQSDPSV EPPLSQETFS DLWKLLPENN VLSPLPSQAM DDLMLSPDDI EQWFTEDPGP DEAPRMPEAA
Hum_TP53_prot   71  PRVAPAPAAP TPAAPAPAPS WPLSSSVPSQ KTYQGSYGFR LGFLHSGTAK SVTCTYSPAL NKMFCQLAKT
                      _
Hum_TP53_prot  141  CPVQLWVDST PPPGTRVRAM AIYKQSQHMT EVVRRCPHHE RCSDSDGLAP PQHLIRVEGN LRVEYLDDRN
Hum_TP53_prot  211  TFRHSVVVPY EPPEVGSDCT TIHYNYMCNS SCMGGMNRRP ILTIITLEDS SGNLLGRNSF EVRVCACPGR
                                                                                      _     _
Hum_TP53_prot  281  DRRTEEENLR KKGEPHHELP GSTKRALPN NTSSSPQKK KPLDGEYFTL QIRGRERFEM FRELNEALEL
                                               _
Hum_TP53_prot  351  KDAQAGKEPG GSRAHSSHLK SKKGQSTSRH KKLMFKTEGP DSD 393
```

Variations in other human entries in GeneBank(gi- 23491728; gi-35209; gi-13097806):
R72 -> P
R273 -> H
P278 -> A
P309 -> S

SEQUENCE LISTING

```
<160> NUMBER OF SEQ ID NOS: 316

<210> SEQ ID NO 1
<211> LENGTH: 2629
<212> TYPE: DNA
<213> ORGANISM: Homo sapiens

<400> SEQUENCE: 1
acttgtcatg gcgactgtcc agctttgtgc caggagcctc gcaggggttg atgggattgg      60
ggttttcccc tcccatgtgc tcaagactgg cgctaaaagt tttgagcttc tcaaaagtct     120
agagccaccg tccagggagc aggtagctgc tgggctccgg ggacactttg cgttcgggct     180
gggagcgtgc tttccacgac ggtgacacgc ttccctggat tggcagccag actgccttcc     240
gggtcactgc catggaggag ccgcagtcag atcctagcgt cgagcccct ctgagtcagg      300 aaacattttc agacctatgg aaactacttc ctgaaaacaa cgttctgtcc cccttgccgt     360
cccaagcaat ggatgatttg atgctgtccc cggacgatat tgaacaatgg ttcactgaag     420
acccaggtcc agatgaagct cccagaatgc cagaggctgc tccccgcgtg gcccctgcac     480
cagcagctcc tacaccggcg gcccctgcac cagcccctc ctggccctg tcatcttctg      540 tcccttccca gaaaacctac cagggcagct acggtttccg tctgggcttc ttgcattctg     600
ggacagccaa gtctgtgact tgcacgtact cccctgccct caacaagatg ttttgccaac     660
tggccaagac ctgccctgtg cagctgtggg ttgattccac accccgcc ggcacccgcg       720 tccgcgccat ggccatctac aagcagtcac agcacatgac ggaggttgtg aggcgctgcc     780
cccaccatga gcgctgctca gatagcgatg gtctggcccc tcctcagcat cttatccgag     840
tggaaggaaa tttgcgtgtg gagtatttgg atgacagaaa cactttttcga catagtgtgg     900 tggtgcccta tgagccgcct gaggttggct ctgactgtac caccatccac tacaactaca     960
tgtgtaacag ttcctgcatg ggcggcatga accggaggcc catcctcacc atcatcacac    1020
tggaagactc cagtggtaat ctactgggac ggaacagctt tgaggtgcgt gtttgtgcct    1080
```

```
gtcctgggag agaccggcgc acagaggaag agaatctccg caagaaaggg gagcctcacc    1140
acgagctgcc cccagggagc actaagcgag cactgcccaa caacaccagc tcctctcccc    1200
agccaaagaa gaaaccactg gatggagaat atttcaccct tcagatccgt gggcgtgagc    1260
gcttcgagat gttccgagag ctgaatgagg ccttggaact caaggatgcc caggctggga    1320
aggagccagg ggggagcagg gctcactcca gccacctgaa gtccaaaaag gtcagtctca    1380
cctcccgcca taaaaaactc atgttcaaga cagaagggcc tgactcagac tgacattctc    1440
cacttcttgt tccccactga cagcctccca ccccatctc tccctcccct gccattttgg     1500
gttttgggtc tttgaaccct tgcttgcaat aggtgtgcgt cagaagcacc caggacttcc    1560
atttgctttg tcccgggggct ccactgaaca agttggcctg cactggtgtt ttgttgtggg   1620
gaggaggatg gggagtagga cataccagct tagatttaa ggttttact gtgagggatg      1680 tttgggagat gtaagaaatg ttcttgcagt taagggttag tttacaatca gccacattct    1740
aggtaggtag gggcccactt caccgtacta accagggaag ctgtccctca tgttgaattt    1800
tctctaactt caaggcccat atctgtgaaa tgctggcatt tgcacctacc tcacagagtg    1860
cattgtgagg gttaatgaaa taatgtacat ctggccttga aaccacctt tattacatgg     1920 ggtctaaaac ttgacccct tgagggtgcc tgttccctct ccctctccct gttggctggt     1980
gggttggtag tttctacagt tgggcagctg gttaggtaga gggagttgtc aagtcttgct    2040
ggcccagcca aaccctgtct gacaacctct tggtcgacct tagtacctaa aaggaaatct    2100 cacccccatcc cacaccctgg aggatttcat ctcttgtata tgatgatctg gatccaccaa   2160
gacttgtttt atgctcaggg tcaatttctt tttctttt tttttttt tttcttttc         2220 tttgagactg gtctcgcctt tgttgcccag gctggagtgg agtggcgtga tcttggctta    2280
ctgcagcctt tgcctccccg gctcgagcag tcctgcctca gcctccggag tagctgggac    2340
cacaggttca tgccaccatg gccagccaac ttttgcatgt tttgtagaga tggggtctca    2400
cagtgttgcc caggctggtc tcaaactcct gggctcaggc gatccacctg tctcagcctc    2460
ccagagtgct gggattacaa ttgtgagcca ccacgtggag ctggaagggt caacatcttt    2520
tacattctgc aagcacatct gcattttcac cccacccttc ccctccttct cccttttat    2580 atcccatttt tatatcgatc tcttattta caataaaact tgctgcca                  2629
```

<210> SEQ ID NO 2
<211> LENGTH: 393
<212> TYPE: PRT
<213> ORGANISM: Homo sapiens

<400> SEQUENCE: 2

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
```

```
               100                 105                 110
Phe Leu His Ser Gly Thr Ala Lys Ser Val Thr Cys Thr Tyr Ser Pro
            115                 120                 125
Ala Leu Asn Lys Met Phe Cys Gln Leu Ala Lys Thr Cys Pro Val Gln
            130                 135                 140
Leu Trp Val Asp Ser Thr Pro Pro Gly Thr Arg Val Arg Ala Met
145                 150                 155                 160
Ala Ile Tyr Lys Gln Ser Gln His Met Thr Glu Val Val Arg Arg Cys
            165                 170                 175
Pro His His Glu Arg Cys Ser Asp Ser Asp Gly Leu Ala Pro Pro Gln
            180                 185                 190
His Leu Ile Arg Val Glu Gly Asn Leu Arg Val Glu Tyr Leu Asp Asp
            195                 200                 205
Arg Asn Thr Phe Arg His Ser Val Val Val Pro Tyr Glu Pro Pro Glu
            210                 215                 220
Val Gly Ser Asp Cys Thr Thr Ile His Tyr Asn Tyr Met Cys Asn Ser
225                 230                 235                 240
Ser Cys Met Gly Gly Met Asn Arg Arg Pro Ile Leu Thr Ile Ile Thr
            245                 250                 255
Leu Glu Asp Ser Ser Gly Asn Leu Leu Gly Arg Asn Ser Phe Glu Val
            260                 265                 270
Arg Val Cys Ala Cys Pro Gly Arg Asp Arg Arg Thr Glu Glu Glu Asn
            275                 280                 285
Leu Arg Lys Lys Gly Glu Pro His His Glu Leu Pro Pro Gly Ser Thr
            290                 295                 300
Lys Arg Ala Leu Pro Asn Asn Thr Ser Ser Pro Gln Pro Lys Lys
305                 310                 315                 320
Lys Pro Leu Asp Gly Glu Tyr Phe Thr Leu Gln Ile Arg Gly Arg Glu
            325                 330                 335
Arg Phe Glu Met Phe Arg Glu Leu Asn Glu Ala Leu Glu Leu Lys Asp
            340                 345                 350
Ala Gln Ala Gly Lys Glu Pro Gly Gly Ser Arg Ala His Ser Ser His
            355                 360                 365
Leu Lys Ser Lys Lys Gly Gln Ser Thr Ser Arg His Lys Lys Leu Met
            370                 375                 380
Phe Lys Thr Glu Gly Pro Asp Ser Asp
385                 390

<210> SEQ ID NO 3
<211> LENGTH: 19
<212> TYPE: RNA
<213> ORGANISM: Mus musculus

<400> SEQUENCE: 3
guacaugugu aauagcucc                                                  19

<210> SEQ ID NO 4
<211> LENGTH: 19
<212> TYPE: RNA
<213> ORGANISM: Homo sapiens

<400> SEQUENCE: 4
gacuccagug guaaucuac                                                  19

<210> SEQ ID NO 5
<211> LENGTH: 19
<212> TYPE: RNA
```

<213> ORGANISM: Homo sapiens

<400> SEQUENCE: 5
cagaccuaug gaaacuacu                                                    19

<210> SEQ ID NO 6
<211> LENGTH: 19
<212> TYPE: RNA
<213> ORGANISM: Homo sapiens

<400> SEQUENCE: 6
cuaccucccg ccauaaaaa                                                    19

<210> SEQ ID NO 7
<211> LENGTH: 19
<212> TYPE: RNA
<213> ORGANISM: Homo sapiens

<400> SEQUENCE: 7
cccaagcaau ggaugauuu                                                    19

<210> SEQ ID NO 8
<211> LENGTH: 19
<212> TYPE: RNA
<213> ORGANISM: Homo sapiens

<400> SEQUENCE: 8
cccggacgau auugaacaa                                                    19

<210> SEQ ID NO 9
<211> LENGTH: 19
<212> TYPE: RNA
<213> ORGANISM: Mus musculus

<400> SEQUENCE: 9
gagucacagu cggauauca                                                    19

<210> SEQ ID NO 10
<211> LENGTH: 19
<212> TYPE: RNA
<213> ORGANISM: Mus musculus

<400> SEQUENCE: 10
ggauguugag gaguuuuuu                                                    19

<210> SEQ ID NO 11
<211> LENGTH: 19
<212> TYPE: RNA
<213> ORGANISM: Mus musculus

<400> SEQUENCE: 11 caucuuugu cccuucuca                                                     19

<210> SEQ ID NO 12
<211> LENGTH: 19
<212> TYPE: RNA
<213> ORGANISM: Mus musculus

<400> SEQUENCE: 12
ggaauagguu gauaguugu                                                    19

<210> SEQ ID NO 13
<211> LENGTH: 19
<212> TYPE: RNA

-continued

<213> ORGANISM: Mus musculus

<400> SEQUENCE: 13
ggacagccaa gucuguuau                                                    19

<210> SEQ ID NO 14
<211> LENGTH: 19
<212> TYPE: RNA
<213> ORGANISM: Mus musculus

<400> SEQUENCE: 14
gaagaaaauu uccgcaaaa                                                    19

<210> SEQ ID NO 15
<211> LENGTH: 19
<212> TYPE: RNA
<213> ORGANISM: Homo sapiens

<400> SEQUENCE: 15
cugggacagc caagucugu                                                    19

<210> SEQ ID NO 16
<211> LENGTH: 19
<212> TYPE: RNA
<213> ORGANISM: Homo sapiens

<400> SEQUENCE: 16
ucaucacacu ggaagacuc                                                    19

<210> SEQ ID NO 17
<211> LENGTH: 19
<212> TYPE: RNA
<213> ORGANISM: Homo sapiens

<400> SEQUENCE: 17
cacacuggaa gacuccagu                                                    19

<210> SEQ ID NO 18
<211> LENGTH: 19
<212> TYPE: RNA
<213> ORGANISM: Homo sapiens

<400> SEQUENCE: 18
gcgccauggc caucuacaa                                                    19

<210> SEQ ID NO 19
<211> LENGTH: 19
<212> TYPE: RNA
<213> ORGANISM: Homo sapiens

<400> SEQUENCE: 19
cgccauggcc aucuacaag                                                    19

<210> SEQ ID NO 20
<211> LENGTH: 19
<212> TYPE: RNA
<213> ORGANISM: Homo sapiens

<400> SEQUENCE: 20
agucacagca caugacgga                                                    19

<210> SEQ ID NO 21
<211> LENGTH: 19
<212> TYPE: RNA

<213> ORGANISM: Homo sapiens

<400> SEQUENCE: 21
uccgagugga aggaaauuu					19

<210> SEQ ID NO 22
<211> LENGTH: 19
<212> TYPE: RNA
<213> ORGANISM: Homo sapiens

<400> SEQUENCE: 22
ccgaguggaa ggaaauuug					19

<210> SEQ ID NO 23
<211> LENGTH: 19
<212> TYPE: RNA
<213> ORGANISM: Homo sapiens

<400> SEQUENCE: 23
gacagaaaca cuuuucgac					19

<210> SEQ ID NO 24
<211> LENGTH: 19
<212> TYPE: RNA
<213> ORGANISM: Homo sapiens

<400> SEQUENCE: 24
gugugguggu gcccauga					19

<210> SEQ ID NO 25
<211> LENGTH: 19
<212> TYPE: RNA
<213> ORGANISM: Homo sapiens

<400> SEQUENCE: 25
gagaauauuu cacccuuca					19

<210> SEQ ID NO 26
<211> LENGTH: 19
<212> TYPE: RNA
<213> ORGANISM: Mus musculus

<400> SEQUENCE: 26
ggagcuauua cacauguac					19

<210> SEQ ID NO 27
<211> LENGTH: 19
<212> TYPE: RNA
<213> ORGANISM: Homo sapiens

<400> SEQUENCE: 27
guagauuacc acuggaguc					19

<210> SEQ ID NO 28
<211> LENGTH: 19
<212> TYPE: RNA
<213> ORGANISM: Homo sapiens

<400> SEQUENCE: 28
aguaguuucc auaggucug					19

<210> SEQ ID NO 29
<211> LENGTH: 19
<212> TYPE: RNA

<213> ORGANISM: Homo sapiens

<400> SEQUENCE: 29
uuuuuauggc gggagguag                                                 19

<210> SEQ ID NO 30
<211> LENGTH: 19
<212> TYPE: RNA
<213> ORGANISM: Homo sapiens

<400> SEQUENCE: 30
aaaucaucca uugcuuggg                                                 19

<210> SEQ ID NO 31
<211> LENGTH: 19
<212> TYPE: RNA
<213> ORGANISM: Homo sapiens

<400> SEQUENCE: 31
uuguucaaua ucguccggg                                                 19

<210> SEQ ID NO 32
<211> LENGTH: 19
<212> TYPE: RNA
<213> ORGANISM: Mus musculus

<400> SEQUENCE: 32
ugauauccga cugugacuc                                                 19

<210> SEQ ID NO 33
<211> LENGTH: 19
<212> TYPE: RNA
<213> ORGANISM: Mus musculus

<400> SEQUENCE: 33
aaaaaacucc ucaacaucc                                                 19

<210> SEQ ID NO 34
<211> LENGTH: 19
<212> TYPE: RNA
<213> ORGANISM: Mus musculus

<400> SEQUENCE: 34
ugagaaggga caaaagaug                                                 19

<210> SEQ ID NO 35
<211> LENGTH: 19
<212> TYPE: RNA
<213> ORGANISM: Mus musculus

<400> SEQUENCE: 35
acaacuauca accuauucc                                                 19

<210> SEQ ID NO 36
<211> LENGTH: 19
<212> TYPE: RNA
<213> ORGANISM: Mus musculus

<400> SEQUENCE: 36
auaacagacu uggcugucc                                                 19

<210> SEQ ID NO 37
<211> LENGTH: 19
<212> TYPE: RNA

<213> ORGANISM: Mus musculus

<400> SEQUENCE: 37
uuuugcggaa auuucuuc                                          19

<210> SEQ ID NO 38
<211> LENGTH: 19
<212> TYPE: RNA
<213> ORGANISM: Homo sapiens

<400> SEQUENCE: 38
acagacuugg cugucccag                                         19

<210> SEQ ID NO 39
<211> LENGTH: 19
<212> TYPE: RNA
<213> ORGANISM: Homo sapiens

<400> SEQUENCE: 39
gagucuucca gugugauga                                         19

<210> SEQ ID NO 40
<211> LENGTH: 19
<212> TYPE: RNA
<213> ORGANISM: Homo sapiens

<400> SEQUENCE: 40
acuggagucu uccagugug                                         19

<210> SEQ ID NO 41
<211> LENGTH: 19
<212> TYPE: RNA
<213> ORGANISM: Homo sapiens

<400> SEQUENCE: 41
uuguagaugg ccauggcgc                                         19

<210> SEQ ID NO 42
<211> LENGTH: 19
<212> TYPE: RNA
<213> ORGANISM: Homo sapiens

<400> SEQUENCE: 42
cuuguagaug gccauggcg                                         19

<210> SEQ ID NO 43
<211> LENGTH: 19
<212> TYPE: RNA
<213> ORGANISM: Homo sapiens

<400> SEQUENCE: 43
uccgucaugu gcugugacu                                         19

<210> SEQ ID NO 44
<211> LENGTH: 19
<212> TYPE: RNA
<213> ORGANISM: Homo sapiens

<400> SEQUENCE: 44
aaauuuccuu ccacucgga                                         19

<210> SEQ ID NO 45
<211> LENGTH: 19
<212> TYPE: RNA

<213> ORGANISM: Homo sapiens

<400> SEQUENCE: 45
caaauuuccu uccacucgg                                                    19

<210> SEQ ID NO 46
<211> LENGTH: 19
<212> TYPE: RNA
<213> ORGANISM: Homo sapiens

<400> SEQUENCE: 46
gucgaaaagu guuucuguc                                                    19

<210> SEQ ID NO 47
<211> LENGTH: 19
<212> TYPE: RNA
<213> ORGANISM: Homo sapiens

<400> SEQUENCE: 47
ucauagggca ccaccacac                                                    19

<210> SEQ ID NO 48
<211> LENGTH: 19
<212> TYPE: RNA
<213> ORGANISM: Homo sapiens

<400> SEQUENCE: 48
ugaaggguga aauauucuc                                                    19

<210> SEQ ID NO 49
<211> LENGTH: 19
<212> TYPE: RNA
<213> ORGANISM: Homo sapiens

<400> SEQUENCE: 49
guaccaccau ccacuacaa                                                    19

<210> SEQ ID NO 50
<211> LENGTH: 19
<212> TYPE: RNA
<213> ORGANISM: Homo sapiens

<400> SEQUENCE: 50
ggaaacuacu uccugaaaa                                                    19

<210> SEQ ID NO 51
<211> LENGTH: 19
<212> TYPE: RNA
<213> ORGANISM: Homo sapiens

<400> SEQUENCE: 51
agacuccagu gguaaucua                                                    19

<210> SEQ ID NO 52
<211> LENGTH: 19
<212> TYPE: RNA
<213> ORGANISM: Homo sapiens

<400> SEQUENCE: 52
ccauccacua caacuacau                                                    19

<210> SEQ ID NO 53
<211> LENGTH: 19
<212> TYPE: RNA

<213> ORGANISM: Homo sapiens

<400> SEQUENCE: 53
ccaccaucca cuacaacua                                                    19

<210> SEQ ID NO 54
<211> LENGTH: 19
<212> TYPE: RNA
<213> ORGANISM: Homo sapiens

<400> SEQUENCE: 54
aaacacuuuu cgacauagu                                                    19

<210> SEQ ID NO 55
<211> LENGTH: 19
<212> TYPE: RNA
<213> ORGANISM: Homo sapiens

<400> SEQUENCE: 55
caugagcgcu gcucagaua                                                    19

<210> SEQ ID NO 56
<211> LENGTH: 19
<212> TYPE: RNA
<213> ORGANISM: Homo sapiens

<400> SEQUENCE: 56
ccauggccau cuacaagca                                                    19

<210> SEQ ID NO 57
<211> LENGTH: 19
<212> TYPE: RNA
<213> ORGANISM: Homo sapiens

<400> SEQUENCE: 57
ccaagucugu gacuugcac                                                    19

<210> SEQ ID NO 58
<211> LENGTH: 19
<212> TYPE: RNA
<213> ORGANISM: Homo sapiens

<400> SEQUENCE: 58
aaacuuugcu gccaaaaaa                                                    19

<210> SEQ ID NO 59
<211> LENGTH: 19
<212> TYPE: RNA
<213> ORGANISM: Homo sapiens

<400> SEQUENCE: 59
cccuccuucu cccuuuuua                                                    19

<210> SEQ ID NO 60
<211> LENGTH: 19
<212> TYPE: RNA
<213> ORGANISM: Homo sapiens

<400> SEQUENCE: 60
gcaagcacau cugcauuuu                                                    19

<210> SEQ ID NO 61
<211> LENGTH: 19
<212> TYPE: RNA

<213> ORGANISM: Homo sapiens

<400> SEQUENCE: 61
gggucaacau cuuuuacau                                          19

<210> SEQ ID NO 62
<211> LENGTH: 19
<212> TYPE: RNA
<213> ORGANISM: Homo sapiens

<400> SEQUENCE: 62
gaagggucaa caucuuua                                           19

<210> SEQ ID NO 63
<211> LENGTH: 19
<212> TYPE: RNA
<213> ORGANISM: Homo sapiens

<400> SEQUENCE: 63
cuggaagggu caacaucuu                                          19

<210> SEQ ID NO 64
<211> LENGTH: 19
<212> TYPE: RNA
<213> ORGANISM: Homo sapiens

<400> SEQUENCE: 64
ccagagugcu gggauuaca                                          19

<210> SEQ ID NO 65
<211> LENGTH: 19
<212> TYPE: RNA
<213> ORGANISM: Homo sapiens

<400> SEQUENCE: 65 gaugggucu cacaguguu                                           19

<210> SEQ ID NO 66
<211> LENGTH: 19
<212> TYPE: RNA
<213> ORGANISM: Homo sapiens

<400> SEQUENCE: 66
gccaacuuuu gcauguuuu                                          19

<210> SEQ ID NO 67
<211> LENGTH: 19
<212> TYPE: RNA
<213> ORGANISM: Homo sapiens

<400> SEQUENCE: 67
ccauggccag ccaacuuuu                                          19

<210> SEQ ID NO 68
<211> LENGTH: 19
<212> TYPE: RNA
<213> ORGANISM: Homo sapiens

<400> SEQUENCE: 68
agacccaggu ccagaugaa                                          19

<210> SEQ ID NO 69
<211> LENGTH: 19
<212> TYPE: RNA

<213> ORGANISM: Homo sapiens

<400> SEQUENCE: 69
ccaucaucac acuggaaga            19

<210> SEQ ID NO 70
<211> LENGTH: 19
<212> TYPE: RNA
<213> ORGANISM: Homo sapiens

<400> SEQUENCE: 70
caucacacug gaagacucc            19

<210> SEQ ID NO 71
<211> LENGTH: 19
<212> TYPE: RNA
<213> ORGANISM: Homo sapiens

<400> SEQUENCE: 71
caucaucaca cuggaagac            19

<210> SEQ ID NO 72
<211> LENGTH: 19
<212> TYPE: RNA
<213> ORGANISM: Homo sapiens

<400> SEQUENCE: 72
accaucauca cacuggaag            19

<210> SEQ ID NO 73
<211> LENGTH: 19
<212> TYPE: RNA
<213> ORGANISM: Homo sapiens

<400> SEQUENCE: 73
aucaucacac uggaagacu            19

<210> SEQ ID NO 74
<211> LENGTH: 19
<212> TYPE: RNA
<213> ORGANISM: Homo sapiens

<400> SEQUENCE: 74
cacuggaaga cuccagugg            19

<210> SEQ ID NO 75
<211> LENGTH: 19
<212> TYPE: RNA
<213> ORGANISM: Homo sapiens

<400> SEQUENCE: 75
acacuggaag acuccagug            19

<210> SEQ ID NO 76
<211> LENGTH: 19
<212> TYPE: RNA
<213> ORGANISM: Homo sapiens

<400> SEQUENCE: 76
ucacacugga agacuccag            19

<210> SEQ ID NO 77
<211> LENGTH: 19
<212> TYPE: RNA

<213> ORGANISM: Homo sapiens

<400> SEQUENCE: 77
aucacacugg aagacucca    19

<210> SEQ ID NO 78
<211> LENGTH: 19
<212> TYPE: RNA
<213> ORGANISM: Homo sapiens

<400> SEQUENCE: 78
cacagcacau gacggaggu    19

<210> SEQ ID NO 79
<211> LENGTH: 19
<212> TYPE: RNA
<213> ORGANISM: Homo sapiens

<400> SEQUENCE: 79
cacuggaaga cuccagugg    19

<210> SEQ ID NO 80
<211> LENGTH: 19
<212> TYPE: RNA
<213> ORGANISM: Homo sapiens

<400> SEQUENCE: 80
ucacagcaca ugacggagg    19

<210> SEQ ID NO 81
<211> LENGTH: 19
<212> TYPE: RNA
<213> ORGANISM: Homo sapiens

<400> SEQUENCE: 81
gucacagcac augacggag    19

<210> SEQ ID NO 82
<211> LENGTH: 19
<212> TYPE: RNA
<213> ORGANISM: Homo sapiens

<400> SEQUENCE: 82
ccauccacua caacuacau    19

<210> SEQ ID NO 83
<211> LENGTH: 19
<212> TYPE: RNA
<213> ORGANISM: Homo sapiens

<400> SEQUENCE: 83
ccaccaucca cuacaacua    19

<210> SEQ ID NO 84
<211> LENGTH: 19
<212> TYPE: RNA
<213> ORGANISM: Homo sapiens

<400> SEQUENCE: 84
gaauauuuca cccuucaga    19

<210> SEQ ID NO 85
<211> LENGTH: 19
<212> TYPE: RNA

<213> ORGANISM: Homo sapiens

<400> SEQUENCE: 85
cgaguggaag gaaauuugc                                                19

<210> SEQ ID NO 86
<211> LENGTH: 19
<212> TYPE: RNA
<213> ORGANISM: Homo sapiens

<400> SEQUENCE: 86
gagaauauuu cacccuuca                                                19

<210> SEQ ID NO 87
<211> LENGTH: 19
<212> TYPE: RNA
<213> ORGANISM: Homo sapiens

<400> SEQUENCE: 87
cuacaugugu aacaguucc                                                19

<210> SEQ ID NO 88
<211> LENGTH: 19
<212> TYPE: RNA
<213> ORGANISM: Homo sapiens

<400> SEQUENCE: 88
aacuacaugu guaacaguu                                                19

<210> SEQ ID NO 89
<211> LENGTH: 19
<212> TYPE: RNA
<213> ORGANISM: Homo sapiens

<400> SEQUENCE: 89
caacuacaug uguaacagu                                                19

<210> SEQ ID NO 90
<211> LENGTH: 19
<212> TYPE: RNA
<213> ORGANISM: Homo sapiens

<400> SEQUENCE: 90
cacuacaacu acaugugua                                                19

<210> SEQ ID NO 91
<211> LENGTH: 19
<212> TYPE: RNA
<213> ORGANISM: Homo sapiens

<400> SEQUENCE: 91
ccacuacaac uacaugugu                                                19

<210> SEQ ID NO 92
<211> LENGTH: 19
<212> TYPE: RNA
<213> ORGANISM: Homo sapiens

<400> SEQUENCE: 92
gacagaaaca cuuuucgac                                                19

<210> SEQ ID NO 93
<211> LENGTH: 19
<212> TYPE: RNA

<213> ORGANISM: Homo sapiens

<400> SEQUENCE: 93
ggagaauauu ucacccuuc                                                19

<210> SEQ ID NO 94
<211> LENGTH: 19
<212> TYPE: RNA
<213> ORGANISM: Homo sapiens

<400> SEQUENCE: 94
guguaacagu uccugcaug                                                19

<210> SEQ ID NO 95
<211> LENGTH: 19
<212> TYPE: RNA
<213> ORGANISM: Homo sapiens

<400> SEQUENCE: 95
acaacuacau guguaacag                                                19

<210> SEQ ID NO 96
<211> LENGTH: 19
<212> TYPE: RNA
<213> ORGANISM: Homo sapiens

<400> SEQUENCE: 96
acuacaacua cauguguaa                                                19

<210> SEQ ID NO 97
<211> LENGTH: 19
<212> TYPE: RNA
<213> ORGANISM: Homo sapiens

<400> SEQUENCE: 97
accauccacu acaacuaca                                                19

<210> SEQ ID NO 98
<211> LENGTH: 19
<212> TYPE: RNA
<213> ORGANISM: Homo sapiens

<400> SEQUENCE: 98
accaccaucc acuacaacu                                                19

<210> SEQ ID NO 99
<211> LENGTH: 19
<212> TYPE: RNA
<213> ORGANISM: Homo sapiens

<400> SEQUENCE: 99
uaccaccauc cacuacaac                                                19

<210> SEQ ID NO 100
<211> LENGTH: 19
<212> TYPE: RNA
<213> ORGANISM: Homo sapiens

<400> SEQUENCE: 100
acagaaacac uuuucgaca                                                19

<210> SEQ ID NO 101
<211> LENGTH: 19
<212> TYPE: RNA

<213> ORGANISM: Homo sapiens

<400> SEQUENCE: 101
gaguggaagg aaauuugcg                                                19

<210> SEQ ID NO 102
<211> LENGTH: 19
<212> TYPE: RNA
<213> ORGANISM: Homo sapiens

<400> SEQUENCE: 102
auauuucacc cuucagauc                                                19

<210> SEQ ID NO 103
<211> LENGTH: 19
<212> TYPE: RNA
<213> ORGANISM: Homo sapiens

<400> SEQUENCE: 103
aauauuucac ccuucagau                                                19

<210> SEQ ID NO 104
<211> LENGTH: 19
<212> TYPE: RNA
<213> ORGANISM: Homo sapiens

<400> SEQUENCE: 104
agaauauuuc acccuucag                                                19

<210> SEQ ID NO 105
<211> LENGTH: 19
<212> TYPE: RNA
<213> ORGANISM: Homo sapiens

<400> SEQUENCE: 105
uggagaauau uucacccuu                                                19

<210> SEQ ID NO 106
<211> LENGTH: 19
<212> TYPE: RNA
<213> ORGANISM: Homo sapiens

<400> SEQUENCE: 106
acauguguaa caguuccug                                                19

<210> SEQ ID NO 107
<211> LENGTH: 19
<212> TYPE: RNA
<213> ORGANISM: Homo sapiens

<400> SEQUENCE: 107
uacaacuaca uguguaaca                                                19

<210> SEQ ID NO 108
<211> LENGTH: 19
<212> TYPE: RNA
<213> ORGANISM: Homo sapiens

<400> SEQUENCE: 108
cuacaacuac auguguaac                                                19

<210> SEQ ID NO 109
<211> LENGTH: 19
<212> TYPE: RNA

<213> ORGANISM: Homo sapiens

<400> SEQUENCE: 109
uccacuacaa cuacaugug            19

<210> SEQ ID NO 110
<211> LENGTH: 19
<212> TYPE: RNA
<213> ORGANISM: Homo sapiens

<400> SEQUENCE: 110
auccacuaca acuacaugu            19

<210> SEQ ID NO 111
<211> LENGTH: 19
<212> TYPE: RNA
<213> ORGANISM: Homo sapiens

<400> SEQUENCE: 111
cauccacuac aacuacaug            19

<210> SEQ ID NO 112
<211> LENGTH: 19
<212> TYPE: RNA
<213> ORGANISM: Homo sapiens

<400> SEQUENCE: 112
caccauccac uacaacuac            19

<210> SEQ ID NO 113
<211> LENGTH: 19
<212> TYPE: RNA
<213> ORGANISM: Homo sapiens

<400> SEQUENCE: 113
uguguaacag uuccugcau            19

<210> SEQ ID NO 114
<211> LENGTH: 19
<212> TYPE: RNA
<213> ORGANISM: Homo sapiens

<400> SEQUENCE: 114
cauguguaac aguuccugc            19

<210> SEQ ID NO 115
<211> LENGTH: 19
<212> TYPE: RNA
<213> ORGANISM: Homo sapiens

<400> SEQUENCE: 115
uacaugugua acaguuccu            19

<210> SEQ ID NO 116
<211> LENGTH: 19
<212> TYPE: RNA
<213> ORGANISM: Homo sapiens

<400> SEQUENCE: 116
acuacaugug uaacaguuc            19

<210> SEQ ID NO 117
<211> LENGTH: 19
<212> TYPE: RNA

<213> ORGANISM: Homo sapiens

<400> SEQUENCE: 117
auccgagugg aaggaaauu                                              19

<210> SEQ ID NO 118
<211> LENGTH: 19
<212> TYPE: RNA
<213> ORGANISM: Homo sapiens

<400> SEQUENCE: 118
ucacuccagc caccugaag                                              19

<210> SEQ ID NO 119
<211> LENGTH: 19
<212> TYPE: RNA
<213> ORGANISM: Homo sapiens

<400> SEQUENCE: 119
cucacuccag ccaccugaa                                              19

<210> SEQ ID NO 120
<211> LENGTH: 19
<212> TYPE: RNA
<213> ORGANISM: Homo sapiens

<400> SEQUENCE: 120
uuguagugga uggugguac                                              19

<210> SEQ ID NO 121
<211> LENGTH: 19
<212> TYPE: RNA
<213> ORGANISM: Homo sapiens

<400> SEQUENCE: 121
uuuucaggaa guaguuucc                                              19

<210> SEQ ID NO 122
<211> LENGTH: 19
<212> TYPE: RNA
<213> ORGANISM: Homo sapiens

<400> SEQUENCE: 122
uagauuacca cuggagucu                                              19

<210> SEQ ID NO 123
<211> LENGTH: 19
<212> TYPE: RNA
<213> ORGANISM: Homo sapiens

<400> SEQUENCE: 123
auguaguugu aguggaugg                                              19

<210> SEQ ID NO 124
<211> LENGTH: 19
<212> TYPE: RNA
<213> ORGANISM: Homo sapiens

<400> SEQUENCE: 124
uaguuguagu ggauggugg                                              19

<210> SEQ ID NO 125
<211> LENGTH: 19
<212> TYPE: RNA

<213> ORGANISM: Homo sapiens

<400> SEQUENCE: 125
acuaugucga aaaguguuu                                                19

<210> SEQ ID NO 126
<211> LENGTH: 19
<212> TYPE: RNA
<213> ORGANISM: Homo sapiens

<400> SEQUENCE: 126
uaucugagca gcgcucaug                                                19

<210> SEQ ID NO 127
<211> LENGTH: 19
<212> TYPE: RNA
<213> ORGANISM: Homo sapiens

<400> SEQUENCE: 127
ugcuuguaga uggccaugg                                                19

<210> SEQ ID NO 128
<211> LENGTH: 19
<212> TYPE: RNA
<213> ORGANISM: Homo sapiens

<400> SEQUENCE: 128
gugcaaguca cagacuugg                                                19

<210> SEQ ID NO 129
<211> LENGTH: 19
<212> TYPE: RNA
<213> ORGANISM: Homo sapiens

<400> SEQUENCE: 129
uuuuuuggca gcaaaguuu                                                19

<210> SEQ ID NO 130
<211> LENGTH: 19
<212> TYPE: RNA
<213> ORGANISM: Homo sapiens

<400> SEQUENCE: 130
uaaaaaggga gaaggaggg                                                19

<210> SEQ ID NO 131
<211> LENGTH: 19
<212> TYPE: RNA
<213> ORGANISM: Homo sapiens

<400> SEQUENCE: 131
aaaaugcaga ugugcuugc                                                19

<210> SEQ ID NO 132
<211> LENGTH: 19
<212> TYPE: RNA
<213> ORGANISM: Homo sapiens

<400> SEQUENCE: 132
auguaaaaga uguugaccc                                                19

<210> SEQ ID NO 133
<211> LENGTH: 19
<212> TYPE: RNA

<213> ORGANISM: Homo sapiens

<400> SEQUENCE: 133
uaaaagaugu ugacccuuc                                                19

<210> SEQ ID NO 134
<211> LENGTH: 19
<212> TYPE: RNA
<213> ORGANISM: Homo sapiens

<400> SEQUENCE: 134
aagauguuga cccuuccag                                                19

<210> SEQ ID NO 135
<211> LENGTH: 19
<212> TYPE: RNA
<213> ORGANISM: Homo sapiens

<400> SEQUENCE: 135
uguaauccca gcacucugg                                                19

<210> SEQ ID NO 136
<211> LENGTH: 19
<212> TYPE: RNA
<213> ORGANISM: Homo sapiens

<400> SEQUENCE: 136
aacacuguga gaccccauc                                                19

<210> SEQ ID NO 137
<211> LENGTH: 19
<212> TYPE: RNA
<213> ORGANISM: Homo sapiens

<400> SEQUENCE: 137
aaaacaugca aaaguuggc                                                19

<210> SEQ ID NO 138
<211> LENGTH: 19
<212> TYPE: RNA
<213> ORGANISM: Homo sapiens

<400> SEQUENCE: 138
aaaaguuggc uggccaugg                                                19

<210> SEQ ID NO 139
<211> LENGTH: 19
<212> TYPE: RNA
<213> ORGANISM: Homo sapiens

<400> SEQUENCE: 139
uucaucugga ccuggucu                                                 19

<210> SEQ ID NO 140
<211> LENGTH: 19
<212> TYPE: RNA
<213> ORGANISM: Homo sapiens

<400> SEQUENCE: 140
ucuuccagug ugaugaugg                                                19

<210> SEQ ID NO 141
<211> LENGTH: 19
<212> TYPE: RNA

<213> ORGANISM: Homo sapiens

<400> SEQUENCE: 141
ggagucuucc agugugaug                                                  19

<210> SEQ ID NO 142
<211> LENGTH: 19
<212> TYPE: RNA
<213> ORGANISM: Homo sapiens

<400> SEQUENCE: 142
gucuuccagu gugaugaug                                                  19

<210> SEQ ID NO 143
<211> LENGTH: 19
<212> TYPE: RNA
<213> ORGANISM: Homo sapiens

<400> SEQUENCE: 143
cuuccagugu gaugauggu                                                  19

<210> SEQ ID NO 144
<211> LENGTH: 19
<212> TYPE: RNA
<213> ORGANISM: Homo sapiens

<400> SEQUENCE: 144
agucuuccag ugugaugau                                                  19

<210> SEQ ID NO 145
<211> LENGTH: 19
<212> TYPE: RNA
<213> ORGANISM: Homo sapiens

<400> SEQUENCE: 145
ccacuggagu cuuccagug                                                  19

<210> SEQ ID NO 146
<211> LENGTH: 19
<212> TYPE: RNA
<213> ORGANISM: Homo sapiens

<400> SEQUENCE: 146
cacuggaguc uuccagugu                                                  19

<210> SEQ ID NO 147
<211> LENGTH: 19
<212> TYPE: RNA
<213> ORGANISM: Homo sapiens

<400> SEQUENCE: 147
cuggagucuu ccaguguga                                                  19

<210> SEQ ID NO 148
<211> LENGTH: 19
<212> TYPE: RNA
<213> ORGANISM: Homo sapiens

<400> SEQUENCE: 148
uggagucuuc cagugugau                                                  19

<210> SEQ ID NO 149
<211> LENGTH: 19
<212> TYPE: RNA

<213> ORGANISM: Homo sapiens

<400> SEQUENCE: 149
accuccguca ugugcugug                                           19

<210> SEQ ID NO 150
<211> LENGTH: 19
<212> TYPE: RNA
<213> ORGANISM: Homo sapiens

<400> SEQUENCE: 150
ccacuggagu cuuccagug                                           19

<210> SEQ ID NO 151
<211> LENGTH: 19
<212> TYPE: RNA
<213> ORGANISM: Homo sapiens

<400> SEQUENCE: 151
ccuccgucau gugcuguga                                           19

<210> SEQ ID NO 152
<211> LENGTH: 19
<212> TYPE: RNA
<213> ORGANISM: Homo sapiens

<400> SEQUENCE: 152
cuccgucaug ugcugugac                                           19

<210> SEQ ID NO 153
<211> LENGTH: 19
<212> TYPE: RNA
<213> ORGANISM: Homo sapiens

<400> SEQUENCE: 153
auguaguugu aguggaugg                                           19

<210> SEQ ID NO 154
<211> LENGTH: 19
<212> TYPE: RNA
<213> ORGANISM: Homo sapiens

<400> SEQUENCE: 154
uaguuguagu ggauggugg                                           19

<210> SEQ ID NO 155
<211> LENGTH: 19
<212> TYPE: RNA
<213> ORGANISM: Homo sapiens

<400> SEQUENCE: 155
ucugaagggu gaaauauuc                                           19

<210> SEQ ID NO 156
<211> LENGTH: 19
<212> TYPE: RNA
<213> ORGANISM: Homo sapiens

<400> SEQUENCE: 156
gcaaauuucc uuccacucg                                           19

<210> SEQ ID NO 157
<211> LENGTH: 19
<212> TYPE: RNA

-continued

<213> ORGANISM: Homo sapiens

<400> SEQUENCE: 157
ugaaggguga aauauucuc                                      19

<210> SEQ ID NO 158
<211> LENGTH: 19
<212> TYPE: RNA
<213> ORGANISM: Homo sapiens

<400> SEQUENCE: 158
ggaacuguua cacauguag                                      19

<210> SEQ ID NO 159
<211> LENGTH: 19
<212> TYPE: RNA
<213> ORGANISM: Homo sapiens

<400> SEQUENCE: 159
aacuguuaca cauguaguu                                      19

<210> SEQ ID NO 160
<211> LENGTH: 19
<212> TYPE: RNA
<213> ORGANISM: Homo sapiens

<400> SEQUENCE: 160
acuguuacac auguaguug                                      19

<210> SEQ ID NO 161
<211> LENGTH: 19
<212> TYPE: RNA
<213> ORGANISM: Homo sapiens

<400> SEQUENCE: 161
uacacaugua guuguagug                                      19

<210> SEQ ID NO 162
<211> LENGTH: 19
<212> TYPE: RNA
<213> ORGANISM: Homo sapiens

<400> SEQUENCE: 162
acacauguag uuguagugg                                      19

<210> SEQ ID NO 163
<211> LENGTH: 19
<212> TYPE: RNA
<213> ORGANISM: Homo sapiens

<400> SEQUENCE: 163
gucgaaaagu guuucuguc                                      19

<210> SEQ ID NO 164
<211> LENGTH: 19
<212> TYPE: RNA
<213> ORGANISM: Homo sapiens

<400> SEQUENCE: 164
gaagggugaa auauucucc                                      19

<210> SEQ ID NO 165
<211> LENGTH: 19
<212> TYPE: RNA

<213> ORGANISM: Homo sapiens

<400> SEQUENCE: 165
caugcaggaa cguuuacac                                                19

<210> SEQ ID NO 166
<211> LENGTH: 19
<212> TYPE: RNA
<213> ORGANISM: Homo sapiens

<400> SEQUENCE: 166
cguuuacaca uguaguugu                                                19

<210> SEQ ID NO 167
<211> LENGTH: 19
<212> TYPE: RNA
<213> ORGANISM: Homo sapiens

<400> SEQUENCE: 167
uuacacaugu aguuguagu                                                19

<210> SEQ ID NO 168
<211> LENGTH: 19
<212> TYPE: RNA
<213> ORGANISM: Homo sapiens

<400> SEQUENCE: 168
uguaguugua guggauggu                                                19

<210> SEQ ID NO 169
<211> LENGTH: 19
<212> TYPE: RNA
<213> ORGANISM: Homo sapiens

<400> SEQUENCE: 169
aguuguagug gaugguggu                                                19

<210> SEQ ID NO 170
<211> LENGTH: 19
<212> TYPE: RNA
<213> ORGANISM: Homo sapiens

<400> SEQUENCE: 170
guuguagugg augguggua                                                19

<210> SEQ ID NO 171
<211> LENGTH: 19
<212> TYPE: RNA
<213> ORGANISM: Homo sapiens

<400> SEQUENCE: 171
ugucgaaaag uguuucugu                                                19

<210> SEQ ID NO 172
<211> LENGTH: 19
<212> TYPE: RNA
<213> ORGANISM: Homo sapiens

<400> SEQUENCE: 172
cgcaaauuuc cuuccacuc                                                19

<210> SEQ ID NO 173
<211> LENGTH: 19
<212> TYPE: RNA

<213> ORGANISM: Homo sapiens

<400> SEQUENCE: 173
gaucugaagg gugaaauau                                         19

<210> SEQ ID NO 174
<211> LENGTH: 19
<212> TYPE: RNA
<213> ORGANISM: Homo sapiens

<400> SEQUENCE: 174
aucugaaggg ugaaauauu                                         19

<210> SEQ ID NO 175
<211> LENGTH: 19
<212> TYPE: RNA
<213> ORGANISM: Homo sapiens

<400> SEQUENCE: 175
cugaagggug aaauauucu                                         19

<210> SEQ ID NO 176
<211> LENGTH: 19
<212> TYPE: RNA
<213> ORGANISM: Homo sapiens

<400> SEQUENCE: 176
aagggugaaa uauucucca                                         19

<210> SEQ ID NO 177
<211> LENGTH: 19
<212> TYPE: RNA
<213> ORGANISM: Homo sapiens

<400> SEQUENCE: 177
caggaacugu uacacaugu                                         19

<210> SEQ ID NO 178
<211> LENGTH: 19
<212> TYPE: RNA
<213> ORGANISM: Homo sapiens

<400> SEQUENCE: 178
uguuacacau guaguugua                                         19

<210> SEQ ID NO 179
<211> LENGTH: 19
<212> TYPE: RNA
<213> ORGANISM: Homo sapiens

<400> SEQUENCE: 179
guuacacaug uaguuguag                                         19

<210> SEQ ID NO 180
<211> LENGTH: 19
<212> TYPE: RNA
<213> ORGANISM: Homo sapiens

<400> SEQUENCE: 180
cacauguagu uguagugga                                         19

<210> SEQ ID NO 181
<211> LENGTH: 19
<212> TYPE: RNA

<213> ORGANISM: Homo sapiens

<400> SEQUENCE: 181
acauguaguu guaguggau                                                19

<210> SEQ ID NO 182
<211> LENGTH: 19
<212> TYPE: RNA
<213> ORGANISM: Homo sapiens

<400> SEQUENCE: 182
cauguaguug uaguggaug                                                19

<210> SEQ ID NO 183
<211> LENGTH: 19
<212> TYPE: RNA
<213> ORGANISM: Homo sapiens

<400> SEQUENCE: 183
guaguuguag uggauggug                                                19

<210> SEQ ID NO 184
<211> LENGTH: 19
<212> TYPE: RNA
<213> ORGANISM: Homo sapiens

<400> SEQUENCE: 184
augcaggaac uguuacaca                                                19

<210> SEQ ID NO 185
<211> LENGTH: 19
<212> TYPE: RNA
<213> ORGANISM: Homo sapiens

<400> SEQUENCE: 185
gcaggaacug uuacacaug                                                19

<210> SEQ ID NO 186
<211> LENGTH: 19
<212> TYPE: RNA
<213> ORGANISM: Homo sapiens

<400> SEQUENCE: 186
aggaacuguu acacaugua                                                19

<210> SEQ ID NO 187
<211> LENGTH: 19
<212> TYPE: RNA
<213> ORGANISM: Homo sapiens

<400> SEQUENCE: 187
gaacuguuac acauguagu                                                19

<210> SEQ ID NO 188
<211> LENGTH: 19
<212> TYPE: RNA
<213> ORGANISM: Homo sapiens

<400> SEQUENCE: 188 aauuccuuc cacucggau                                                 19

<210> SEQ ID NO 189
<211> LENGTH: 19
<212> TYPE: RNA

<213> ORGANISM: Homo sapiens

<400> SEQUENCE: 189
cuucaggugg cuggaguga                                                   19

<210> SEQ ID NO 190
<211> LENGTH: 19
<212> TYPE: RNA
<213> ORGANISM: Homo sapiens

<400> SEQUENCE: 190
uucagguggc uggagugag                                                   19

<210> SEQ ID NO 191
<211> LENGTH: 21
<212> TYPE: RNA
<213> ORGANISM: Homo sapiens

<400> SEQUENCE: 191
ggaagagaau cuccgcaaga a                                                21

<210> SEQ ID NO 192
<211> LENGTH: 21
<212> TYPE: RNA
<213> ORGANISM: Homo sapiens

<400> SEQUENCE: 192
guaccaccau ccacuacaac u                                                21

<210> SEQ ID NO 193
<211> LENGTH: 21
<212> TYPE: RNA
<213> ORGANISM: Homo sapiens

<400> SEQUENCE: 193
ggacgauauu gaacaauggu u                                                21

<210> SEQ ID NO 194
<211> LENGTH: 21
<212> TYPE: RNA
<213> ORGANISM: Homo sapiens

<400> SEQUENCE: 194
ccagccaccu gaaguccaaa a                                                21

<210> SEQ ID NO 195
<211> LENGTH: 21
<212> TYPE: RNA
<213> ORGANISM: Homo sapiens

<400> SEQUENCE: 195
gagaauauuu cacccuucag a                                                21

<210> SEQ ID NO 196
<211> LENGTH: 21
<212> TYPE: RNA
<213> ORGANISM: Homo sapiens

<400> SEQUENCE: 196
agaaaccacu ggauggagaa u                                                21

<210> SEQ ID NO 197
<211> LENGTH: 21
<212> TYPE: RNA

```
<213> ORGANISM: Homo sapiens

<400> SEQUENCE: 197
cuacugggac ggaacagcuu u                                              21

<210> SEQ ID NO 198
<211> LENGTH: 21
<212> TYPE: RNA
<213> ORGANISM: Homo sapiens

<400> SEQUENCE: 198
agacuccagu gguaaucuac u                                              21

<210> SEQ ID NO 199
<211> LENGTH: 21
<212> TYPE: RNA
<213> ORGANISM: Homo sapiens

<400> SEQUENCE: 199
cuggaagacu ccagugguaa u                                              21

<210> SEQ ID NO 200
<211> LENGTH: 21
<212> TYPE: RNA
<213> ORGANISM: Homo sapiens

<400> SEQUENCE: 200
gaaacuacuu ccugaaaaca a                                              21

<210> SEQ ID NO 201
<211> LENGTH: 21
<212> TYPE: RNA
<213> ORGANISM: Homo sapiens

<400> SEQUENCE: 201
ggaaacuacu uccugaaaac a                                              21

<210> SEQ ID NO 202
<211> LENGTH: 21
<212> TYPE: RNA
<213> ORGANISM: Homo sapiens

<400> SEQUENCE: 202
aaacacuuuu cgacauagug u                                              21

<210> SEQ ID NO 203
<211> LENGTH: 21
<212> TYPE: RNA
<213> ORGANISM: Homo sapiens

<400> SEQUENCE: 203
ggaguauuug gaugacagaa a                                              21

<210> SEQ ID NO 204
<211> LENGTH: 21
<212> TYPE: RNA
<213> ORGANISM: Homo sapiens

<400> SEQUENCE: 204
ucagaccuau ggaaacuacu u                                              21

<210> SEQ ID NO 205
<211> LENGTH: 21
<212> TYPE: RNA
```

-continued

<213> ORGANISM: Homo sapiens

<400> SEQUENCE: 205
ccauggccau cuacaagcag u                                        21

<210> SEQ ID NO 206
<211> LENGTH: 21
<212> TYPE: RNA
<213> ORGANISM: Homo sapiens

<400> SEQUENCE: 206
ccaagucugu gacuugcacg u                                        21

<210> SEQ ID NO 207
<211> LENGTH: 21
<212> TYPE: RNA
<213> ORGANISM: Homo sapiens

<400> SEQUENCE: 207
ggacagccaa gucugugacu u                                        21

<210> SEQ ID NO 208
<211> LENGTH: 21
<212> TYPE: RNA
<213> ORGANISM: Homo sapiens

<400> SEQUENCE: 208
cccuccuucu cccuuuuuau a                                        21

<210> SEQ ID NO 209
<211> LENGTH: 21
<212> TYPE: RNA
<213> ORGANISM: Homo sapiens

<400> SEQUENCE: 209
ccauccacua caacuacaug u                                        21

<210> SEQ ID NO 210
<211> LENGTH: 21
<212> TYPE: RNA
<213> ORGANISM: Homo sapiens

<400> SEQUENCE: 210
ccaccaucca cuacaacuac a                                        21

<210> SEQ ID NO 211
<211> LENGTH: 21
<212> TYPE: RNA
<213> ORGANISM: Homo sapiens

<400> SEQUENCE: 211
gagaauauuu cacccuucag a                                        21

<210> SEQ ID NO 212
<211> LENGTH: 21
<212> TYPE: RNA
<213> ORGANISM: Homo sapiens

<400> SEQUENCE: 212
ggagaauauu ucacccuuca g                                        21

<210> SEQ ID NO 213
<211> LENGTH: 21
<212> TYPE: RNA

<213> ORGANISM: Homo sapiens

<400> SEQUENCE: 213
cuacaugugu aacaguuccu g    21

<210> SEQ ID NO 214
<211> LENGTH: 21
<212> TYPE: RNA
<213> ORGANISM: Homo sapiens

<400> SEQUENCE: 214
acaacuacau guguaacagu u    21

<210> SEQ ID NO 215
<211> LENGTH: 21
<212> TYPE: RNA
<213> ORGANISM: Homo sapiens

<400> SEQUENCE: 215
ccacuacaac uacaugugua a    21

<210> SEQ ID NO 216
<211> LENGTH: 21
<212> TYPE: RNA
<213> ORGANISM: Homo sapiens

<400> SEQUENCE: 216
caccauccac uacaacuaca u    21

<210> SEQ ID NO 217
<211> LENGTH: 21
<212> TYPE: RNA
<213> ORGANISM: Homo sapiens

<400> SEQUENCE: 217
gaauauuuca cccuucagau c    21

<210> SEQ ID NO 218
<211> LENGTH: 21
<212> TYPE: RNA
<213> ORGANISM: Homo sapiens

<400> SEQUENCE: 218
agaauauuuc acccuucaga u    21

<210> SEQ ID NO 219
<211> LENGTH: 21
<212> TYPE: RNA
<213> ORGANISM: Homo sapiens

<400> SEQUENCE: 219
uaccaccauc cacuacaacu a    21

<210> SEQ ID NO 220
<211> LENGTH: 21
<212> TYPE: RNA
<213> ORGANISM: Homo sapiens

<400> SEQUENCE: 220
gauggagaau auuucacccu u    21

<210> SEQ ID NO 221
<211> LENGTH: 21
<212> TYPE: RNA

<213> ORGANISM: Homo sapiens

<400> SEQUENCE: 221
ccgaguggaa ggaaauuugc g                                              21

<210> SEQ ID NO 222
<211> LENGTH: 21
<212> TYPE: RNA
<213> ORGANISM: Homo sapiens

<400> SEQUENCE: 222
aacuacaugu guaacaguuc c                                              21

<210> SEQ ID NO 223
<211> LENGTH: 21
<212> TYPE: RNA
<213> ORGANISM: Homo sapiens

<400> SEQUENCE: 223
caacuacaug uguaacaguu c                                              21

<210> SEQ ID NO 224
<211> LENGTH: 21
<212> TYPE: RNA
<213> ORGANISM: Homo sapiens

<400> SEQUENCE: 224
acuacaacua cauguguaac a                                              21

<210> SEQ ID NO 225
<211> LENGTH: 21
<212> TYPE: RNA
<213> ORGANISM: Homo sapiens

<400> SEQUENCE: 225
cacuacaacu acauguguaa c                                              21

<210> SEQ ID NO 226
<211> LENGTH: 21
<212> TYPE: RNA
<213> ORGANISM: Homo sapiens

<400> SEQUENCE: 226
uccacuacaa cuacaugugu a                                              21

<210> SEQ ID NO 227
<211> LENGTH: 21
<212> TYPE: RNA
<213> ORGANISM: Homo sapiens

<400> SEQUENCE: 227
cauccacuac aacuacaugu g                                              21

<210> SEQ ID NO 228
<211> LENGTH: 21
<212> TYPE: RNA
<213> ORGANISM: Homo sapiens

<400> SEQUENCE: 228
accauccacu acaacuacau g                                              21

<210> SEQ ID NO 229
<211> LENGTH: 21
<212> TYPE: RNA

<213> ORGANISM: Homo sapiens

<400> SEQUENCE: 229
uggagaauau uucacccuuc a                                           21

<210> SEQ ID NO 230
<211> LENGTH: 21
<212> TYPE: RNA
<213> ORGANISM: Homo sapiens

<400> SEQUENCE: 230
auguguaaca guuccugcau g                                           21

<210> SEQ ID NO 231
<211> LENGTH: 21
<212> TYPE: RNA
<213> ORGANISM: Homo sapiens

<400> SEQUENCE: 231
cauguguaac aguuccugca u                                           21

<210> SEQ ID NO 232
<211> LENGTH: 21
<212> TYPE: RNA
<213> ORGANISM: Homo sapiens

<400> SEQUENCE: 232
uacaacuaca uguguaacag u                                           21

<210> SEQ ID NO 233
<211> LENGTH: 21
<212> TYPE: RNA
<213> ORGANISM: Homo sapiens

<400> SEQUENCE: 233
cuacaacuac auguguaaca g                                           21

<210> SEQ ID NO 234
<211> LENGTH: 21
<212> TYPE: RNA
<213> ORGANISM: Homo sapiens

<400> SEQUENCE: 234
auccacuaca acuacaugug u                                           21

<210> SEQ ID NO 235
<211> LENGTH: 21
<212> TYPE: RNA
<213> ORGANISM: Homo sapiens

<400> SEQUENCE: 235
accaccaucc acuacaacua c                                           21

<210> SEQ ID NO 236
<211> LENGTH: 21
<212> TYPE: RNA
<213> ORGANISM: Homo sapiens

<400> SEQUENCE: 236
aauauuucac ccuucagauc c                                           21

<210> SEQ ID NO 237
<211> LENGTH: 21
<212> TYPE: RNA

<213> ORGANISM: Homo sapiens

<400> SEQUENCE: 237
acuacaugug uaacaguucc u           21

<210> SEQ ID NO 238
<211> LENGTH: 21
<212> TYPE: RNA
<213> ORGANISM: Homo sapiens

<400> SEQUENCE: 238
auggagaaua uuucacccuu c           21

<210> SEQ ID NO 239
<211> LENGTH: 21
<212> TYPE: RNA
<213> ORGANISM: Homo sapiens

<400> SEQUENCE: 239
uguguaacag uuccugcaug g           21

<210> SEQ ID NO 240
<211> LENGTH: 21
<212> TYPE: RNA
<213> ORGANISM: Homo sapiens

<400> SEQUENCE: 240
uccgagugga aggaaauuug c           21

<210> SEQ ID NO 241
<211> LENGTH: 21
<212> TYPE: RNA
<213> ORGANISM: Homo sapiens

<400> SEQUENCE: 241
auccgagugg aaggaaauuu g           21

<210> SEQ ID NO 242
<211> LENGTH: 21
<212> TYPE: RNA
<213> ORGANISM: Homo sapiens

<400> SEQUENCE: 242
ucacacugga agacuccagu g           21

<210> SEQ ID NO 243
<211> LENGTH: 21
<212> TYPE: RNA
<213> ORGANISM: Homo sapiens

<400> SEQUENCE: 243
aucacacugg aagacuccag u           21

<210> SEQ ID NO 244
<211> LENGTH: 21
<212> TYPE: RNA
<213> ORGANISM: Homo sapiens

<400> SEQUENCE: 244
cacacuggaa gacuccagug g           21

<210> SEQ ID NO 245
<211> LENGTH: 21
<212> TYPE: RNA

<213> ORGANISM: Homo sapiens

<400> SEQUENCE: 245
ucaucacacu ggaagacucc a    21

<210> SEQ ID NO 246
<211> LENGTH: 21
<212> TYPE: RNA
<213> ORGANISM: Homo sapiens

<400> SEQUENCE: 246
ccaucaucac acuggaagac u    21

<210> SEQ ID NO 247
<211> LENGTH: 21
<212> TYPE: RNA
<213> ORGANISM: Homo sapiens

<400> SEQUENCE: 247
caucacacug gaagacucca g    21

<210> SEQ ID NO 248
<211> LENGTH: 21
<212> TYPE: RNA
<213> ORGANISM: Homo sapiens

<400> SEQUENCE: 248
caucaucaca cuggaagacu c    21

<210> SEQ ID NO 249
<211> LENGTH: 21
<212> TYPE: RNA
<213> ORGANISM: Homo sapiens

<400> SEQUENCE: 249
accaucauca cacuggaaga c    21

<210> SEQ ID NO 250
<211> LENGTH: 21
<212> TYPE: RNA
<213> ORGANISM: Homo sapiens

<400> SEQUENCE: 250
ucacacugga agacuccagu g    21

<210> SEQ ID NO 251
<211> LENGTH: 21
<212> TYPE: RNA
<213> ORGANISM: Homo sapiens

<400> SEQUENCE: 251
aucacacugg aagacuccag u    21

<210> SEQ ID NO 252
<211> LENGTH: 21
<212> TYPE: RNA
<213> ORGANISM: Homo sapiens

<400> SEQUENCE: 252
aucaucacac uggaagacuc c    21

<210> SEQ ID NO 253
<211> LENGTH: 21
<212> TYPE: RNA

<213> ORGANISM: Homo sapiens

<400> SEQUENCE: 253
cacacuggaa gacuccagug g     21

<210> SEQ ID NO 254
<211> LENGTH: 21
<212> TYPE: RNA
<213> ORGANISM: Homo sapiens

<400> SEQUENCE: 254
uucuugcgga gauucucuuc c     21

<210> SEQ ID NO 255
<211> LENGTH: 21
<212> TYPE: RNA
<213> ORGANISM: Homo sapiens

<400> SEQUENCE: 255
aguuguagug gaugguggua c     21

<210> SEQ ID NO 256
<211> LENGTH: 21
<212> TYPE: RNA
<213> ORGANISM: Homo sapiens

<400> SEQUENCE: 256
aaccauuguu caauaucguc c     21

<210> SEQ ID NO 257
<211> LENGTH: 21
<212> TYPE: RNA
<213> ORGANISM: Homo sapiens

<400> SEQUENCE: 257
uuuuggacuu cagguggcug g     21

<210> SEQ ID NO 258
<211> LENGTH: 21
<212> TYPE: RNA
<213> ORGANISM: Homo sapiens

<400> SEQUENCE: 258
ucugaagggu gaaauauucu c     21

<210> SEQ ID NO 259
<211> LENGTH: 21
<212> TYPE: RNA
<213> ORGANISM: Homo sapiens

<400> SEQUENCE: 259
auucuccauc cagugguuuc u     21

<210> SEQ ID NO 260
<211> LENGTH: 21
<212> TYPE: RNA
<213> ORGANISM: Homo sapiens

<400> SEQUENCE: 260
aaagcuguuc cgucccagua g     21

<210> SEQ ID NO 261
<211> LENGTH: 21
<212> TYPE: RNA

<213> ORGANISM: Homo sapiens

<400> SEQUENCE: 261
aguagauuac cacuggaguc u                                    21

<210> SEQ ID NO 262
<211> LENGTH: 21
<212> TYPE: RNA
<213> ORGANISM: Homo sapiens

<400> SEQUENCE: 262
auuaccacug gagucuucca g                                    21

<210> SEQ ID NO 263
<211> LENGTH: 21
<212> TYPE: RNA
<213> ORGANISM: Homo sapiens

<400> SEQUENCE: 263
uuguuuucag gaaguaguuu c                                    21

<210> SEQ ID NO 264
<211> LENGTH: 21
<212> TYPE: RNA
<213> ORGANISM: Homo sapiens

<400> SEQUENCE: 264
uguuuucagg aaguaguuuc c                                    21

<210> SEQ ID NO 265
<211> LENGTH: 21
<212> TYPE: RNA
<213> ORGANISM: Homo sapiens

<400> SEQUENCE: 265
acacuauguc gaaaaguguu u                                    21

<210> SEQ ID NO 266
<211> LENGTH: 21
<212> TYPE: RNA
<213> ORGANISM: Homo sapiens

<400> SEQUENCE: 266
uuucugucau ccaaauacuc c                                    21

<210> SEQ ID NO 267
<211> LENGTH: 21
<212> TYPE: RNA
<213> ORGANISM: Homo sapiens

<400> SEQUENCE: 267
aaguaguuuc cauaggucug a                                    21

<210> SEQ ID NO 268
<211> LENGTH: 21
<212> TYPE: RNA
<213> ORGANISM: Homo sapiens

<400> SEQUENCE: 268
acugcuugua gauggccaug g                                    21

<210> SEQ ID NO 269
<211> LENGTH: 21
<212> TYPE: RNA

<213> ORGANISM: Homo sapiens

<400> SEQUENCE: 269
acgugcaagu cacagacuug g          21

<210> SEQ ID NO 270
<211> LENGTH: 21
<212> TYPE: RNA
<213> ORGANISM: Homo sapiens

<400> SEQUENCE: 270
aagucacaga cuuggcuguc c          21

<210> SEQ ID NO 271
<211> LENGTH: 21
<212> TYPE: RNA
<213> ORGANISM: Homo sapiens

<400> SEQUENCE: 271
uauaaaaagg gagaaggagg g          21

<210> SEQ ID NO 272
<211> LENGTH: 21
<212> TYPE: RNA
<213> ORGANISM: Homo sapiens

<400> SEQUENCE: 272
acauguaguu guaguggaug g          21

<210> SEQ ID NO 273
<211> LENGTH: 21
<212> TYPE: RNA
<213> ORGANISM: Homo sapiens

<400> SEQUENCE: 273
uguaguugua guggauggug g          21

<210> SEQ ID NO 274
<211> LENGTH: 21
<212> TYPE: RNA
<213> ORGANISM: Homo sapiens

<400> SEQUENCE: 274
ucugaagggu gaaauauucu c          21

<210> SEQ ID NO 275
<211> LENGTH: 21
<212> TYPE: RNA
<213> ORGANISM: Homo sapiens

<400> SEQUENCE: 275
cugaagggug aaauauucuc c          21

<210> SEQ ID NO 276
<211> LENGTH: 21
<212> TYPE: RNA
<213> ORGANISM: Homo sapiens

<400> SEQUENCE: 276
caggaacugu uacacaugua g          21

<210> SEQ ID NO 277
<211> LENGTH: 21
<212> TYPE: RNA

<213> ORGANISM: Homo sapiens

<400> SEQUENCE: 277
aacuguuaca cauguaguug u                                              21

<210> SEQ ID NO 278
<211> LENGTH: 21
<212> TYPE: RNA
<213> ORGANISM: Homo sapiens

<400> SEQUENCE: 278
uuacacaugu aguuguagug g                                              21

<210> SEQ ID NO 279
<211> LENGTH: 21
<212> TYPE: RNA
<213> ORGANISM: Homo sapiens

<400> SEQUENCE: 279
auguaguugu aguggauggu g                                              21

<210> SEQ ID NO 280
<211> LENGTH: 21
<212> TYPE: RNA
<213> ORGANISM: Homo sapiens

<400> SEQUENCE: 280
gaucugaagg gugaaauauu c                                              21

<210> SEQ ID NO 281
<211> LENGTH: 21
<212> TYPE: RNA
<213> ORGANISM: Homo sapiens

<400> SEQUENCE: 281
aucugaaggg ugaaauauuc u                                              21

<210> SEQ ID NO 282
<211> LENGTH: 21
<212> TYPE: RNA
<213> ORGANISM: Homo sapiens

<400> SEQUENCE: 282
uaguuguagu ggaugguggu a                                              21

<210> SEQ ID NO 283
<211> LENGTH: 21
<212> TYPE: RNA
<213> ORGANISM: Homo sapiens

<400> SEQUENCE: 283
aagggugaaa uauucuccau c                                              21

<210> SEQ ID NO 284
<211> LENGTH: 21
<212> TYPE: RNA
<213> ORGANISM: Homo sapiens

<400> SEQUENCE: 284
cgcaaauuuc cuuccacucg g                                              21

<210> SEQ ID NO 285
<211> LENGTH: 21
<212> TYPE: RNA

<213> ORGANISM: Homo sapiens

<400> SEQUENCE: 285
ggaacuguua cacauguagu u                                              21

<210> SEQ ID NO 286
<211> LENGTH: 21
<212> TYPE: RNA
<213> ORGANISM: Homo sapiens

<400> SEQUENCE: 286
gaacuguuac acauguaguu g                                              21

<210> SEQ ID NO 287
<211> LENGTH: 21
<212> TYPE: RNA
<213> ORGANISM: Homo sapiens

<400> SEQUENCE: 287
uguuacacau guaguuguag u                                              21

<210> SEQ ID NO 288
<211> LENGTH: 21
<212> TYPE: RNA
<213> ORGANISM: Homo sapiens

<400> SEQUENCE: 288
guuacacaug uaguuguagu g                                              21

<210> SEQ ID NO 289
<211> LENGTH: 21
<212> TYPE: RNA
<213> ORGANISM: Homo sapiens

<400> SEQUENCE: 289
uacacaugua guuguagugg a                                              21

<210> SEQ ID NO 290
<211> LENGTH: 21
<212> TYPE: RNA
<213> ORGANISM: Homo sapiens

<400> SEQUENCE: 290
cacauguagu uguaguggau g                                              21

<210> SEQ ID NO 291
<211> LENGTH: 21
<212> TYPE: RNA
<213> ORGANISM: Homo sapiens

<400> SEQUENCE: 291
cauguaguug uaguggaugg u                                              21

<210> SEQ ID NO 292
<211> LENGTH: 21
<212> TYPE: RNA
<213> ORGANISM: Homo sapiens

<400> SEQUENCE: 292
ugaaggguga aauauucucc a                                              21

<210> SEQ ID NO 293
<211> LENGTH: 21
<212> TYPE: RNA

-continued

<213> ORGANISM: Homo sapiens

<400> SEQUENCE: 293
caugcaggaa cuguuacaca u                                              21

<210> SEQ ID NO 294
<211> LENGTH: 21
<212> TYPE: RNA
<213> ORGANISM: Homo sapiens

<400> SEQUENCE: 294
augcaggaac uguuacacau g                                              21

<210> SEQ ID NO 295
<211> LENGTH: 21
<212> TYPE: RNA
<213> ORGANISM: Homo sapiens

<400> SEQUENCE: 295
acuguuacac auguaguugu a                                              21

<210> SEQ ID NO 296
<211> LENGTH: 21
<212> TYPE: RNA
<213> ORGANISM: Homo sapiens

<400> SEQUENCE: 296
cuguuacaca uguaguugua g                                              21

<210> SEQ ID NO 297
<211> LENGTH: 21
<212> TYPE: RNA
<213> ORGANISM: Homo sapiens

<400> SEQUENCE: 297
acacauguag uuguagugga u                                              21

<210> SEQ ID NO 298
<211> LENGTH: 21
<212> TYPE: RNA
<213> ORGANISM: Homo sapiens

<400> SEQUENCE: 298
guaguuguag uggauggugg u                                              21

<210> SEQ ID NO 299
<211> LENGTH: 21
<212> TYPE: RNA
<213> ORGANISM: Homo sapiens

<400> SEQUENCE: 299
ggaucugaag ggugaaauau u                                              21

<210> SEQ ID NO 300
<211> LENGTH: 21
<212> TYPE: RNA
<213> ORGANISM: Homo sapiens

<400> SEQUENCE: 300
aggaacuguu acacauguag u                                              21

<210> SEQ ID NO 301
<211> LENGTH: 21
<212> TYPE: RNA

<213> ORGANISM: Homo sapiens

<400> SEQUENCE: 301
gaagggugaa auauucucca u　　　21

<210> SEQ ID NO 302
<211> LENGTH: 21
<212> TYPE: RNA
<213> ORGANISM: Homo sapiens

<400> SEQUENCE: 302
ccaugcagga acuguuacac a　　　21

<210> SEQ ID NO 303
<211> LENGTH: 21
<212> TYPE: RNA
<213> ORGANISM: Homo sapiens

<400> SEQUENCE: 303
gcaaauuccc uuccacucgg a　　　21

<210> SEQ ID NO 304
<211> LENGTH: 21
<212> TYPE: RNA
<213> ORGANISM: Homo sapiens

<400> SEQUENCE: 304
caaauucccu uccacucgga u　　　21

<210> SEQ ID NO 305
<211> LENGTH: 21
<212> TYPE: RNA
<213> ORGANISM: Homo sapiens

<400> SEQUENCE: 305
cacuggaguc uuccagugug a　　　21

<210> SEQ ID NO 306
<211> LENGTH: 21
<212> TYPE: RNA
<213> ORGANISM: Homo sapiens

<400> SEQUENCE: 306
acuggagucu uccaguguga u　　　21

<210> SEQ ID NO 307
<211> LENGTH: 21
<212> TYPE: RNA
<213> ORGANISM: Homo sapiens

<400> SEQUENCE: 307
ccacuggagu cuuccagugu g　　　21

<210> SEQ ID NO 308
<211> LENGTH: 21
<212> TYPE: RNA
<213> ORGANISM: Homo sapiens

<400> SEQUENCE: 308 uggagcuuc cagugugaug a　　　21

<210> SEQ ID NO 309
<211> LENGTH: 21
<212> TYPE: RNA

<213> ORGANISM: Homo sapiens

<400> SEQUENCE: 309
agucuuccag ugugaugaug g                                           21

<210> SEQ ID NO 310
<211> LENGTH: 21
<212> TYPE: RNA
<213> ORGANISM: Homo sapiens

<400> SEQUENCE: 310
cuggagucuu ccagugugau g                                           21

<210> SEQ ID NO 311
<211> LENGTH: 21
<212> TYPE: RNA
<213> ORGANISM: Homo sapiens

<400> SEQUENCE: 311
gagucuucca gugugaugau g                                           21

<210> SEQ ID NO 312
<211> LENGTH: 21
<212> TYPE: RNA
<213> ORGANISM: Homo sapiens

<400> SEQUENCE: 312
gucuuccagu gugaugaugg u                                           21

<210> SEQ ID NO 313
<211> LENGTH: 21
<212> TYPE: RNA
<213> ORGANISM: Homo sapiens

<400> SEQUENCE: 313
cacuggaguc uuccagugug a                                           21

<210> SEQ ID NO 314
<211> LENGTH: 21
<212> TYPE: RNA
<213> ORGANISM: Homo sapiens

<400> SEQUENCE: 314
acuggagucu uccaguguga u                                           21

<210> SEQ ID NO 315
<211> LENGTH: 21
<212> TYPE: RNA
<213> ORGANISM: Homo sapiens

<400> SEQUENCE: 315
ggagucuucc agugugauga u                                           21

<210> SEQ ID NO 316
<211> LENGTH: 21
<212> TYPE: RNA
<213> ORGANISM: Homo sapiens

<400> SEQUENCE: 316
ccacuggagu cuuccagugu g                                           21

OLIGORIBONUCLEOTIDES AND METHODS OF USE THEREOF FOR TREATMENT OF ALOPECIA, ACUTE RENAL FAILURE AND OTHER DISEASES

This application is a divisional of U.S. Ser. No. 11/237,598, filed Sep. 27, 2005, which claims the benefit of U.S. Provisional Applications Nos. 60/613,991, filed Sep. 28, 2004; 60/658,196, filed Mar. 2, 2005; and 60/703,020, filed Jul. 26, 2005, the contents of all of which are hereby incorporated by reference into this application.

Throughout this application various patent and scientific publications are cited. The disclosures for these publications in their entireties are hereby incorporated by reference into this application to more fully describe the state of the art to which this invention pertains.

BACKGROUND OF THE INVENTION siRNAs and RNA Interference

RNA interference (RNAi) is a phenomenon involving double-stranded (ds) RNA-dependent gene specific post-transcriptional silencing. Originally, attempts to study this phenomenon and to manipulate mammalian cells experimentally were frustrated by an active, non-specific antiviral defense mechanism which was activated in response to long dsRNA molecules; see Gil et al. 2000, Apoptosis, 5:107-114. Later it was discovered that synthetic duplexes of 21 nucleotide RNAs could mediate gene specific RNAi in mammalian cells, without the stimulation of the generic antiviral defence mechanisms (see Elbashir et al. Nature 2001, 411:494-498 and Caplen et al. Proc Natl Acad Sci 2001, 98:9742-9747). As a result, small interfering RNAs (siRNAs), which are short double-stranded RNAs, have become powerful tools in attempting to understand gene function.

Thus, RNA interference (RNAi) refers to the process of sequence-specific post-transcriptional gene silencing in mammals mediated by small interfering RNAs (siRNAs) (Fire et al, 1998, Nature 391, 806) or microRNAs (miRNAs) (Ambros V. Nature 431:7006, 350-355(2004); and Bartel D P. Cell. 2004 Jan. 23; 116(2): 281-97 *MicroRNAs: genomics, biogenesis, mechanism, and function*). The corresponding process in plants is commonly referred to as specific post-transcriptional gene silencing or RNA silencing and is also referred to as quelling in fungi. An siRNA is a double-stranded RNA molecule which down-regulates or silences (prevents) the expression of a gene/mRNA of its endogenous (cellular) counterpart. RNA interference is based on the ability of dsRNA species to enter a specific protein complex, where it is then targeted to the complementary cellular RNA and specifically degrades it. Thus, the RNA interference response features an endonuclease complex containing an siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir et al 2001, Genes Dev., 15, 188). In more detail, longer dsRNAs are digested into short (17-29 bp) dsRNA fragments (also referred to as short inhibitory RNAs—"siRNAs") by type III RNAses (DICER, DROSHA, etc., Bernstein et al., Nature, 2001, v. 409, p. 363-6; Lee et al., Nature, 2003, 425, p. 415-9). The RISC protein complex recognizes these fragments and complementary mRNA. The whole process is culminated by endonuclease cleavage of target mRNA (McManus & Sharp, Nature Rev Genet, 2002, v. 3, p. 737-47; Paddison & Hannon, Curr Opin Mol Ther. 2003 June; 5(3): 217-24). For information on these terms and proposed mechanisms, see Bernstein E., Denli A M. Hannon G J: 2001 *The rest is silence*. RNA. I; 7(11): 1509-21; Nishikura K.: 2001 *A short primer on RNAi: RNA-directed RNA polymerase acts as a key catalyst*. Cell. I 16; 107(4): 415-8 and PCT publication WO 01/36646 (Glover et al).

The selection and synthesis of siRNA corresponding to known genes has been widely reported; see for example Chalk A M, Wahlestedt C, Sonnhammer E L. 2004 *Improved and automated prediction of effective siRNA* Biochem. Biophys. Res. Commun. June 18; 319(1): 264-74; Sioud M, Leirdal M., 2004, *Potential design rules and enzymatic synthesis of siRNAs*, Methods Mol Biol.; 252:457-69; Levenkova N, Gu Q, Rux J J. 2004, *Gene specific siRNA selector* Bioinformatics. I 12; 20(3): 430-2. and Ui-Tei K, Naito Y, Takahashi F, Haraguchi T, Ohki-Hamazaki H, Juni A, Ueda R, Saigo K., *Guidelines for the selection of highly effective siRNA sequences for mammalian and chick RNA interference* Nucleic Acids Res. 2004 I 9; 32(3):936-48. Se also Liu Y, Braasch D A, Nulf C J, Corey D R. *Efficient and isoform-selective inhibition of cellular gene expression by peptide nucleic acids*, Biochemistry, 2004 I 24; 43(7):1921-7. See also PCT publications WO 2004/015107 (Atugen) and WO 02/44321 (Tuschl et al), and also Chiu Y L, Rana T M. *siRNA function in RNAi: a chemical modification analysis*, RNA 2003 September; 9(9):1034-48 and I U.S. Pat. Nos. 5,898,031 and 6,107,094 (Crooke) for production of modified/more stable siRNAs.

Several groups have described the development of DNA-based vectors capable of generating siRNA within cells. The method generally involves transcription of short hairpin RNAs that are efficiently processed to form siRNAs within cells. Paddison et al. *PNAS* 2002, 99:1443-1448; Paddison et al. *Genes & Dev* 2002, 16:948-958; Sui et al. *PNAS* 2002, 8:5515-5520; and Brummelkamp et al. *Science* 2002, 296: 550-553. These reports describe methods to generate siRNAs capable of specifically targeting numerous endogenously and exogenously expressed genes.

siRNA has recently been successfully used for inhibition in primates; for further details see Tolentino et al., Retina 24(1) February 2004 I 132-138.

The p53 Gene and Polypeptide

The human p53 gene is a well-known and highly studied gene. The p53 polypeptide plays a key role in cellular stress response mechanisms by converting a variety of different stimuli, for example DNA damaging conditions, such as gamma-irradiation, deregulation of transcription or replication, and oncogene transformation, into cell growth arrest or apoptosis (Gottlieb et al, 1996, Biochem. Biophys. Acta, 1287, p. 77). The p53 polypeptide is essential for the induction of programmed cell death or "apoptosis" as a response to such stimuli. Most anti-cancer therapies damage or kill also normal cells that contain native p53, causing severe side effects associated with the damage or death of healthy cells. Since such side effects are to a great extent determined by p53-mediated death of normal cells, the temporary suppression of p53 during the acute phase of anti-cancer therapy has been suggested as a therapeutic strategy to avoid these severe toxic events. This was described in U.S. Pat. No. 6,593,353 and in Komarov P G et al, 1999, *A chemical inhibitor of p53 that protects mice from the side effects of cancer therapy.*, Science, 285(5434):1651, 1653. p53 has been shown to be involved in chemotherapy and radiation-induced alopecia. (Botcharev et al, 2000, *p53 is essential for Chemotherapy—induced Hair Loss*, Cancer Research, 60, 5002-5006).

Alopecia

Recently there have been dramatic advances in the understanding of the molecules and pathways regulating hair follicle formation and hair growth. Chemotherapy disrupts the proliferation of matrix keratinocytes in the growth bulb that produce the hair shaft. This forces hair follicles to enter a dystrophic regression stage in which the integrity of the hair shaft is compromised and the hair then breaks and falls out. Because more than 90% of scalp follicles ire in growth stage at any one time, these hairs are rapidly lost after chemotherapy, and thus the alopecia is rapid and extensive (George Cotsarelis and Sarah E. Millar, 2001, *Towards a molecular understanding of hair loss and its treatment*, TRENDS in Molecular Medicine Vol. 7 No. 7). Chemotherapy drugs most likely to cause hair loss are: Cisplatinum, Cytarabine, Cyclophosphamide, Doxorubicin, Epirubicin, Etoposide, Ifosfamide and Vincristine. Radiation induced general alopecia is observed in virtually 100% of patients who receive whole brain radiation (WBR), particularly of 3000 rad and above.

Hair loss is one of the most feared side effects of chemotherapy among patients with cancer, even although hair lost following chemotherapy does eventually re-grow. From the patient's perspective, hair loss (alopecia) ranks second only to nausea as a distressing side effect of chemotherapy. About 75% of patients describe chemotherapy induced hair loss as equal to or more devastating than the pain caused by cancer.

Thus, although hair disorders are not life threatening, their profound impact on social interactions and on the psychological well-being of patients is undeniable. The demand for treatments for hair loss fuels a multi-billion dollar industry. Despite this, most currently marketed products are ineffective, evidenced by the fact that the FDA has approved only two treatments for hair loss. None of the known therapies or remedies is effective on cancer therapy-induced alopecia.

Acute Renal Failure (ARF).

ARF is a clinical syndrome characterized by rapid deterioration of renal function that occurs within days. The principal feature of ARF is an abrupt decline in glomerular filtration rate (GFR), resulting in the retention of nitrogenous wastes (urea, creatinine). In the general world population 170-200 cases of severe ARF per million population occur annually. To date, there is no specific treatment for established ARF. Several drugs have been found to ameliorate toxic and ischemic experimental ARF, as manifested by lower serum creatinine levels, reduced histological damage and faster recovery of renal function in different animal models. These include anti-oxidants, calcium channel blockers, diuretics, vasoactive substances, growth factors, anti-inflammatory agents and more. However, those drugs that have been studied in clinical trials showed no benefit, and their use in clinical ARF has not been approved.

In the majority of hospitalized patients, ARF is caused by acute tubular necrosis (ATN), which results from ischemic and/or nephrotoxic insults. Renal hypoperfusion is caused by hypovolemic, cardiogenic and septic shock, by administration of vasoconstrictive drugs or renovascular injury. Nephrotoxins include exogenous toxins such as contrast media and aminoglycosides as well as endogenous toxin such as myoglobin. Recent studies, however, support that apoptosis in renal tissues is prominent in most human cases of ARF. The principal site of apoptotic cell death is the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum. It has been suggested that apoptotic tubule cell death may be more predictive of functional changes than necrotic cell death (Komarov et al. Science. 1999 September 10; 285(5434): 1733-7); see also (Supavekin et al. Kidney Int. 2003 May; 63(5): 1714-24).

In conclusion, currently there are no satisfactory modes of therapy for the prevention and/or treatment of toxic alopecia and of acute renal failure, nor are there a satisfactory mode of therapy for many other diseases and disorders which are accompanied by an elevated level of p53 polypeptide, and there is a need therefore to develop novel compounds for this purpose.

SUMMARY OF THE INVENTION

The invention provides novel double stranded oligoribonucleotides that inhibit the p53 gene. The invention also provides a pharmaceutical composition comprising one or more such oligoribonucleotides, and a vector capable of expressing the oligoribonucleotide. The present invention also provides a method of treating a patient suffering from a disease in which temporary (reversible) inhibition of p53 activity is beneficial comprising administering to the patient one or more oligoribonucleotides typically as a pharmaceutical composition, in a therapeutically effective dose so as to thereby treat the patient. The present invention also contemplates treating other disorders which are accompanied by an elevated level of p53 polypeptide. Since long-term p53 inactivation can significantly increase the risk of cancer, it is preferred that the inhibition of p53 using the molecules of the present invention will be temporary.

In one preferred embodiment, the novel siRNA molecules disclosed herein may be used in the treatment of tumors in cases where temporary suppression of p53 using the p53 siRNA would be beneficial along with convential chemotherapy (as described herein) or radiotherapy. For example, the novel siRNA molecules disclosed herein would protect normal p53-containing cells from chemotherapy or radiotherapy-induced apoptosis. The novel siRNA molecules disclosed herein may also be used for inhibition of p53 expression in specific cancer cells in cases where p53 inhibition potentiates apoptotic cell death in these cells. Specifically, radiation therapy and chemotherapy may cause severe side effects, such as severe damage to the lymphoid and hematopoietic system and intestinal epithelia, which limit the effectiveness of these therapies, and may cause hair loss which causes psychological distress. These side effects are caused by p53-mediated apoptosis. Therefore, to eliminate or reduce adverse side effects associated with cancer treatment, it would be beneficial to induce temporary inhibition of p53 activity in normal cells using the siRNA molecules of the present invention, thereby protecting normal tissue.

In another preferred embodiment, the novel siRNA molecules disclosed herein may be used in the treatment of acute renal failure (ARF), which is characterized by rapid deterioration of renal function associated with apoptotic cell death in the renal tissue.

The novel siRNA molecules disclosed herein may also be used in other conditions in which p53 is activated as a consequence of a variety of stresses associated with injuries such as a burn, hyperthermia, hypoxia associated with a blocked blood supply such as in myocardial infraction, stroke, and ischemia. Temporary p53 inhibition using the siRNA molecules of the present invention can be therapeutically effective in reducing or eliminating p53-dependent neuronal death in the central nervous system, i.e., brain and spinal cord injury, the preservation of tissues and organs prior to transplanting, preparation of a host for a bone marrow transplant, and reducing or eliminating neuronal damage during a seizure.

p53 also plays a role in cell aging. In particular, morphological and physiological alterations of normal tissues associated with aging may be related to p53 activity. Senescent cells that accumulate in tissues over time are known to maintain very high levels of p53-dependent transcription. p53-dependent secretion of growth inhibitors by senescent cells accumulate in aging tissue. Thus, the siRNA molecules disclosed herein may also be used in suppression of tissue aging.

BRIEF DESCRIPTION OF THE FIGURES

FIG. 1. This figure represents the nucleotide sequence of the human p53 gene—SEQ ID No.: 1.

FIG. 2. This figure represents the amino acid sequence of the human p53 polypeptide—SEQ ID No. 2.

DETAILED DESCRIPTION OF THE INVENTION

Figure 3:
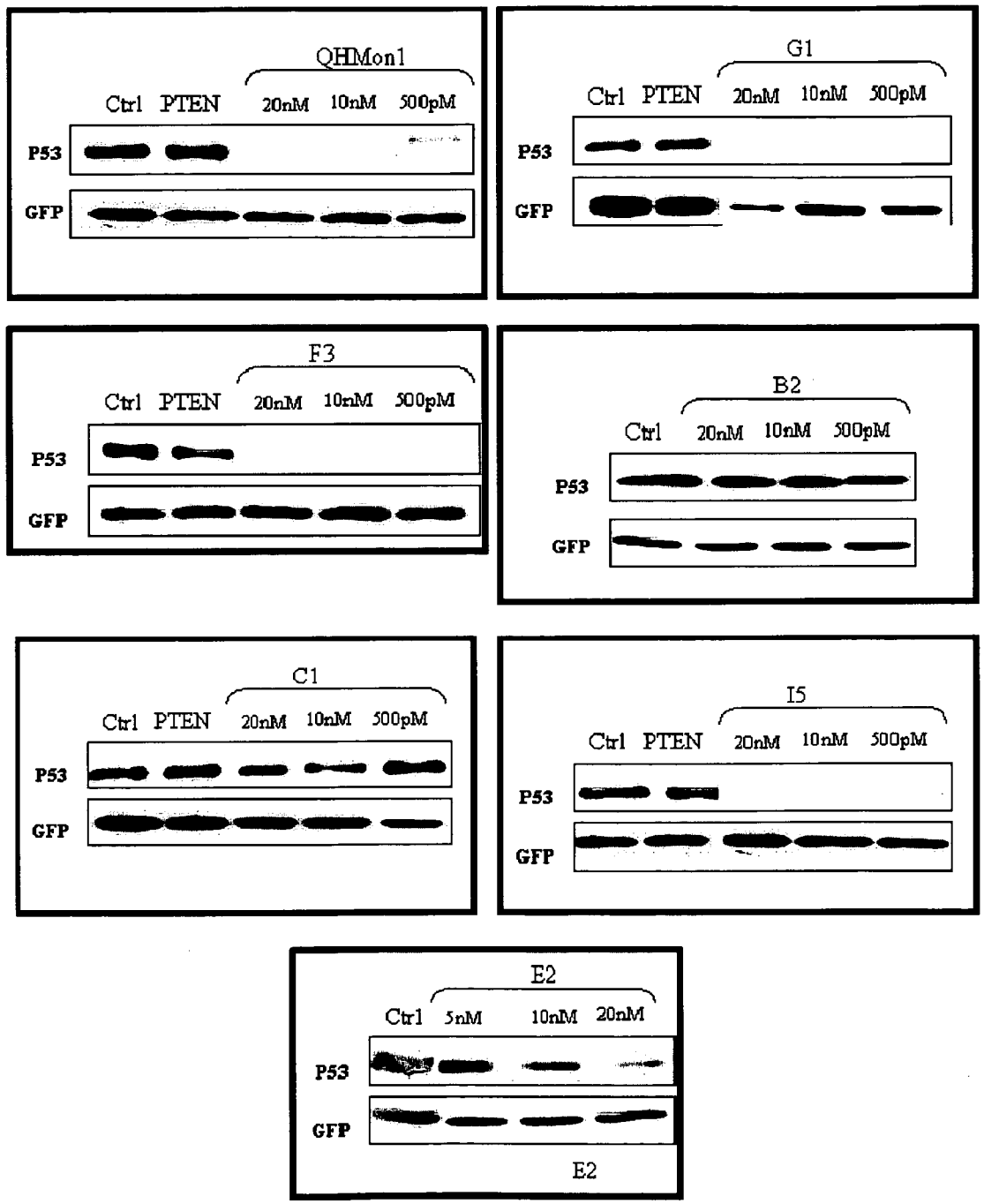
FIG. 3. This figure shows Western Blot results demonstrating the effect of various mouse p53 siRNAs on p53 expression.

The present invention relates generally to compounds which down-regulate expression of the p53 gene particularly to novel small interfering RNAs (siRNAs), and to the use of these novel siRNAs in the treatment of various diseases and medical conditions in particular alopecia or acute renal failure or a disorder accompanied by an elevated level of p53 polypeptide. The inventors of the present invention have found that it is beneficial to induce temporary inhibition of p53 in order to treat any of said diseases or disorders. Methods, molecules and compositions which inhibit p53 are discussed herein at length, and any of said molecules and/or compositions may be beneficially employed in the treatment of a patient suffering from any of said conditions.

The present invention provides methods and compositions for inhibiting expression of a target p53 gene in vivo. In general, the method includes administering oligoribonucleotides, such as small interfering RNAs (i.e., siRNAs) that are targeted to a particular p53 mRNA and hybridize to, or interact with, the mRNAs under biological conditions (within the cell), or a nucleic acid material that can produce siRNA in a cell, in an amount sufficient to down-regulate expression of a target gene by an RNA interference mechanism. In particular, the subject method can be used to inhibit expression of the p53 gene for treatment of a disease.

In accordance with the present invention, the siRNA molecules or inhibitors of the p53 gene may be used as drugs to treat various pathologies in particular alopecia or acute renal failure or other disorders accompanied by an elevated level of p53 polypeptide. Since long-term p53 inactivation can significantly increase the risk of cancer, it is preferred that the inhibition of p53 using the molecules of the present invention be temporary/reversible.

The present invention provides double-stranded oligoribonucleotides (siRNAs), which down-regulate the expression of the p53 gene. An siRNA of the invention is a duplex oligoribonucleotide in which the sense strand is derived from the mRNA sequence of the p53 gene, and the antisense strand is complementary to the sense strand. In general, some deviation from the target mRNA sequence is tolerated without compromising the siRNA activity (see e.g. Czauderna et al 2003 Nucleic Acids Research 31(11), 2705-2716). An siRNA of the invention inhibits gene expression on a post-transcriptional level with or without destroying the mRNA. Without being bound by theory, siRNA may target the mRNA for specific cleavage and degradation and/or may inhibit translation from the targeted message.

There are at least four variant p53 polypeptides (see Bourdon et al. *Genes Dev.* 2005; 19: 2122-2137). The sequence given in FIG. 1 is the nucleotide sequence of gi-8400737. The corresponding polypeptide sequence has 393 amino acids; see FIG. 2. All variants and any other similar minor variants are included in the definition of p53 polypeptide and in the definition of the p53 genes encoding them.

As used herein, the term "p53 gene" is defined as any homolog of the p53 gene having preferably 90% homology, more preferably 95% homology, and even more preferably 98% homology to the amino acid encoding region of SEQ ID NO:1 or nucleic acid sequences which bind to the p53 gene under conditions of highly stringent hybridization, which are well-known in the art (for example, see Ausubel et al., Current Protocols in Molecular Biology, John Wiley and Sons, Baltimore, Md. (1988), updated in 1995 and 1998.

As used herein, the term "p53", or "p53 polypeptide" is defined as any homolog of the p53 polypeptide having preferably 90% homology, more preferably 95% homology, and even more preferably 98% homology to SEQ ID NO:2, as either full-length or a fragment or a domain thereof, as a mutant or the polypeptide encoded by a spliced variant nucleic acid sequence, as a chimera with other polypeptides, provided that any of the above has the same or substantially the same biological function as the p53 polypeptide.

Generally, the siRNAs used in the present invention comprise a ribonucleic acid comprising a double stranded structure, whereby the double-stranded structure comprises a first strand and a second strand, whereby the first strand comprises a first stretch of contiguous nucleotides and whereby said first stretch is at least partially complementary to a target nucleic acid, and the second strand comprises a second stretch of contiguous nucleotides and whereby said second stretch is at least partially identical to a target nucleic acid, whereby said first strand and/or said second strand comprises a plurality of groups of modified nucleotides having a modification at the 2'-position whereby within the strand each group of modified nucleotides is flanked on one or both sides by a flanking group of nucleotides whereby the flanking nucleotides forming the flanking group of nucleotides is either an unmodified nucleotide or a nucleotide having a modification different from the modification of the modified nucleotides. Further, said first strand and/or said second strand may comprise said plurality of modified nucleotides and may comprises said plurality of groups of modified nucleotides.

The group of modified nucleotides and/or the group of flanking nucleotides may comprise a number of nucleotides whereby the number is selected from the group comprising one nucleotide to 10 nucleotides. In connection with any ranges specified herein it is to be understood that each range discloses any individual integer between the respective figures used to define the range including said two figures defining said range. In the present case the group thus comprises one nucleotide, two nucleotides, three nucleotides, four nucleotides, five nucleotides, six nucleotides, seven nucleotides, eight nucleotides, nine nucleotides and ten nucleotides.

The pattern of modified nucleotides of said first strand may be shifted by one or more nucleotides relative to the pattern of modified nucleotides of the second strand.

The modifications discussed above may be selected from the group comprising amino, fluoro, methoxy alkoxy, alkyl, amino, fluoro, chloro, bromo, CN, CF, imidazole, caboxylate, thioate, $C_1$ to $C_{10}$ lower alkyl, substituted lower alkyl, alkaryl or aralkyl, $OCF_3$, OCN, O-, S-, or N-alkyl; O-, S-, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP O 586 520 B1 or EP O 618 925 B1.

The double stranded structure of the siRNA may be blunt ended, on one or both sides. More specifically, the double stranded structure may be blunt ended on the double stranded structure's side which is defined by the 5'-end of the first strand and the 3'-end of the second strand, or the double stranded structure may be blunt ended on the double stranded structure's side which is defined by at the 3'-end of the first strand and the 5'-end of the second strand.

Additionally, at least one of the two strands may have an overhang of at least one nucleotide at the 5'-end; the overhang may consist of at least one deoxyribonucleotide. At least one of the strands may also optionally have an overhang of at least one nucleotide at the 3'-end.

The length of the double-stranded structure of the siRNA is typically from about 17 to 21 and more preferably 18 or 19 bases. Further, the length of said first strand and/or the length of said second strand may independently from each other be selected from the group comprising the ranges of from about 15 to about 23 bases, 17 to 21 bases and 18 or 19 bases.

Additionally, the complementarily between said first strand and the target nucleic acid may be perfect, or the duplex formed between the first strand and the target nucleic acid may comprise at least 15 nucleotides wherein there is one mismatch or two mismatches between said first strand and the target nucleic acid forming said double-stranded structure.

In some cases both the first strand and the second strand each comprise at least one group of modified nucleotides and at least one flanking group of nucleotides, whereby each group of modified nucleotides comprises at least one nucleotide and whereby each flanking group of nucleotides comprising at least one nucleotide with each group of modified nucleotides of the first strand being aligned with a flanking group of nucleotides on the second strand, whereby the most terminal 5' nucleotide of the first strand is a nucleotide of the group of modified nucleotides, and the most terminal 3' nucleotide of the second strand is a nucleotide of the flanking group of nucleotides. Each group of modified nucleotides may consist of a single nucleotide and/or each flanking group of nucleotides may consist of a single nucleotide.

Additionally, it is possible that on the first strand the nucleotide forming the flanking group of nucleotides is an unmodified nucleotide which is arranged in a 3' direction relative to the nucleotide forming the group of modified nucleotides, and on the second strand the nucleotide forming the group of modified nucleotides is a modified nucleotide which is arranged in 5' direction relative to the nucleotide forming the flanking group of nucleotides.

Further the first strand of the siRNA may comprise eight to twelve, preferably nine to eleven, groups of modified nucleotides, and the second strand may comprise seven to eleven, preferably eight to ten, groups of modified nucleotides.

The first strand and the second strand may be linked by a loop structure, which may be comprised of a non-nucleic acid polymer such as, inter alia, polyethylene glycol. Alteratively, the loop structure may be comprised of a nucleic acid.

Further, the 5'-terminus of the first strand of the siRNA may be linked to the 3'-terminus of the second strand, or the 3'-end of the first strand may be linked to the 5'-terminus of the second strand, said linkage being via a nucleic acid linker typically having a length between 10-2000 nucleobases.

In particular, the invention provides a compound having structure A:

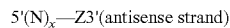

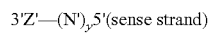

wherein each N and N' is a ribonucleotide which may be modified or unmodified in its sugar residue and $(N)_x$ and $(N')_y$ is oligomer in which each consecutive N or N' is joined to the next N or N' by a covalent bond;

wherein each of x and y is an integer between 19 and 40;

wherein each of Z and Z' may be present or absent, but if present is dTdT and is covalently attached at the 3' terminus of the strand in which it is present;

and wherein the sequence of $(N)_x$ comprises an antisense sequence to mRNA of p53 in particular any of the antisense sequences present in any of Tables A, B and C.

It will be readily understood by those skilled in the art that the compounds of the present invention consist of a plurality of nucleotides, which are linked through covalent linkages. Each such covalent linkage may be a phosphodiester linkage, a phosphothioate linkage, or a combination of both, along the length of the nucleotide sequence of the individual strand. Other possible backbone modifications are described inter alia in U.S. Pat. Nos. 5,587,361; 6,242,589; 6,277,967; 6,326,358; 5,399,676; 5,489,677; and 5,596,086.

In particular embodiments, x and y are preferably an integer between about 19 to about 27, most preferably from about 19 to about 23. In a particular embodiment of the compound of the invention, x may be equal to y (viz., x=y) and in preferred embodiments x=y=19 or x=y=21. In a particularly preferred embodiment x=y=19.

In one embodiment of the compound of the invention, Z and Z' are both absent; in another embodiment one of Z or Z' is present.

In one embodiment of the compound of the invention, all of the ribonucleotides of the compound are unmodified in their sugar residues.

In preferred embodiments of the compound of the invention, at least one ribonucleotide is modified in its sugar residue, preferably a modification at the 2' position. The modification at the 2' position results in the presence of a moiety which is preferably selected from the group comprising amino, fluoro, methoxy, alkoxy and alkyl groups. In a presently most preferred embodiment the moiety at the 2' position is methoxy (2'-O-methyl).

In preferred embodiments of the invention, alternating ribonucleotides are modified in both the antisense and the sense strands of the compound. In particular the siRNA used in the Examples has been such modified such that a 2' O-Me group was present on the first, third, fifth, seventh, ninth, eleventh, thirteenth, fifteenth, seventeenth and nineteenth nucleotide of the antisense strand, whereby the very same modification, i. e. a 2'-O-Me group was present at the second, fourth, sixth, eighth, tenth, twelfth, fourteenth, sixteenth and eighteenth nucleotide of the sense strand. Additionally, it is to be noted that the in case of these particular nucleic acids according to the present invention the first stretch is identical to the first strand and the second stretch is identical to the second strand and these nucleic acids are also blunt ended.

In a particularly preferred embodiment the sequence of the siRNA is that of I5 in Table A.

According to one preferred embodiment of the invention, the antisense and the sense strands of the siRNA molecule are both phophorylated only at the 3'-terminus and not at the 5'-terminus. According to another preferred embodiment of the invention, the antisense and the sense strands are both non-phophorylated both at the 3'-terminus and also at the 5'-terminus. According to yet another preferred embodiment of the invention, the $1^{st}$ nucleotide in the 5' position in the sense strand is specifically modified to abolish any possibility of in vivo 5'-phosphorylation.

In another embodiment of the compound of the invention, the ribonucleotides at the 5' and 3' termini of the antisense strand are modified in their sugar residues, and the ribonucleotides at the 5' and 3' termini of the sense strand are unmodified in their sugar residues.

The invention further provides a vector capable of expressing any of the aforementioned oligoribonucleotides in unmodified form in a cell after which appropriate modification may be made.

The invention also provides a composition comprising one or more of the compounds of the invention in a carrier, preferably a pharmaceutically acceptable carrier. This composition may comprise a mixture of two or more different siRNAs.

The invention also provides a composition which comprises the above compound of the invention covalently or non-covalently bound to one or more compounds of the invention in an amount effective to inhibit human p53 and a carrier. This composition may be processed intracellularly by endogenous cellular complexes to produce one or more oligoribonucleotides of the invention.

The invention also provides a composition comprising a carrier and one or more of the compounds of the invention in an amount effective to down-regulate expression in a cell of a human p53, which compound comprises a sequence substantially complementary to the sequence of $(N)_x$.

Additionally the invention provides a method of down-regulating the expression of gene p53 by at least 50% as compared to a control comprising contacting an mRNA transcript of gene p53 with one or more of the compounds of the invention.

In one embodiment the oligoribonucleotide is down-regulating p53, whereby the down-regulation of p53 is selected from the group comprising down-regulation of p53 function, down-regulation of p53 polypeptide and down-regulation of p53 mRNA expression.

In one embodiment the compound is down-regulating a p53 polypeptide, whereby the down-regulation of p53 is selected from the group comprising down-regulation of p53 function (which may be examined by an enzymatic assay or a binding assay with a known interactor of the native gene/polypeptide, inter alia), down-regulation of p53 protein (which may be examined by Western blotting, ELISA or immuno-precipitation, inter alia) and down-regulation of p53 mRNA expression (which may be examined by Northern blotting, quantitative RT-PCR, in-situ hybridisation or microarray hybridisation, inter alia).

The invention also provides a method of treating a patient suffering from a disease accompanied by an elevated level of p53 polypeptide, the method comprising administering to the patient a composition of the invention in a therapeutically effective dose thereby treating the patient. Preferably, the present invention provides a method of treating a patient suffering from a disease in which temporary inhibition of p53 is beneficial. In one preferred embodiment, the compositions of the present invention are used for the treatment of tumors along with the conventional chemotherpy or radiotherapy in order to prevent the alopecia associated with chemotherapy or radiotherapy. In another preferred embodiment, the compositions of the present invention are used for the treatment of acute renal failure. In yet another preferred embodiment, the compositions of the present invention are used in conditions in which p53 is activated as a consequence of a variety of stresses associated with injuries such as a burn, hyperthermia, hypoxia associated with a blocked blood supply such as in myocardial infraction, stroke, and ischemia. Temporary p53 inhibition using the siRNA molecules of the present invention can be therapeutically effective in reducing or eliminating p53-dependent neuronal death in the central nervous system, i.e., brain and spinal cord injury, in preserving of tissue and an organ prior to transplanting, preparation of a host for a bone marrow transplant, reducing or eliminating neuronal damage during a seizure and in suppressing tissue aging.

The invention also provides a use of a therapeutically effective dose of one or more compounds of the invention for the preparation of a composition for the treatment of a disease accompanied by an elevated level of p53 polypeptide, such as in a patient suffering from alopecia or acute renal failure.

More particularly, the invention provides an oligoribonucleotide wherein one strand comprises consecutive nucleotides having, from 5' to 3', the sequence set forth in SEQ ID NOS: 3-25 (Table A, sense strands) or in SEQ ID NOS: 49-119 (Table B, sense strands) or in SEQ ID NOS: 191-253 (Table C, sense strands) or a homolog thereof wherein in up to 2 of the nucleotides in each terminal region a base is altered.

The terminal region of the oligonucleotide refers to bases 1-4 and/or 16-19 in the 19-mer sequence and to bases 1-4 and/or 18-21 in the 21-mer sequence.

Additionally, the invention provides oligoribonucleotides wherein one strand comprises consecutive nucleotides having, from 5' to 3', the sequence set forth SEQ ID NOS: 26-48 (Table A, antisense strands) or SEQ ID NOS: 120-190 (Table B, antisense strands) or SEQ ID NOS: 254-316 (Table C, antisense strands) or a homolog thereof wherein in up to 2 of the nucleotides in each terminal region a base is altered.

The preferred oligonucleotides of the invention are human p53 oligonucleotides serial numbers 3, 5, 20 and 23 in Table D and mouse p53 oligonucleotides serial numbers 1 11, 12, 14, 17 and 18 in Table E. These are identical to serial numbers 3, 5, 20 and 23 (human) and also 11, 12, 14, 17 and 18 (mouse) in Table A. The most preferred oligonucleotides of the invention are human p53 oligonucleotides having the sequence of serial number 23 in Table A.

The presently most preferred compound of the invention is a blunt-ended 19-mer oligonucleotide, i.e. x=y=19 and Z and Z' are both absent. The oligonucleotide molecule is either phosphorylated at 3' termini of both sense and anti-sense strands, or non-phosphorylated at all; or having $1^{st}$ nucleotide in the 5' position on the sense strand specifically modified to abolish any possibility of in vivo 5'-phosphorylation. The alternating ribonucleotides are modified at the 2' position in both the antisense and the sense strands, wherein the moiety at the 2' position is methoxy (2'-0-methyl) and wherein the ribonucleotides at the 5' and 3' termini of the antisense strand are modified in their sugar residues, and the ribonucleotides at the 5' and 3' termini of the sense strand are unmodified in their sugar residues. The presently most preferred such compounds are such modified oligonucleotides comprising the sequences having serial number 23 in Table A.

In one aspect of the invention the oligonucleotide comprises a double-stranded structure, whereby such double-stranded structure comprises
- a first strand and a second strand, whereby
- the first strand comprises a first stretch of contiguous nucleotides and the second strand comprises a second stretch of contiguous nucleotides, whereby
- the first stretch is either complementary or identical to a nucleic acid sequence coding for p53 and whereby the second stretch is either identical or complementary to a nucleic acid sequence coding for p53.

In an embodiment the first stretch and/or the second stretch comprises from about 14 to 40 nucleotides, preferably about 18 to 30 nucleotides, more preferably from about 19 to 27 nucleotides and most preferably from about 19 to 23 nucleotides, in particular from about 19 to 21 nucleotides. In such an embodiment the oligonucleotide may be from 17-40 nucleotides in length.

Additionally, further nucleic acids according to the present invention comprise at least 14 contiguous nucleotides of any one of the polynucleotides in the Tables and more preferably 14 contiguous nucleotide base pairs at any end of the double-stranded structure comprised of the first stretch and second stretch as described above.

In an embodiment the first stretch comprises a sequence of at least 14 contiguous nucleotides of an oligonucleotide, whereby such oligonucleotide is selected from the group comprising SEQ. ID. Nos 3-316, preferably from the group comprising the oligoribonucleotides of halving the sequence of any of the serial numbers 3, 5, 20 or 23 (human) or having the sequence of any of the serial numbers 11, 12, 14, 17 and 18 (mouse) in Table A, more preferably selected from the group having the sequence of any of the serial numbers 3, 5, 20 or 23 in Table A.

Additionally, further nucleic acids according to the present invention comprise at least 14 contiguous nucleotides of any one of the SEQ. ID. NO. 3 to 316, and more preferably 14 contiguous nucleotide base pairs at any end of the double-stranded structure comprised of the first stretch and second stretch as described above. It will be understood by one skilled in the art that given the potential length of the nucleic acid according to the present invention and particularly of the individual stretches forming such nucleic acid according to the present invention, some shifts relative to the coding sequence of p53 to each side is possible, whereby such shifts can be up to 1, 2, 3, 4, 5 and 6 nucleotides in both directions, and whereby the thus generated double-stranded nucleic acid molecules shall also be within the present invention.

Delivery: Delivery systems aimed specifically at the enhanced and improved delivery of siRNA into mammalian cells have been developed, see, for example, Shen et al (FEBS letters 539: 111-114 (2003)), Xia et al., Nature Biotechnology 20: 1006-1010 (2002), Reich et al., Molecular Vision 9: 210-216 (2003), Sorensen et al. (J. Mol. Biol. 327: 761-766 (2003), Lewis et al., Nature Genetics 32: 107-108 (2002) and Simeoni et al., Nucleic Acids Research 31, 11: 2717-2724 (2003). siRNA has recently been successfully used for inhibition in primates; for further details see Tolentino et al., Retina 24(1) February 2004 I 132-138. Respiratory formulations for siRNA are described in U.S. patent application No. 2004/0063654 of Davis et al. Cholesterol-conjugated siRNAs (and other steroid and lipid conjugated siRNAs) can been used for delivery see Soutschek et al Nature 432: 173-177 (2004) *Therapeutic silencing of an endogenous gene by systemic administration of modified siRNAs*; and Lorenz et al. Bioorg. Med. Chemistry. Lett. 14:4975-4977 (2004) *Steroid and lipid conjugates of siRNAs to enhance cellular uptake and gene silencing in liver cells.*

The siRNAs or pharmaceutical compositions of the present invention are administered and dosed in accordance with good medical practice, taking into account the clinical condition of the individual patient, the disease to be treated, the site and method of administration, scheduling of administration, patient age, sex, body weight and other factors known to medical practitioners.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art. The compounds of the present invention can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic co-solvents, aqueous or oil suspensions, emulsions with edible oils, as well as similar pharmaceutical vehicles. In addition, under certain circumstances the compositions for use in the novel treatments of the present invention may be formed as aerosols, for intranasal and like administration. The patient being treated is a warm-blooded animal and, in particular, mammals including man. The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art. In one specific embodiment of this invention topical and transdermal formulations are particularly preferred.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-4 weeks or longer.

It is noted that the delivery of the siRNA compounds according to the present invention to the target cells in the kidney proximal tubules is particularity effective in the treatment of acute renal failure. Without being bound by theory, this may be due to the fact that normally siRNA molecules are excreted from the body via the cells of the kidney proximal tubules. Thus, naked siRNA molecules are naturally concentrated in the cells that are targeted for the therapy in acute renal failure.

The term "treatment" as used herein refers to administration of a therapeutic substance effective to ameliorate symptoms associated with a disease, to lessen the severity or cure the disease, or to prevent the disease from occurring.

In a particular embodiment, the administration comprises intravenous administration. In another particular embodiment the administration comprises topical or local administration Another aspect of the invention is a method of treating a patient suffering from alopecia or acute renal failure or a disorder which is accompanied by an elevated level of p53 polypeptide, comprising administering to the patient a pharmaceutical composition of the invention in a therapeutically effective amount so as to thereby treat the patient.

In a preferred embodiment for treatment of alopecia, the administration comprises topical or local administration. In another preferred embodiment the administration comprises transdermal administration. In a particular embodiment the pharmaceutical composition is applied to the scalp of the patient. In a preferred embodiment for treatment of ARF, the administration comprises intravenous, intra-arterial or intra-peritoneal administration Another aspect of the invention is a method of preventing alopecia in a patient undergoing treatment which causes alopecia, comprising administering to the patient a pharmaceutical composition of the invention in a therapeutically effective amount so as to thereby treat the patient.

In another aspect of the invention a pharmaceutical composition is provided which comprises any of the above oligoribonucleotides (SEQ ID NOS: 3-316) or vectors and a pharmaceutically acceptable carrier. Another aspect of the invention is the use of a therapeutically effective amount of any of the above oligoribonucleotides (SEQ ID NOS: 3-316) or vectors for the preparation of a medicament for promoting recovery in a patient suffering from alopecia or acute renal failure or a disorder which is accompanied by an elevated level of p53.

In a preferred embodiment, the medicament comprises a topical medicament. In a particular embodiment the medicament is applied to the scalp of the patient. In another preferred embodiment the medicament comprises transdermal administration In all the above aspects of the invention the alopecia may be induced by chemotherapy or by radiotherapy and is then termed "toxic alopecia". In more detail, toxic alopecia may be caused by irradiation such as gamma irradiation or by chemotherapeutic agents such as etoposide, 5-FU (5-fluorouracil), cis-platinum, doxorubicin, a vinca alkaloid, vincristine, vinblastine, vinorelbine, taxol, cyclophosphamide, ifosfamide, chlorambucil, busulfan, mechlorethamine, mitomycin, dacarbazine, carboplatinum, thiotepa, daunorubicin, idarubicin, mitoxantrone, bleomycin, esperamicin A1, dactinomycin, plicamycin, carmustine, lomustine, tauromustine, streptozocin, melphalan, dactinomycin, procarbazine, dexamethasone, prednisone, 2-chlorodeoxyadenosine, cytarabine, docetaxel, fludarabine, gemcitabine, herceptin, hydroxyurea, irinotecan, methotrexate, oxaliplatin, rituxin, semustine, epirubicin, etoposide, tomudex and topotecan, or a chemical analog of one of these chemotherapeutic agents. The chemotherapeutic agents most likely to cause hair loss are: cis-platinum, cytarabine, cyclophosphamide, doxorubicin, epirubicin, etoposide, ifosfamide and vincristine.

The compounds of the invention are preferably used for treating acute renal failure, in particular acute renal failure due to ischemia in post surgical patients, and acute renal failure due to chemotherapy treatment such as cisplatin administration or sepsis-associated acute renal failure. A preferred use of the compounds of the invention is for the prevention of acute renal failure in high-risk patients undergoing major cardiac surgery or vascular surgery. The patients at high-risk of developing acute renal failure can be identified using various scoring methods such as the Cleveland Clinic algorithm or that developed by US Academic Hospitals (QMMI) and by Veterans' Administration (CICSS). Other preferred uses of the compounds of the invention are for the prevention of ischemic acute renal failure in kidney transplant patients or for the prevention of toxic acute renal failure in patients receiving chemotherapy. Other uses are for wound healing, acute liver failure, cisplatin-induced deafness (perhaps topically), ex vivo expansion of hematopoietic stem cells, preservation of donor organs/tissues before transplantation by soaking in siRNA solution (perhaps by electroporation) and subsequent improvement of graft tissue survival following transplantation. Other indications may be stroke, Parkinson's disease, Alzheimer's disease, doxorubicin-induced cardiotoxicity, myocardial infarction/heart failure and improvement of graft tissue survival following transplantation (by systemic administration). Without being bound by theory all these disorders are accompanied by an elevated level of p53 polypeptide.

The present invention also provides for a process of preparing a pharmaceutical composition, which comprises:
  obtaining one or more double stranded compound of the invention; and
  admixing said compound with a pharmaceutically acceptable carrier.

The present invention also provides for a process of preparing a pharmaceutical composition, which comprises admixing one or more compounds of the present invention with a pharmaceutically acceptable carrier.

In a preferred embodiment, the compound used in the preparation of a pharmaceutical composition is admixed with a carrier in a pharmaceutically effective dose. In a particular embodiment the compound of the present invention is conjugated to a steroid or to a lipid or to another suitable molecule e.g. to cholesterol.

Modifications or analogs of nucleotides can be introduced to improve the therapeutic properties of the nucleotides. Improved properties include increased nuclease resistance and/or increased ability to permeate cell membranes.

Accordingly, the present invention also includes all analogs of, or modifications to, a oligonucleotide of the invention that does not substantially affect the function of the polynucleotide or oligonucleotide. In a preferred embodiment such modification is related to the base moiety of the nucleotide, to the sugar moiety of the nucleotide and/or to the phosphate moiety of the nucleotide.

In embodiments of the invention, the nucleotides can be selected from naturally occurring or synthetically modified bases. Naturally occurring bases include adenine, guanine, cytosine, thymine and uracil. Modified bases of the oligonucleotides include inosine, xanthine, hypoxanthine, 2-aminoadenine, 6-methyl-, 2-propyl- and other alkyl-adenines, 5-halo uracil, 5-halo cytosine, 6-aza cytosine and 6-aza thymine, pseudo uracil, 4-thiuracil, 8-halo adenine, 8-aminoadenine, 8-thiol adenine, 8-thioalkyl adenines, 8-hydroxyl adenine and other 8-substituted adenines, 8-halo guanine, 8-amino guanine, 8-thiol guanine, 8-thioalkyl guanine, 8-hydroxyl guanine and other substituted guanines, other aza and deaza adenines, other aza and deaza guanines, 5-trifluoromethyl uracil and 5-trifluoro cytosine.

In addition, analogs of nucleotides can be prepared wherein the structures of the nucleotides are fundamentally altered and are better suited as therapeutic or experimental reagents. An example of a nucleotide analog is a peptide nucleic acid (PNA) wherein the deoxyribose (or ribose) phosphate backbone in DNA (or RNA) is replaced with a polyamide backbone similar to that found in peptides. PNA analogs have been shown to be resistant to degradation by enzymes and to have extended lives in vivo and in vitro. Further, PNAs have been shown to bind more strongly to a complementary DNA sequence than to a DNA molecule. This observation is attributed to the lack of charge repulsion between the PNA strand and the DNA strand. Other modifications that can be made to oligonucleotides include polymer backbones, cyclic backbones, or acyclic backbones.

In one embodiment the modification is a modification of the phosphate moiety, whereby the modified phosphate moiety is selected from the group comprising phosphothioate.

The compounds of the present invention can be synthesized by any of the methods that are well-known in the art for synthesis of ribonucleic (or deoxyribonucleic) oligonucleotides. Such synthesis is, among others, described in Beaucage S. L. and Iyer R. P., Tetrahedron 1992; 48: 2223-2311, Beaucage S. L. and Iyer R. P., Tetrahedron 1993; 49: 6123-6194 and Caruthers M. H. et. al., Methods Enzymol. 1987; 154: 287-313; the synthesis of thioates is, among others, described in Eckstein F., Annu. Rev. Biochem. 1985; 54: 367-402, the synthesis of RNA molecules is described in Sproat B., in Humana Press 2005 edited by Herdewijn P.; Kap. 2: 17-31 and respective downstream processes are, among others, described in Pingoud A. et. al., in IRL Press 1989 edited by Oliver R. W. A.; Kap. 7: 183-208 and Sproat B., in Humana Press 2005 edited by Herdewijn P.; Kap. 2: 17-31 (supra).

Other synthetic procedures are known in the art e.g. the procedures as described in Usman et al., 1987. *J. Am. Chem. Soc.,* 109, 7845; Scaringe et al., 1990, *Nucleic Acids Res.,* 18, 5433; Wincott et al., 1995, *Nucleic Acids Res.* 23, 2677-2684; and Wincott et al., 1997, *Methods Mol. Bio.,* 74, 59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated is desired.

The oligonucleotides of the present invention can be synthesized separately and joined together post-synthetically, for example, by ligation (Moore et al., 1992, *Science* 256, 9923; Draper et al., International PCT publication No. WO93/23569; Shabarova et al., 1991, *Nucleic Acids Research* 19, 4247; Bellon et al., 1997, *Nucleosides & Nucleotides,* 16, 951; Bellon et al., 1997, *Bioconjugate Chem.* 8, 204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The compounds of the invention can also be synthesized via a tandem synthesis methodology, as described in US patent application publication No. US2004/0019001 (McSwiggen), wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

The present invention further provides for a pharmaceutical composition comprising two or more siRNA molecules for the treatment of any of the diseases and conditions mentioned herein, whereby said two molecules may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides. In one embodiment, the siRNA molecules are comprised of a double-stranded nucleic acid structure as described herein, wherein the two siRNA sequences are selected from Tables A-C, preferably from Table A, ID Nos: 3, 5, 20 and 23 (human sequences) and 11, 12, 14, 17 and 18 (mouse sequences).

In another embodiment, the siRNA molecules are comprised of a double-stranded nucleic acid structure, wherein the first siRNA sequence is selected from Tables A-C, preferably from Table A, ID Nos: 3, 5, 20 and 23 (human p53 sequences) or 11, 12, 14, 17 and 18 (mouse p53 sequences) and the second siRNA molecule targets a pro-apoptotic gene, thereby providing beneficial activity. The tandem double-stranded structure which comprises two or more siRNA sequences is processed intracellularly to form two or more different siRNAs. Such second siRNA molecule is preferably an siRNA molecule that targets a pro-apoptotic gene.

The siRNA molecules are covalently or non-covalently bound or joined by a linker to form a tandem siRNA molecule. Such tandem siRNA molecules comprising two siRNA sequences are typically of 38-150 nucleotides in length, more preferably 38 or 40-60 nucleotides in length, and longer accordingly if more than two siRNA sequences are included in the tandem molecule. A longer tandem molecule comprised of two or more longer sequences which encode siRNA produced via internal cellular processing, e.g., long dsRNAs, is also envisaged, as is a tandem molecule encoding two or more shRNAs. Such tandem molecules are also considered to be a part of the present invention.

siRNA molecules that target p53 may be the main active component in a pharmaceutical composition, or may be one active component of a pharmaceutical composition containing two or more siRNAs (or molecules which encode or endogenously produce two or more siRNAs, be it a mixture of molecules or one or more tandem molecules which encode two or more siRNAs), said pharmaceutical composition further being comprised of one or more additional siRNA molecule which targets one or more additional gene. Simultaneous inhibition of p53 and said additional gene(s) will likely have an additive or synergistic effect for treatment of the diseases disclosed herein.

In a specific example, the pharmaceutical composition for treatment of the diseases disclosed herein may be comprised of the following compound combinations: 1) p53 siRNA and Fas siRNA; 2) p53 siRNA and Bax siRNA; 3) p53 siRNA and Noxa siRNA; 4) p53 siRNA and Puma siRNA; 5) p53 siRNA and RTP801 siRNA; 6) p53 siRNA and PIDD siRNA; 7) p53 siRNA, Fas siRNA and any of RTP801 siRNA, Bax siRNA, Noxa siRNA or Puma siRNA or PIDD siRNA to form trimers or polymers (i.e., tandem molecules which encode three siRNAs). Other preferred options of pro-apoptotic genes to be combined with the p53 siRNA are TNFα, caspase 2, caspase 3, caspase 9, E2F1, and PARP-1. A preferred combination according to the present invention is p53 siRNA and RTP801 siRNA. (see PCT patent application PCT/EP 2005/008891).

Additionally, p53 siRNA or any nucleic acid molecule comprising or encoding p53 siRNA can be linked (covalently or non-covalently) to antibodies against cell surface internalizable molecules expressed on the target cells, in order to achieve enhanced targeting for treatment of the diseases disclosed herein. For example, anti-Fas antibody (preferably a neutralizing antibody) may be combined with a p53 siRNA molecule.

The compounds of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell. Vectors optionally used for delivery of the compounds of the present invention are commercially available, and may be modified for the purpose of delivery of the compounds of the present invention by methods known to one of skill in the art.

It is also envisaged that a long oligonucleotide (typically 25-500 nucleotides in length) comprising one or more stem and loop structures, where stem regions comprise the sequences of the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide can be termed a tandem shRNA construct. It is envisaged that this long oligonucleotide is a single stranded oligonucleotide comprising one or more stem and loop structures, wherein each stem region comprises a sense and corresponding antisense siRNA sequence of an p53 gene. In particular, it is envisaged that this oligonucleotide comprises sense and antisense siRNA sequences as depicted in any one of Tables A, B or C.

As used herein, the term "polypeptide" refers to, in addition to a polypeptide, an oligopeptide, peptide and a full protein.

Screening of p53 Inactivation Compounds:

Some of the compounds and compositions of the present invention may be used in a screening assay for identifying and isolating compounds that modulate the activity of p53, in particular compounds that modulate alopecia or acute renal failure or a disorder accompanied by all elevated level of p53 polypeptide. The compounds to be screened comprise inter alia substances such as small chemical molecules and antisense oligonucleotides.

The inhibitory activity of the compounds of the present invention on p53 polypeptide activity or binding of the compounds of the present invention to p53 may be used to determine the interaction of an additional compound with the p53 polypeptide, e.g., if the additional compound competes with the oligonucleotides of the present invention for p53 inhibition, or if the additional compound rescues said inhibition. The inhibition or activation can be tested by various means, such as, inter alia, assaying for the product of the activity of the p53 polypeptide or displacement of binding compound from the p53 polypeptide in radioactive or fluorescent competition assays.

The present invention is illustrated in detail below with reference to Examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

General Methods in Molecular Biology

Standard molecular biology techniques known in the art and not specifically described were generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683, 202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry can be used for detection of cells containing specific DNA and mRNA sequences (Testoni et al., 1996, Blood 87:3822.) Methods of performing RT-PCR are also well known in the art.

Example 1

Generation of Sequences for Active siRNA Compounds

Using proprietary algorithms and the known sequence of gene p53 (SEQ ID NO:1), the sequences of many potential siRNAs were generated. Table A shows 23 siRNAs which have so far been selected, chemically synthesized and tested for activity (see Example 2). All these siRNAs are 19-mers.

TABLE A

| Number | Index | Sense strand | Antisense strand | Species | NM_000546 (human) | NM_011640 (mouse) | NM_030989 (rat) |
|---|---|---|---|---|---|---|---|
| 1 | Mo3 | GUACAUGUGUAAUAGCUCC | GGAGCUAUUACACAUGUAC | mouse | 3 mis | 1232-1250 | 2 mis |
| 2 | Hu2 | GACUCCAGUGGUAAUCUAC | GUAGAUUACCACUGGAGUC | human* | 1026-1044 | 3 mis | 2 mis |
| 3 | QHMo n1 | CAGACCUAUGGAAACUACU | AGUAGUUUCCAUAGGUCUG | hum, mon | 310-328 | 3 mis | 4 mis |

TABLE A-continued

| Number | Index | Sense strand | Antisense strand | Species | NM_000546 (human) | NM_011640 (mouse) | NM_030989 (rat) |
|---|---|---|---|---|---|---|---|
| 4 | QHMon2 | CUACCUCCCGCCAUAAAA | UUUUUAUGGCGGGAGGUAG | hum, mon | 1378-1396 | 1 mis | 1 mis |
| 5 | QH1 | CCCAAGCAAUGGAUGAUUU | AAAUCAUCCAUUGCUUGGG | human | 361-379 | No | No |
| 6 | QH2 | CCCGGACGAUAUUGAACAA | UUGUUCAAUAUCGUCCGGG | human | 389-407 | No | No |
| 7 | QM1 | GAGUCACAGUCGGAUAUCA | UGAUAUCCGACUGUGACUC | mouse | No | 552-570 | 2 mis |
| 8 | QM2 | GGAUGUUGAGGAGUUUUUU | AAAAAACUCCUCAACAUCC | mouse | No | 680-698 | 4 mis |
| 9 | QM3 | CAUCUUUUGUCCCUUCUCA | UGAGAAGGGACAAAAGAUG | mouse | 2 mis | 808-826 | 2 mis |
| 10 | QM6 | GGAAUAGGUUGAUAGUUGU | ACAACUAUCAACCUAUUCC | mouse | No | 1870-1888 | No |
| 11 | QM4 | GGACAGCCAAGUCUGUUAU | AUAACAGACUUGGCUGUCC | mouse, rat | 2 mis | 877-895 | 527-545 |
| 12 | QM5 | GAAGAAAAUUUCCGCAAAA | UUUUGCGGAAAUUUUCUUC | mouse, rat | 3 mis | 1383-1401 | 1033-1051 |
| 13 | A17 | CUGGGACAGCCAAGUCUGU | ACAGACUUGGCUGUCCCAG | hum, mus | 598-616 | 874-14 | 2 mis |
| 14 | E2 | UCAUCACACUGGAAGACUC | GAGUCUUCCAGUGUGAUGA | hum, mus, rat | 1012-1030 | 1288-1306 | 938-956 |
| 15 | E6 | CACACUGGAAGACUCCAGU | ACUGGAGUCUUCCAGUGUG | hum, mus, rat | 1016-1034 | 1292-1310 | 942-960 |
| 16 | B1 | GCGCCAUGGCCAUCUACAA | UUGUAGAUGGCCAUGGCGC | hum, mon, mus | 724-742 | 1000-1018 | 652-668(17) |
| 17 | B2 | CGCCAUGGCCAUCUACAAG | CUUGUAGAUGGCCAUGGCG | hum, mon, mus | 725-743 | 1001-1019 | 652-669(18) |
| 18 | C1 | AGUCACAGCACAUGACGGA | UCCGUCAUGUGCUGUGACU | hum, mon, mus | 745-763 | 1021-1039 | 2 mis |
| 19 | F2 | UCCGAGUGGAAGGAAAUUU | AAAUUUCCUUCCACUCGGA | hum, mon, dog, | 835-853 | 1 mis | 3 mis |
| 20 | F3 | CCGAGUGGAAGGAAAUUUG | CAAAUUUCCUUCCACUCGG | hum, mon, dog, | 836-854 | 1 mis | 3 mis |
| 21 | G1 | GACAGAAACACUUUUCGAC | GUCGAAAAGUGUUUCUGUC | hum, mon, dog, | 873-891 | No | No |
| 22 | H2 | GUGUGGUGGUGCCCUAUGA | UCAUAGGGCACCACCACAC | hum, mon, dog, | 895-913 | 3 mis | 3 mis |
| 23 | I5 | GAGAAUAUUUCACCCUUCA | UGAAGGGUGAAAUAUUCUC | hum, mon, dog, | 1225-1243 | 2 mis | 1 mis |

Note that in the above Table A, the sense strands of siRNAs 1-23 have SEQ ID NOS: 3-25 respectively, and the antisense strands of siRNAs 1-23 have SEQ ID NOS: 26-48 respectively. siRNA compound No 1 (SEQ ID NOS: 3 and 26) is known from the literature (Dirac and Bernards, Reversal of senescence in mouse fibroblasts through lentiviral suppression of p53. Biol. Chem.(2003) 278:11731) and siRNA No 2 (SEQ ID NOS:4 and 27) is also known from the literature (Brummelkamp et al. Science 2002, 296:550-553). However, the use of these compounds in the methods of treatment disclosed herein is previously undisclosed and thus novel.

Table B below shows 71 additional 19-mer siRNAs which have been generated by the proprietary algorithms.

TABLE B

| No. | Source | Sense | AntiSense | gi13097806 gbBC003596.1 (Homo sapiens) | gi2689466 gbU48957.1 U48957 (Macaca fascicularis) | gi53575emb X01237.1 MMP53R (Mouse mRNA) | gi4996229 dbjAB020761.1 (Canis familiaris) |
|---|---|---|---|---|---|---|---|
| 1 | Human | GUACCACCAUCCACUACAA | UUGUAGUGGAUGGUGGUAC | [806-824] | | [835-852] | |
| 2 | Human | GGAAACUACUUCCUGAAAA | UUUUCAGGAAGUAGUUUCC | [188-206] | | [234-247] | |
| 3 | Human | AGACUCCAGUGGUAAUCUA | UAGAUUACCACUGGAGUCU | [894-912] | | [922-933] | |
| 4 | Human | CCAUCCACUACAACUACAU | AUGUAGUUGUAGUGGAUGG | [812-830] | | [840-858] | |

TABLE B-continued

| No. | Source | Sense | AntiSense | gi13097806 gbBC003596.1 (Homo sapiens) | gi2689466 gbU48957.1 U48957 (Macaca fascicularis) | gi53575emb X01237.1 MMP53R (Mouse mRNA) | gi4996229 dbjAB020761.1 (Canis familiaris) |
|---|---|---|---|---|---|---|---|
| 5 | Human | CCACCAUCCACUACAACUA | UAGUUGUAGUGGAUGGUGG | [809-827] | | [837-852] | |
| 6 | Human | AAACACUUUUCGACAUAGU | ACUAUGUCGAAAAGUGUUU | [747-765] | | — | |
| 7 | Human | CAUGAGCGCUGCUCAGAUA | UAUCUGAGCAGCGCUCAUG | [655-673] | | [683-696] | |
| 8 | Human | CCAUGGCCAUCUACAAGCA | UGCUUGUAGAUGGCCAUGG | [596-614] | | [624-640] | |
| 9 | Human | CCAAGUCUGUGACUUGCAC | GUGCAAGUCACAGACUUGG | [476-494] | | — | |
| 10 | Human | AAACUUUGCUGCCAAAAAA | UUUUUUGGCAGCAAAGUUU | [2476-2494] | | — | |
| 11 | Human | CCCUCCUUCUCCCUUUUUA | UAAAAGGGAGAAGGAGGG | [2421-2439] | | — | |
| 12 | Human | GCAAGCACAUCUGCAUUUU | AAAAUGCAGAUGUGCUUGC | [2389-2407] | | — | |
| 13 | Human | GGGUCAACAUCUUUUACAU | AUGUAAAAGAUGUUGACCC | [2367-2385] | | — | |
| 14 | Human | GAAGGGUCAACAUCUUUUA | UAAAAGAUGUUGACCCUUC | [2364-2382] | | — | |
| 15 | Human | CUGGAAGGGUCAACAUCUU | AAGAUGUUGACCCUUCCAG | [2361-2379] | | — | |
| 16 | Human | CCAGAGUGCUGGGAUUACA | UGUAAUCCCAGCACUCUGG | [2321-2339] | | — | |
| 17 | Human | GAUGGGGUCUCACAGUGUU | AACACUGUGAGACCCCAUC | [2249-2267] | | — | |
| 18 | Human | GCCAACUUUUGCAUGUUUU | AAAACAUGCAAAAGUUGGC | [2225-2243] | | — | |
| 19 | Human | CCAUGGCCAGCCAACUUUU | AAAAGUUGGCUGGCCAUGG | [2216-2234] | | — | |
| 20 | Human | AGACCCAGGUCCAGAUGAA | UUCAUCUGGACCUGGGUCU | [288-306] | | — | |
| 21 | Human, mouse | CCAUCAUCACACUGGAAGA | UCUUCCAGUGUGAUGAUGG | [878-896] | | [906-924] | |
| 22 | Human, mouse | CAUCACACUGGAAGACUCC | GGAGUCUUCCAGUGUGAUG | [882-900] | | [910-928] | |
| 23 | Human, mouse | CAUCAUCACACUGGAAGAC | GUCUUCCAGUGUGAUGAUG | [879-897] | | [907-925] | |
| 24 | Human, mouse | ACCAUCAUCACACUGGAAG | CUUCCAGUGUGAUGAUGGU | [877-895] | | [905-923] | |
| 25 | Human, mouse | AUCAUCACACUGGAAGACU | AGUCUUCCAGUGUGAUGAU | [880-898] | | [908-926] | |
| 26 | Human, mouse | CACUGGAAGACUCCAGUGG | CCACUGGAGUCUUCCAGUG | [887-905] | | [915-933] | |
| 27 | Human, cynomoglus, mouse | ACACUGGAAGACUCCAGUG | CACUGGAGUCUUCCAGUGU | [886-904] | [766-784] | [914-932] | |
| 28 | Human, cynomoglus, mouse | UCACUGGAAGACUCCAG | CUGGAGUCUUCCAGUGUGA | [884-902] | [764-782] | [912-930] | |
| 29 | Human, cynomoglus, mouse | AUCACACUGGAAGACUCCA | UGGAGUCUUCCAGUGUGAU | [883-901] | [763-781] | [911-929] | |
| 30 | Human, cynomoglus, mouse | CACAGCACAUGACGGAGGU | ACCUCCGUCAUGUGCUGUG | [617-635] | [497-515] | [645-663] | |
| 31 | Human, cynomoglus, mouse | CACUGGAAGACUCCAGUGG | CCACUGGAGUCUUCCAGUG | [887-905] | [767-785] | [915-933] | |
| 32 | Human, cynomoglus, mouse | UCACAGCACAUGACGGAGG | CCUCCGUCAUGUGCUGUGA | [616-634] | [496-514] | [644-662] | |

TABLE B-continued

| No. | Source | Sense | AntiSense | gi13097806 gbBC003596.1 (Homo sapiens) | gi2689466 gbU48957.1 U48957 (Macaca fascicularis) | gi53575emb X01237.1 MMP53R (Mouse mRNA) | gi4996229dbjAB020761.1 (Canis familiaris) |
|---|---|---|---|---|---|---|---|
| 33 | Human, cynomoglus, mouse | GUCACAGCACAUGACGGAG | CUCCGUCAUGUGCUGUGAC | [615-633] | [495-513] | [643-661] | |
| 34 | Human, cynomoglus, dog | CCAUCCACUACAACUACAU | AUGUAGUUGUAGUGGAUGG | [812-830] | [692-710] | | [702-720] |
| 35 | Human, cynomoglus, dog | CCACCAUCCACUACAACUA | UAGUUGUAGUGGAUGGUGG | [809-827] | [689-707] | | [699-717] |
| 36 | Human, cynomoglus, dog | GAAUAUUUCACCCUUCAGA | UCUGAAGGGUGAAAUAUUC | [1096-1114] | [976-994] | | [986-1004] |
| 37 | Human, cynomoglus, dog | CGAGUGGAAGGAAAUUUGC | GCAAAUUUCCUUCCACUCG | [706-724] | [586-604] | | [596-614] |
| 38 | Human, cynomoglus, dog | GAGAAUAUUUCACCCUUCA | UGAAGGGUGAAAUAUUCUC | [1094-1112] | [974-992] | | [984-1002] |
| 39 | Human, cynomoglus, dog | CUACAUGUGUAACAGUUCC | GGAACUGUUACACAUGUAG | [825-843] | [705-723] | | [715-733] |
| 40 | Human, cynomoglus, dog | AACUACAUGUGUAACAGUU | AACUGUUACACAUGUAGUU | [823-841] | [703-721] | | [713-731] |
| 41 | Human, cynomoglus, dog | CAACUACAUGUGUAACAGU | ACUGUUACACAUGUAGUUG | [822-840] | [702-720] | | [712-730] |
| 42 | Human, cynomoglus, dog | CACUACAACUACAUGUGUA | UACACAUGUAGUUGUAGUG | [817-835] | [697-715] | | [707-725] |
| 43 | Human cynomoglus, dog | CCACUACAACUACAUGUGU | ACACAUGUAGUUGUAGUGG | [816-834] | [696-714] | | [706-724] |
| 44 | Human, cynomoglus, dog | GACAGAAACACUUUUCGAC | GUCGAAAAGUGUUUCUGUC | [742-760] | [622-640] | | [632-650] |
| 45 | Human, cynomoglus, dog | GGAGAAUAUUUCACCCUUC | GAAGGGUGAAAUAUUCUCC | [1093-1111] | [973-991] | | [983-1001] |
| 46 | Human, cynomoglus, dog | GUGUAACAGUUCCUGCAUG | CAUGCAGGAACUGUUACAC | [831-849] | [711-729] | | [721-739] |
| 47 | Human, cynomoglus, dog | ACAACUACAUGUGUAACAG | CUGUUACACAUGUAGUUGU | [821-839] | [701-719] | | [711-729] |
| 48 | Human, cynomoglus, dog | ACUACAACUACAUGUGUAA | UUACACAUGUAGUUGUAGU | [818-836] | [698-716] | | [708-726] |
| 49 | Human, cynomoglus, dog | ACCAUCCACUACAACUACA | UGUAGUUGUAGUGGAUGGU | [811-829] | [691-709] | | [701-719] |
| 50 | Human, cynomoglus, dog | ACCACCAUCCACUACAACU | AGUUGUAGUGGAUGGUGGU | [808-826] | [688-706] | | [698-716] |

TABLE B-continued

| No. | Source | Sense | AntiSense | gi13097806 gbBC003596.1 (Homo sapiens) | gi2689466 gbU48957.1 U48957 (Macaca fascicularis) | gi53575emb X01237.1 MMP53R (Mouse mRNA) | gi4996229 dbjAB020761.1 (Canis familiaris) |
|---|---|---|---|---|---|---|---|
| 51 | Human, cynomoglus, dog | UACCACCAUCCACUACAAC | GUUGUAGUGGAUGGUGGUA | [807-825] | [687-705] | | [697-715] |
| 52 | Human, cynomoglus, dog | ACAGAAACACUUUUCGACA | UGUCGAAAAGUGUUUCUGU | [743-761] | [623-641] | | [633-651] |
| 53 | Human, cynomoglus, dog | GAGUGGAAGGAAAUUUGCG | CGCAAAUUUCCUUCCACUC | [707-725] | [587-605] | | [597-615] |
| 54 | Human, cynomoglus, dog | AUAUUUCACCCUUCAGAUC | GAUCUGAAGGGUGAAAUAU | [1098-1116] | [978-996] | | [988-1006] |
| 55 | Human, cynomoglus, dog | AAUAUUUCACCCUUCAGAU | AUCUGAAGGGUGAAAUAUU | [1097-1115] | [977-995] | | [987-1005] |
| 56 | Human, cynomoglus, dog | AGAAUAUUUCACCCUUCAG | CUGAAGGGUGAAAUAUUCU | [1095-1113] | [975-993] | | [985-1003] |
| 57 | Human, cynomoglus, dog | UGGAGAAUAUUUCACCCUU | AAGGGUGAAAUAUUCUCCA | [1092-1110] | [972-990] | | [982-1000] |
| 58 | Human, cynomoglus, dog | ACAUGUGUAACAGUUCCUG | CAGGAACUGUUACACAUGU | [827-845] | [707-725] | | [717-735] |
| 59 | Human, cynomoglus, dog | UACAACUACAUGUGUAACA | UGUUACACAUGUAGUUGUA | [820-838] | [700-718] | | [710-728] |
| 60 | Human, cynomoglus, dog | CUACAACUACAUGUGUAAC | GUUACACAUGUAGUUGUAG | [819-837] | [609-717] | | [709-727] |
| 61 | Human, cynomoglus, dog | UCCACUACAACUACAUGUG | CACAUGUAGUUGUAGUGGA | [815-833] | [695-713] | | [705-723] |
| 62 | Human, cynomoglus, dog | AUCCACUACAACUACAUGU | ACAUGUAGUUGUAGUGGAU | [814-832] | [694-712] | | [704-722] |
| 63 | Human, cynomoglus, dog | CAUCCACUACAACUACAUG | CAUGUAGUUGUAGUGGAUG | [813-831] | [693-711] | | [703-721] |
| 64 | Human, cynomoglus, dog | CACCAUCCACUACAACUAC | GUAGUUGUAGUGGAUGGUG | [810-828] | [690-708] | | [700-718] |
| 65 | Human, cynomoglus, dog | UGUGUAACAGUUCCUGCAU | AUGCAGGAACUGUUACACA | [830-848] | [710-728] | | [720-738] |
| 66 | Human, cynomoglus, dog | CAUGUGUAACAGUUCCUGC | GCAGGAACUGUUACACAUG | [828-846] | [708-726] | | [718-736] |
| 67 | Human, cynomoglus, dog | UACAUGUGUAACAGUUCCU | AGGAACUGUUACACAUGUA | [826-844] | [706-724] | | [716-734] |
| 68 | Human, cynomoglus, dog | ACUACAUGUGUAACAGUUC | GAACUGUUACACAUGUAGU | [824-842] | [704-722] | | [714-732] |

TABLE B-continued

| No. | Source | Sense | AntiSense | gi13097806 gbBC003596.1 (Homo sapiens) | gi2689466 gbU48957.1 U48957 (Macaca fascicularis) | gi53575emb X01237.1 MMP53R (Mouse mRNA) | gi4996229dbjAB020761.1 (Canis familiaris) |
|---|---|---|---|---|---|---|---|
| 69 | Human, cynomoglus, dog | AUCCGAGUGGAAGGAAAUU | AAUUUCCUUCCACUCGGAU | [703-721] | [583-601] | | [593-611] |
| 70 | Human, cynomoglus, dog | UCACUCCAGCCACCUGAAG | CUUCAGGUGGCUGGAGUGA | [1212-1230] | [1092-1110] | | [1102-1120] |
| 71 | Human, cynomoglus, dog | CUCACUCCAGCCACCUGAA | UUCAGGUGGCUGGAGUGAG | [1211-1229] | [1091-1109] | | [1101-1119] |

Note that in the above Table B, the sense strands of siRNAs 1-71 have SEQ ID NOS: 49-119 respectively, and the antisense strands of siRNAs 1-71 have SEQ ID NOS: 120-190 respectively.

Table C below shows 63 additional 21-mer siRNAs which have been generated by the proprietary algorithms.

TABLE C

| No. | Source | Sense SiRNA | AntiSense SiRNA | gi13097806 gbBC003596.1 (Homo sapiens) | gi2689466 gbU48957.1 U48957 (Macaca fascicularis) | gi53575emb X01237.1M MP53R (Mouse mRNA) | gi4996229dbj AB020761.1 (Canis familiaris) |
|---|---|---|---|---|---|---|---|
| 1 | Human | GGAAGAGAAUCUCCGCAAGAA | UUCUUGCGGAGAUUCUCUUCC | [975-995] | — | — | — |
| 2 | Human | GUACCACCAUCCACUACAACU | AGUUGUAGUGGAUGGUGGUAC | [806-826] | [686-706] | ]835-852] | [697-716] |
| 3 | Human | GGACGAUAUUGAACAAUGGUU | AACCAUUGUUCAAUAUCGUCC | [261-281] | — | — | — |
| 4 | Human | CCAGCCACCUGAAGUCCAAAA | UUUUGGACUUCAGGUGGCUGG | [1217-1237] | [1097-1115] | — | [1107-1120] |
| 5 | Human | GAGAAUAUUUCACCCUUCAGA | UCUGAAGGGUGAAAUAUUCUC | [1094-1114] | [974-994] | [1122-1137] | [984-1004] |
| 6 | Human | AGAAACCACUGGAUGGAGAAU | AUUCUCCAUCCAGUGGUUUCU | [1079-1099] | [959-979] | — | — |
| 7 | Human | CUACUGGGACGGAACAGCUUU | AAAGCUGUUCCGUCCCAGUAG | [910-930] | [790-810] | — | — |
| 8 | Human | AGACUCCAGUGGUAAUCUACU | AGUAGAUUACCACUGGAGUCU | [894-914] | [774-794] | [922-933] | [784-795] |
| 9 | Human | CUGGAAGACUCCAGUGGUAAU | AUUACCACUGGAGUCUUCCAG | [889-909] | [769-789] | [917-933] | [779-795] |
| 10 | Human | GAAACUACUUCCUGAAAACAA | UUGUUUUCAGGAAGUAGUUUC | [189-209] | [69-87] | [235-247] | [122-135] |
| 11 | Human | GGAAACUACUUCCUGAAAACA | UGUUUUCAGGAAGUAGUUUCC | [188-208] | [68-87] | [234-247] | [122-134] |
| 12 | Human | AAACACUUUUCGACAUAGUGU | ACACUAUGUCGAAAAGUGUUU | [747-767] | [627-647[9 | — | [637-657] |
| 13 | Human | GGAGUAUUUGGAUGACAGAAA | UUUCUGUCAUCCAAAUACUCC | [729-749] | [609-629] | — | — |
| 14 | Human | UCAGACCUAUGGAAACUACUU | AAGUAGUUUCCAUAGGUCUGA | [178-198] | [58-78] | [231-244] | — |
| 15 | Human | CCAUGGCCAUCUACAAGCAGU | ACUGCUUGUAGAUGGCCAUGG | [596-616] | [476-496] | [624-640] | [485-495] |
| 16 | Human | CCAAGUCUGUGACUUGCACGU | ACGUGCAAGUCACAGACUUGG | [476-496] | [356-376] | — | — |
| 17 | Human | GGACAGCCAAGUCUGUGACUU | AAGUCACAGACUUGGCUGUCC | [470-490] | [352-370] | [498-513] | [357-377] |
| 18 | Human | CCCUCCUUCUCCCUUUUUAUA | UAUAAAAGGGAGAAGGAGGG | [2421-2441] | — | [1721-1731] | — |
| 19 | Human, cynomoglus, dog | CCAUCCACUACAACUACAUGU | ACAUGUAGUUGUAGUGGAUGG | [812-832] | [692-712] | [840-860] | [702-722] |
| 20 | Human, cynomoglus, dog | CCACCAUCCACUACAACUACA | UGUAGUUGUAGUGGAUGGUGG | [809-829] | [689-709] | [837-857] | [699-719] |

TABLE C-continued

| No. | Source | Sense SiRNA | AntiSense SiRNA | gi13097806 gbBC003596.1 (Homo sapiens) | gi2689466 gbU48957.1 U48957 (Macaca fascicularis) | gi53575emb X01237.1M MP53R (Mouse mRNA) | gi4996229dbj AB020761.1 (Canis familiaris) |
|---|---|---|---|---|---|---|---|
| 21 | Human, cynomoglus, dog | GAGAAUAUUUCACCCUUCAGA | UCUGAAGGGUGAAAUAUUCUC | [1094-1114] | [974-994] | | [984-1004] |
| 22 | Human, cynomoglus, dog | GGAGAAUAUUUCACCCUUCAG | CUGAAGGGUGAAAUAUUCUCC | [1093-1113] | [973-993] | | [983-1003] |
| 23 | Human, cynomoglus, dog | CUACAUGUGUAACAGUUCCUG | CAGGAACUGUUACACAUGUAG | [825-845] | [705-725] | | [715-735] |
| 24 | Human, cynomoglus, dog | ACAACUACAUGUGUAACAGUU | AACUGUUACACAUGUAGUUGU | [821-841] | [701-721] | | [711-731] |
| 25 | Human, cynomoglus, dog | CCACUACAACUACAUGUGAA | UUACACAUGUAGUUGUAGUGG | [816-836] | [696-716] | | [706-726] |
| 26 | Human, cynomoglus, dog | CACCAUCCACUACAACUACAU | AUGUAGUUGUAGUGGAUGGUG | [810-830] | [690-710] | | [700-720] |
| 27 | Human, cynomoglus, dog | GAAUAUUUCACCCUUCAGAUC | GAUCUGAAGGGUGAAAUAUUC | [1096-1116] | [976-996] | | [986-1006] |
| 28 | Human, cynomoglus, dog | AGAAUAUUUCACCCUUCAGAU | AUCUGAAGGGUGAAAUAUUCU | [1095-1115] | [975-995] | | [985-1005] |
| 29 | Human, cynomoglus, dog | UACCACCAUCCACUACAACUA | UAGUUGUAGUGGAUGGUGGUA | [807-827] | [687-707] | | [697-717] |
| 30 | Human, cynomoglus, dog | GAUGGAGAAUAUUUCACCCUU | AAGGGUGAAAUAUUCUCCAUC | [1090-1110] | [970-990] | | [980-1000] |
| 31 | Human, cynomoglus, dog | CCGAGUGGAAGGAAAUUUGCG | CGCAAAUUUCCUUCCACUCGG | [705-725] | [585-605] | | [595-615] |
| 32 | Human, cynomoglus, dog | AACUACAUGUGUAACAGUUCC | GGAACUGUUACACAUGUAGUU | [823-843] | [703-723] | | [713-733] |
| 33 | Human, cynomoglus, dog | CAACUACAUGUGUAACAGUUC | GAACUGUUACACAUGUAGUUG | [822-842] | [702-722] | | [712-732] |
| 34 | Human, cynomoglus, dog | ACUACAACUACAUGUGUAACA | UGUUACACAUGUAGUUGUAGU | [818-838] | [698-718] | | [708-728] |
| 35 | Human, cynomoglus, dog | CACUACAACUACAUGUGUAAC | GUUACACAUGUAGUUGUAGUG | [817-837] | [697-717] | | [707-727] |
| 36 | Human, cynomoglus, dog | UCCACUACAACUACAUGUGUA | UACACAUGUAGUUGUAGUGGA | [815-835] | [695-715] | | [705-725] |
| 37 | Human, cynomoglus, dog | CAUCCACUACAACUACAUGUG | CACAUGUAGUUGUAGUGGAUG | [813-833] | [693-713] | | [703-723] |
| 38 | Human, cynomoglus, dog | ACCAUCCACUACAACUACAUG | CAUGUAGUUGUAGUGGAUGGU | [811-831] | [691-711] | | [701-721] |

TABLE C-continued

| No. | Source | Sense SiRNA | AntiSense SiRNA | gi13097806 gbBC003596.1 (Homo sapiens) | gi2689466 gbU48957.1 U48957 (Macaca fascicularis) | gi53575emb X01237.1M MP53R (Mouse mRNA) | gi4996229dbj AB020761.1 (Canis familiaris) |
|---|---|---|---|---|---|---|---|
| 39 | Human, cynomoglus, dog | UGGAGAAUAUUUCACCCUUCA | UGAAGGGUGAAAUAUUCCCA | [1092-1112] | [972-992] | | [982-1002] |
| 40 | Human, cynomoglus, dog | AUGUGUAACAGUUCCUGCAUG | CAUGCAGGAACUGUUACACAU | [829-849] | [709-729] | | [719-739] |
| 41 | Human, cynomoglus, dog | CAUGUGUAACAGUUCCUGCAU | AUGCAGGAACUGUUACACAUG | [828-848] | [708-728] | | [718-738] |
| 42 | Human, cynomoglus, dog | UACAACUACAUGUGUAACAGU | ACUGUUACACAUGUAGUUGUA | [820-840] | [700-720] | | [710-730] |
| 43 | Human, cynomoglus, dog | CUACAACUACAUGUGUAACAG | CUGUUACACAUGUAGUUGUAG | [819-839] | [699-719] | | [709-729] |
| 44 | Human, cynomoglus, dog | AUCCACUACAACUACAUGUGU | ACACAUGUAGUUGUAGUGGAU | [814-834] | [694-714] | | [704-724] |
| 45 | Human, cynomoglus, dog | ACCACCAUCCACUACAACUAC | GUAGUUGUAGUGGAUGGUGGU | [808-828] | [688-708] | | [698-718] |
| 46 | Human, cynomoglus, dog | AAUAUUUCACCCUUCAGAUCC | GGAUCUGAAGGGUGAAAUAUU | [1097-1117] | [977-997] | | [987-1007] |
| 47 | Human, cynomoglus, dog | ACUACAUGUGUAACAGUUCCU | AGGAACUGUUACACAUGUAGU | [824-844] | [704-724] | | [714-734] |
| 48 | Human, cynomoglus, dog | AUGGAGAAUAUUUCACCCUUC | GAAGGGUGAAAUAUUCUCCAU | [1091-1111] | [971-991] | | [981-1001] |
| 49 | Human, cynomoglus, dog | UGUGUAACAGUUCCUGCAUGG | CCAUGCAGGAACUGUUACACA | [830-850] | [710-730] | | [720-740] |
| 50 | Human, cynomoglus, dog | UCCGAGUGGAAGGAAAUUUGC | GCAAAUUUCCUUCCACUCGGA | [704-724] | [584-604] | | [594-614] |
| 51 | Human, cynomoglus, dog | AUCCGAGUGGAAGGAAAUUUG | CAAAUUUCCUUCCACUCGGAU | [703-723] | [583-603] | | [593-613] |
| 52 | Human, cynomoglus, mouse | UCACACUGGAAGACUCCAGUG | CACUGGAGUCUUCCAGUGUGA | [884-904] | [764-784] | [912-932] | |
| 53 | Human, cynomoglus, mouse | AUCACACUGGAAGACUCCAGU | ACUGGAGUCUUCCAGUGUGAU | [883-903] | [763-783] | [911-931] | |
| 54 | Human, cynomoglus, mouse | CACACUGGAAGACUCCAGUGG | CCACUGGAGUCUUCCAGUGUG | [885-905] | [765-785] | [913-933] | |
| 55 | Human, mouse | UCAUCACACUGGAAGACUCCA | UGGAGUCUUCCAGUGUGAUGA | [881-901] | | [909-929] | |
| 56 | Human, mouse | CCAUCACACUGGAAGACU | AGUCUUCCAGUGUGAUGAUGG | [878-898] | | [906-926] | |
| 57 | Human, mouse | CAUCACACUGGAAGACUCCAG | CUGGAGUCUUCCAGUGUGAUG | [882-902] | | [910-930] | |

TABLE C-continued

| No. | Source | Sense SiRNA | AntiSense SiRNA | gi13097806 gbBC003596.1 (Homo sapiens) | gi2689466 gbU48957.1 U48957 (Macaca fascicularis) | gi53575emb X01237.1M MP53R (Mouse mRNA) | gi4996229dbj AB020761.1 (Canis familiaris) |
|---|---|---|---|---|---|---|---|
| 58 | Human, mouse | CAUCAUCACACUGGAAGACUC | GAGUCUUCCAGUGUGAUGAUG | [879-899] | | [907-927] | |
| 59 | Human, mouse | ACCAUCAUCACACUGGAAGAC | GUCUUCCAGUGUGAUGAUGGU | [877-897] | | ]905-925] | |
| 60 | Human, mouse | UCACACUGGAAGACUCCAGUG | CACUGGAGUCUUCCAGUGUGA | [884-9041 | | [912-932] | |
| 61 | Human, mouse | AUCACACUGGAAGACUCCAGU | ACUGGAGUCUUCCAGUGUGAU | [883-903] | | [911-931] | |
| 62 | Human, mouse | AUCAUCACACUGGAAGACUCC | GGAGUCUUCCAGUGUGAUGAU | [880-900] | | [908-928] | |
| 63 | Human, mouse | CACACUGGAAGACUCCAGUGG | CCACUGGAGUCUUCCAGUGUG | [885-905] | | [913-933] | |

Note that in the above Table C, the sense strands of siRNAs 1-63 have SEQ ID NOS: 191-253 respectively, and the antisense strands of siRNAs 1-63 have SEQ ID NOS: 254-316 respectively.

Example 2

Testing the siRNA Compounds for Anti-p53 Activity

Protocols

I. Preparation of the siRNAs (Double-Stranded Oligonucleotides)

Lyophilized oligonucleotides were dissolved in RNAse free distilled water to produce a final concentration of 100 uM. The diluted oligonucleotides were kept at room temperature for 15 min and immediately frozen in liquid nitrogen.

The oligonucleotides were stored at −80° C. and diluted before use with PBS.

II. Transfection of siRNA in Human cells with Lipofectamine2000 Reagent:

$2 \times 10^5$ p53-wt HCT116 or SW480 cells were seeded per well in 6 wells plate. 24 h subsequently, cells were transfected with p53 oligonucleotides using lipofectamine2000 reagent (obtained from Invitrogen).

The following procedure was performed:
1. Before transfection, the cell medium was replaced by 1500 ul fresh medium without antibiotics.
2. In a sterile, plastic tube, Lipofectamine2000 reagent (the amount is calculated according to 5 ul per well) was added to 250 ul serum-free medium, and incubated for 5 min at room temperature.
3. In another tube the human anti-p53 oligonucleotides (varying amounts to fit the desired final concentration per well) were added to 250 ul serum-free medium.
4. Lipofectamine2000 complex was combined with the p53 oligonucleotide solution and incubated for 20 min at room temperature.
5. The resulting mixture was added dropwise to the cells, and the cells were incubated at 37° C.
6. SW480 cells: 48 hr after transfection the cells were harvested and proteins were extracted using RIPA buffer.
7. HCT116 cells:
   40 h after transfection, 5Fu (Sigma) was added to cells to produce a final concentration of 25 ug/ml.48 h after cells transfection (8 h after 5Fu treatment), the cells were harvested and proteins were extracted using RIPA buffer.
8. p53 expression was determined by Western Blot analysis using monoclonal antibody (Do-1 clone, Santa Cruz). For normalization, blots were examined for Tubulin expression.

III Co-Transfection of Mouse p53 Gene and Mouse p53 Oligonucleotides into PC3 Cells using Lipofectamine2000 Reagent:

$2 \times 10^5$ p53-null PC3 cells were seeded per well in 6 wells plate. 24 h subsequently, cells were Co-transfected with mouse p53 gene and GFP gene and mouse p53 oligonucleotides using lipofectamine2000 reagent (Invitrogen). The following procedure was performed:
1. Before transfection cell medium was replaced by 1500 ul fresh medium without antibiotics.
2. In sterile, plastic tube, Lipofectamine2000 reagent (5 ul per well) was added to 250 ul serum-free medium, and incubated for 5 min at room temperature.
3. In another tube 4 ug DNA (p53gene:GFPgene, 10:1) and human p53 oligonucleotides were added to 250 ul serum free medium.
4. Lipofectamine2000 complex was combined with p53 oligonucleotides solution and incubated for 20 min at room temperature.
5. The mixture solution was added dropwise to the cells, and cells were incubated at 37° C.
6. 48 h after transfection, cells were harvested and proteins were extracted using RIPA buffer.
7. p53 expression was determined by Western Blot analysis using monoclonal antibody (Clone240, Chemicon). For normalization, blots were examined for GFP expression.

Results:
A. Human p53 Oligonucleotides:

TABLE D

| Number | oligo | species | source | Results of Test SW480 | Results of Test HCT116 |
|---|---|---|---|---|---|
| 2 | Hu2' | human | literature | (−) | (+) |
| 3 | QHMon1 | human, monkey | Proprietary | (++) | (+++) |
| 4 | QHMon2 | human, monkey | Proprietary | (−) | Not tested |
| 5 | QH1 | human | Proprietary | (+++) | (+++) |
| 6 | QH2 | human | Proprietary | (−) | Not tested |
| 13 | A17 | human, mouse | Proprietary | (−) | Not tested |
| 14 | E2 | human, mouse, rat | Proprietary | (+) | Not tested |
| 15 | E6 | human, mouse, rat | Proprietary | (−) | Not tested |
| 16 | B1 | human, mouse, rat | Proprietary | (−) | Not tested |
| 17 | B2 | human, mouse, rat | Proprietary | (−) | Not tested |
| 18 | C1 | human, monkey, mouse | Proprietary | (−) | Not tested |
| 19 | F2 | human, monkey, dog | Proprietary | (−) | Not tested |
| 20 | F3 | human, monkey, dog | Proprietary | (+++) | (+++) |
| 21 | G1 | human, monkey, dog | Proprietary | (+++) | Not tested |
| 22 | H2 | human, monkey, dog | Proprietary | (+) | Not tested |
| 23 | I5 | human, monkey, dog | Proprietary | (+++) | Not tested |

Note:
The numbers in Table D correspond to the numbers used in Table A, where the sense strands of siRNAs 1-23 have SEQ ID NOS: 3-25 respectively, and the antisense strands of siRNAs 1-23 have SEQ ID NOS: 26-48 respectively.

As shown in Table D, four human oligonucleotides were tested in two systems SW480 and HCT116, according to Protocols II above. Representative results (Western Blot) on which the Results of Test was based are shown in FIG. 3.

B. Mouse p53 Oligonucleotides:

TABLE E

| oligo | species | source | Results of Test PC3 null cells/exogenous mouse p53 |
|---|---|---|---|
| 1 Mo3 | mouse | literature | (+++) |
| 7 QM1 | mouse | Proprietary | (−) |
| 8 QM2 | mouse | Proprietary | (−) |
| 9 QM3 | mouse | Proprietary | (−) |
| 10 QM6 | mouse | Proprietary | (−) |
| 11 QM4 | mouse, rat | Proprietary | (+++) |
| 12 QM5 | mouse, rat | Proprietary | (+++) |
| 13 A17 | human, mouse | Proprietary | (−) |
| 14 E2 | human, mouse, rat | Proprietary | (++) |
| 15 E6 | human, mouse, rat | Proprietary | (−) |
| 16 B1 | human, monkey, mouse | Proprietary | (−) |
| 17 B2 | human, monkey, mouse | Proprietary | (++) |
| 18 C1 | human, monkey, mouse | Proprietary | (++) |
| 21 G1 | human, monkey, dog | Proprietary | (++) |
| 20 F3 | human, monkey, dog | Proprietary | (+++) |
| 23 I5 | human, monkey, dog | Proprietary | (−) |
| 3 QHMon1 | human, monkey | Proprietary | (++) |

Figure 4:
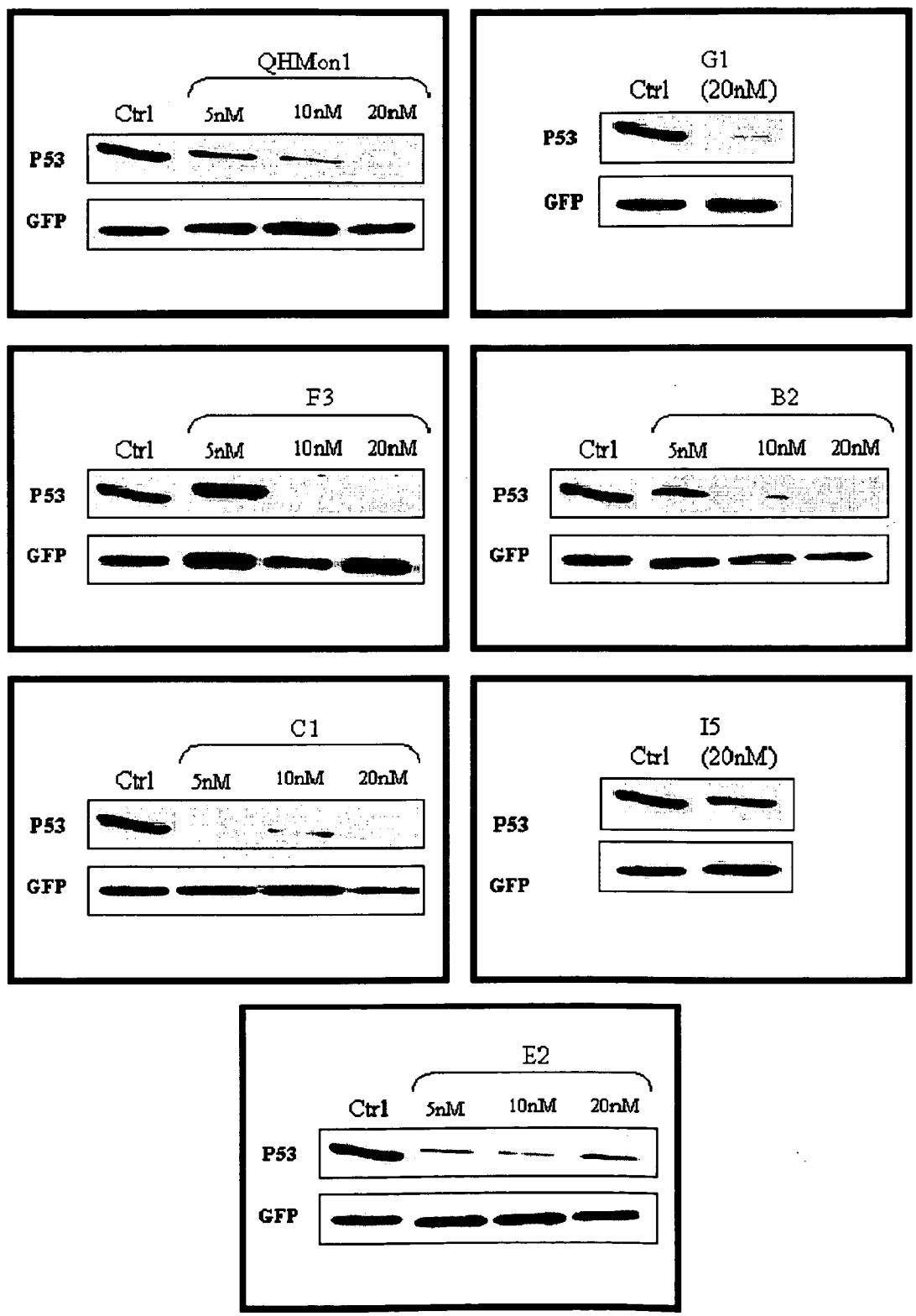
FIG. 4. This figure shows Western Blot results demonstrating the effect of various mouse p53 siRNAs on p53 expression.

Note:
The numbers in Table E (as for Table D) correspond to the numbers used in Table A, where the sense strands of siRNAs 1-23 have SEQ ID NOS: 3-25 respectively, and the antisense strands of siRNAs 1-23 have SEQ ID NOS: 26-48 respectively. Representatives of the Western Blot results on which the Results of Test was based are shown in FIG. 4.

Example 3

Model Systems of Hair Loss

Testing the active siRNA may be done in the following systems:
a. Mouse model of hair loss
b. Ex-vivo cultured human hair follicles
c. Human hair follicle graft in nude mice Note: Systems for testing the active siRNA are described in Botcharev et al, 2000, *p53 is essential for Chemotherapy—induced Hair Loss*, Cancer Research, 60, 5002-5006).

Example 4

Model Systems of Acute Renal Failure (ARF)

Testing the active siRNA for treating ARF may be done using sepsis-induced ARF or ischemia-reperfusion-induced ARF.

1. Sepsis Induced ARF

Two predictive animal models of sepsis-induced ARF are described by Miyaji T, Hu X, Yuen P S, Muramatsu Y, Iyer S, Hewitt S M, Star R A, 2003, *Ethyl pyruvate decreases sepsis-induced acute renal failure and multiple organ damage in aged mice*, Kidney Int. November; 64(5):1620-31. These two models are lipopolysaccharide administration and cecal ligation puncture in mice, preferably in aged mice.

2. Ischemia-Reperfusion-Induced ARF

This predictive animal model is described by Kelly K J, Plotkin Z, Vulgamott S L, Dagher P C, 2003 January, *P53 mediates the apoptotic response to GTP depletion after renal ischemia-reperfusion: protective role of a p53 inhibitor*, J Am Soc Nephrol.;14(1):128-38.

Ischemia-reperfusion injury was induced in rats following 45 minutes bilateral kidney arterial clamp and subsequent release of the clamp to allow 24 hours of reperfusion. 250 µg of p53 siRNA (QM5 sequence, Table A) were injected into the jugular vein 2 hrs prior to and 30 minutes following the clamp. Additional 250 µg of siRNA were given via the tail vein at 4 and 8 hrs after the clamp. siRNA against GFP served as a negative control. The siRNA used in the experiments described herein had a phosphate group at the 3' terminus of both the sense and antisense strand. The 3'-non-phosphorylated siRNA has been found to have similar biological activity in an animal model as the corresponding 3'-phosphorylated siRNA. ARF progression was monitored by measurement of serum creatinine levels before and 24 hrs post surgery. At the end of the experiment, the rats were perfused via an indwelling femoral line with warm PBS followed by 4% paraformaldehyde. The left kidneys were removed and stored in 4% paraformaldehyde for subsequent histological analysis. Acute renal failure is frequently defined as an acute increase of the serum creatinine level from baseline. An increase of at least 0.5 mg per dL or 44.2 μmol per L of serum creatinine is considered as an indication for acute renal failure. Serum creatinine was measured at time zero before the surgery and at 24 hours post ARF surgery.

To study the distribution of p53 siRNA in the rat kidney, Cy3-labeled 19-mer blunt-ended siRNA molecules (2 mg/kg) having alternating O-methyl modification in the sugar residues were administered iv for 3-5 min, after which in vivo imaging was conducted using two-photon confocal microscopy. The confocal microscopy analysis revealed that the majority of siRNA in the kidneys is concentrated in the endosomal compartment of proximal tubular cells. Both endosomal and cytoplasmic siRNA fluorescence were relatively stable during the first 2 hrs post delivery and disappeared at 24 hrs.

Figure 5:
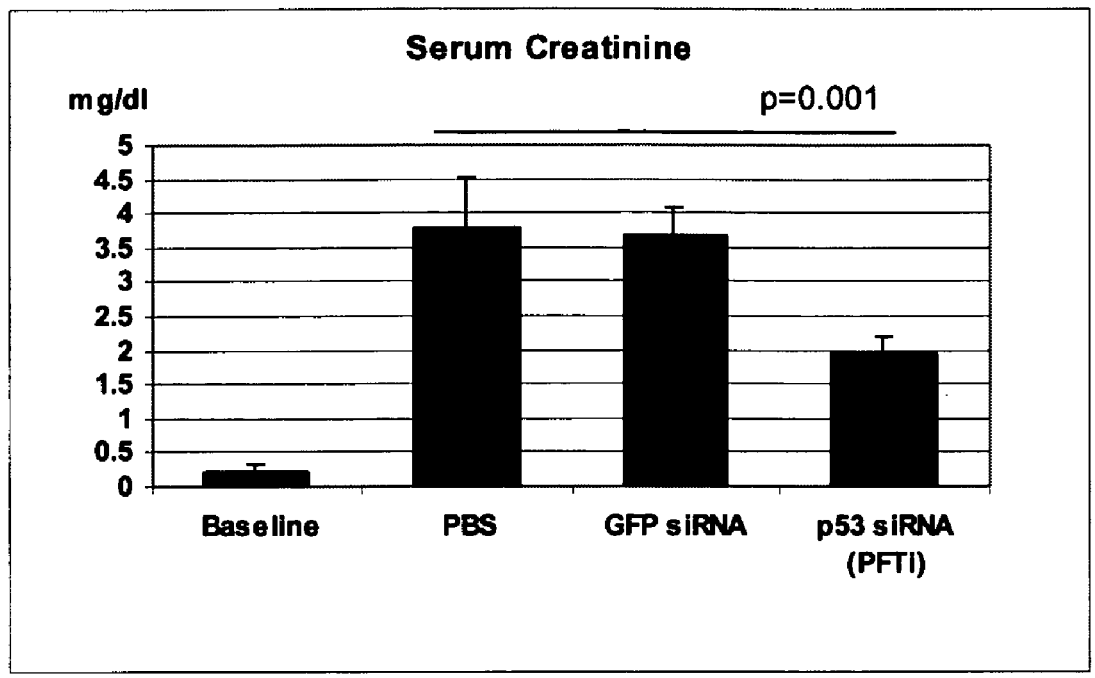
FIG. 5. This figure shows the level of serum creatinine as an indication for acute renal failure in animals that underwent bilateral kidney arterial clamp and were treated with p53 siRNA compound or a control, as indicated.

As evident from FIG. 5, there was a ten-fold increase in the level of serum creatinine following the 45-min of kidney bilateral arterial clamp treatment (PBS treatment). Four injections of p53 siRNA (QM5 sequence, Table A) (2 hrs prior to the clamp and 30 min, 4 h and 8 h after the clamp) significantly reduced the creatinine level in serum by 50% (P< (0.001). These results suggest that p53 siRNA can protect renal tissue from the effects of ischemia-reperfusion injury and thus reduces the severity of ARF.

Figure 6:
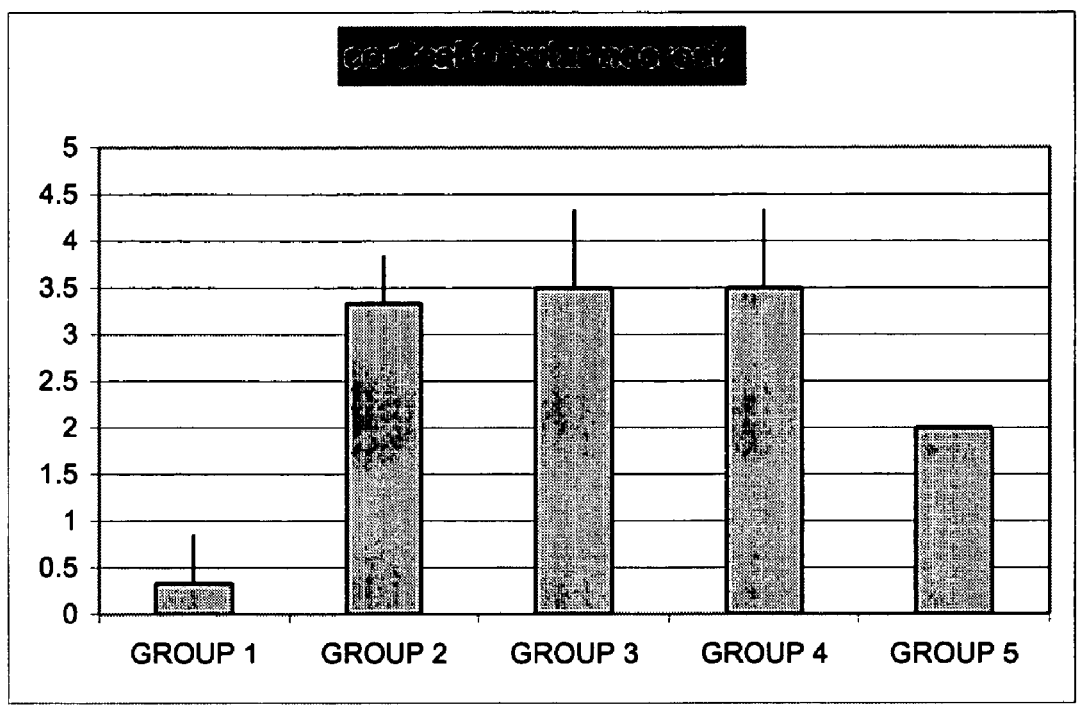
FIG. 6. This figure shows the extent of tubular necrosis in renal tissue in animals that underwent bilateral kidney arterial clamp and were treated with the p53 siRNA compound.
Figure 7:
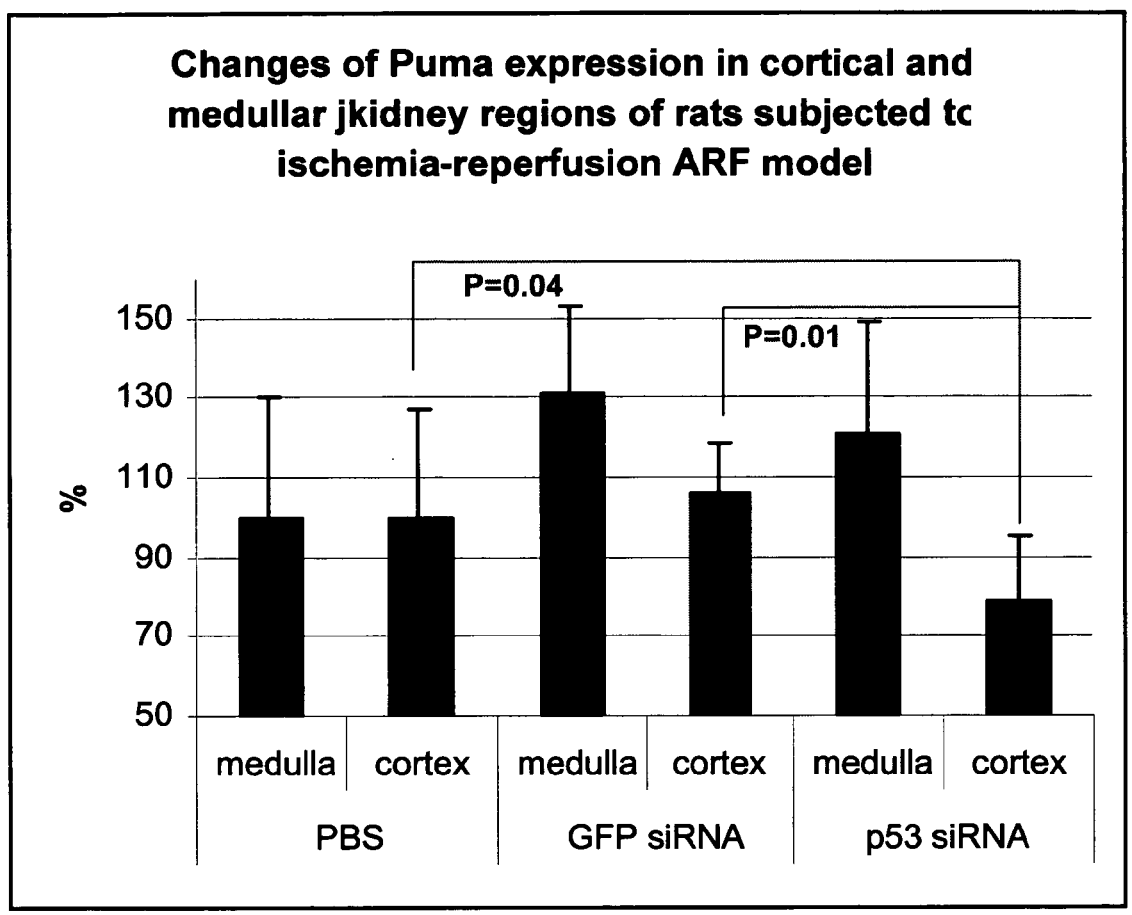
FIG. 7. This figure demonstrates that p53 siRNA treatment down-regulated the expression of the pro-apoptotic gene Puma in the cortical compartment of the kidney in animal subjected to ischemia-reperfusion kidney injury.

The effect of p53 siRNA treatment on renal ischemia-reperfusion injury was further determined by analysing the extent of tubular necrosis in the renal tissue. Tubular necrosis may be scored as: no damage (damage scoring 0), unicellular, patchy isolated necrosis (damage scoring 1), tubular necrosis in less than 25% of the tissue (damage scoring 2), tubular necrosis in between 25 and 50% of the tissue (damage scoring 3) and tubular necrosis in more than 50%, of the tissue (damage scoring 4). FIG. 6 demonstrates the tubular kidney damage expressed as damage scoring (Y-axis) in animals that did not undergo ischemia-reperfusion injury (group 1) or in ischemia-reperfusion injury animals following treatment with either PBS (group 2), two injections of p53 siRNA (group 3), three injections of p53 siRNA (group 4) or four injections of p53 siRNA (group 5). As revealed by FIG. 6, four injections of p53 siRNA led to significant decrease in the tubular kidney damage as compared to the PBS control group. FIG. 7 demonstrates that four injections of p53 siRNA treatment down-regulated the expression of the pro-apoptotic gene Puma in the cortical compartment of the kidney in animal subjected to ischemia-reperfusion injury. This indicates that p53 siRNA treatment is capable of inhibiting the apoptotic processes in the kidney following ischemia-reperfusion injury.

What is claimed is:

1. A method of treating a patient at risk for the development of, or suffering from, acute renal failure comprising administering to the patient a double-stranded compound having the structure:

5' ugaagggugaaauauucuc 3' (antisense strand) (SEQ ID NO: 48)
3' acuucccacuuuauaagag 5' (sense strand) (SEQ ID NO: 25)

wherein each of a, c, u and g is an unmodified or 2'O-Methyl sugar modified ribonucleotide and each consecutive ribonucleotide is joined to the next ribonucleotide by a covalent bond;
wherein alternating ribonucleotides in both the antisense strand and the sense strand are 2'O-Methyl sugar modified;
wherein a 2'O-Methyl sugar modified ribonucleotide is present at both the 5' terminus and the 3' terminus of the antisense strand and an unmodified ribonucleotide is present at both the 5' terminus and the 3' terminus of the sense strand; and
wherein the compound is administered in an amount effective to treat the patient.

2. The method of claim 1, wherein the covalent bond is a phosphodiester bond.

3. The method of claim 1, wherein the patient is at risk for the development of acute renal failure as a result of major cardiac surgery.

4. A method of preventing acute renal failure in a patient undergoing surgery comprising administering to the patient a double-stranded compound having the structure:

5' ugaagggugaaauauucuc 3' (antisense strand) (SEQ ID NO: 48)
3' acuucccacuuuauaagag 5' (sense strand) (SEQ ID NO: 25)

wherein each of a, c, u and g is an unmodified or 2'O-Methyl sugar modified ribonucleotide and each consecutive ribonucleotide is joined to the next ribonucleotide by a covalent bond;
wherein alternating ribonucleotides in both the antisense strand and the sense strand are 2'O-Methyl sugar modified;
wherein a 2'O-Methyl sugar modified ribonucleotide is present at both the 5' terminus and the 3' terminus of the antisense strand and an unmodified ribonucleotide is present at the 5' terminus and the 3' terminus of the sense strand; and
wherein the compound is administered in an amount effective to prevent acute renal failure in the patient.

5. The method of claim 4, wherein the surgery is cardiac surgery.

6. The method of claim 4, wherein the surgery is vascular surgery.

7. The method of claim 1, wherein the acute renal failure is ischemia-reperfusion-induced acute renal failure.

8. The method of claim 1, wherein the acute renal failure is sepsis-associated acute renal failure.

9. The method of claim 1, wherein the acute renal failure is toxic acute renal failure due to chemotherapy treatment.

10. The method of claim 1, wherein the patient is a kidney transplant patient.

11. The method of claim 4, wherein the covalent bond is a phosphodiester bond.

12. The method of claim 4, wherein the acute renal failure is ischemia-reperfusion-induced acute renal failure.

13. The method of claim 4, wherein the acute renal failure is sepsis-associated acute renal failure.

14. The method of claim 4, wherein the patient is a kidney transplant patient.

15. A method of treating a patient at risk for the development of, or suffering from, acute renal failure comprising administering to the patient a double-stranded compound having the structure:

5' ugaagggugaaauauucuc 3' (antisense strand) (SEQ ID NO: 48)
3' acuucccacuuuauaagag 5' (sense strand) (SEQ ID NO: 25)

wherein each of a, c, u and g is a ribonucleotide and each consecutive ribonucleotide is joined to the next ribonucleotide by a phosphodiester bond;
wherein alternating ribonucleotides in both the antisense strand and the sense strand are 2'-O-Methyl sugar modified;
wherein a 2'-O-Methyl sugar modified ribonucleotide is present at both the 5' terminus and the 3' terminus of the antisense strand and an unmodified ribonucleotide is present at both the 5' terminus and the 3' terminus of the sense strand;
wherein the ribonucleotide at the 3' terminus and the ribonucleotide at the 5' terminus are non-phosphorylated in both the antisense strand and the sense strand; and
wherein the compound is administered in an amount effective to treat the patient.

16. The method of claim 15, wherein the patient is at risk for the development of acute renal failure as a result of major cardiac surgery.

17. The method of claim 15, wherein the acute renal failure is ischemia-reperfusion-induced acute renal failure.

18. The method of claim 15, wherein the acute renal failure is sepsis-associated acute renal failure.

19. The method of claim 15, wherein the acute renal failure is toxic acute renal failure due to chemotherapy treatment.

20. The method of claim 15, wherein the patient is a kidney transplant patient.

21. A method of preventing acute renal failure in a patient undergoing surgery comprising administering to the patient a double-stranded compound having the structure:

5' ugaagggugaaauauucuc 3' (antisense strand) (SEQ ID NO: 48)
3' acuucccacuuuauaagag 5' (sense strand) (SEQ ID NO: 25)

wherein each of a, c, u and g is a ribonucleotide and each consecutive ribonucleotide is joined to the next ribonucleotide by a phosphodiester bond;
wherein alternating ribonucleotides in both the antisense strand and the sense strand are 2'-O-Methyl sugar modified;
wherein a 2'-O-Methyl sugar modified ribonucleotide is present at both the 5' terminus and the 3' terminus of the antisense strand and an unmodified ribonucleotide is present at both the 5' terminus and the 3' terminus of the sense strand;
wherein the ribonucleotide at the 3' terminus and the ribonucleotide at the 5' terminus are non-phosphorylated in both the antisense strand and the sense strand; and
wherein the compound is administered in an amount effective to prevent acute renal failure in the patient.

22. The method of claim 21, wherein the surgery is cardiac surgery.

23. The method of claim 21, wherein the surgery is vascular surgery.

24. The method of claim 21, wherein the acute renal failure is ischemia-reperfusion-induced acute renal failure.

25. The method of claim 21, wherein the acute renal failure is sepsis-associated acute renal failure.

26. The method of claim 21, wherein the patient is a kidney transplant patient.

* * * * *